US010513700B2

(12) United States Patent
Hansen et al.

(10) Patent No.: US 10,513,700 B2
(45) Date of Patent: Dec. 24, 2019

(54) METHOD FOR MAKING AN ENRICHED LIBRARY

(71) Applicant: Vipergen ApS, Copenhagen (DK)

(72) Inventors: Nils Jakob Vest Hansen, Copenhagen (DK); Allan Beck Christensen, Copenhagen (DK); Leif Kongskov Larsen, Copenhagen (DK); Frank Abildgaard Slok, Copenhagen (DK); Lars Kolster Petersen, Copenhagen (DK); Judith Rasmussen-Dietvorst, Copenhagen (DK); Peter Blakskjaer, Copenhagen (DK); Tara Heitner Hansen, Copenhagen (DK); Johan Holmkvist, Copenhagen (DK)

(73) Assignee: Vipergen ApS, Copenhagen (DK)

( * ) Notice: Subject to any disclaimer, the term of this patent is extended or adjusted under 35 U.S.C. 154(b) by 0 days.

(21) Appl. No.: 15/364,337

(22) Filed: Nov. 30, 2016

(65) Prior Publication Data

US 2017/0233726 A1    Aug. 17, 2017

Related U.S. Application Data

(63) Continuation of application No. 13/636,668, filed as application No. PCT/EP2011/065117 on Sep. 1, 2011, now abandoned.

(30) Foreign Application Priority Data

Sep. 27, 2010  (EP) ..................................... 10180435

(51) Int. Cl.
    *C12N 15/10* (2006.01)
(52) U.S. Cl.
    CPC ..... *C12N 15/1075* (2013.01); *C12N 15/1068* (2013.01)
(58) Field of Classification Search
    None
    See application file for complete search history.

(56) References Cited

U.S. PATENT DOCUMENTS

| 2006/0078888 | A1* | 4/2006 | Griffiths ................ B01F 3/0807 435/6.11 |
| 2006/0099626 | A1  | 5/2006 | Harbury |
| 2008/0305957 | A1* | 12/2008 | Thisted .............. C12N 15/1068 506/4 |
| 2009/0062147 | A1  | 3/2009 | Morgan |
| 2009/0170069 | A1* | 7/2009 | Ghosh ................ G01N 33/6845 435/5 |

FOREIGN PATENT DOCUMENTS

| EP | 1423400 | 8/2006 |
| EP | 1402024 | 8/2007 |
| EP | 1809743 | 12/2008 |
| WO | 0023458 | 4/2000 |
| WO | 06053571 | 5/2006 |
| WO | 2008103900 | 8/2008 |
| WO | 11005221 | 1/2011 |

OTHER PUBLICATIONS

Griffiths et al. (Trends in biotechnology 24.9 (2006): 395-402). (Year: 2006).*
Rissin et al. (Nano letters 6.3 (2006): 520-523.). (Year: 2006).*
Theberge et al. Microdroplets in Microfluidics: An Evolving Platform for Discoveries in Chemistry and Biology. Angew. Chem. Int. Ed. 49: 5846-5868. 2010.
Theodoropoulos et al. Conformationally Restricted C-Terminal Peptides of Substance P. Synthesis, Mass Spectral Analysis and Pharmacological Properties. J. Med. Chem. 28(10): 1536-1539. 1985.
Turner et al. High-Throughput Haplotype Determination Over Long Distances by Haplotype Fusion PCR and Ligation Haplotyping. Nat Protoc. 4: 1771-1783. 2009.
Vogelstein et al. Digital PCR. Proc. Natl. Acad. Sci. 96: 9236-9241. 1999.
Weber et al. 2-(Tributylstannyl)-4-[3-(trifluoromethyl)-3H-diazirin-3-yl]benzyl Alcohol: A Building Block for Photolabeling and Cross-Linking Reagents of Very High Specific Radioactivity. J. Am. Soc. Chem. 117(11): 3084-3095. 1995.
Williams et al. Amplification of Complex Gene Libraries by Emulsion PCR. Nat. Methods. 3(7): 545-550. 2006.
Wrenn et al. Synthetic Ligands Discovered by In Vitro Selection. J. Am. Chem. Soc. 129: 13137-13143. 2007.
Yonezawa et al. DNA Display for In Vitro Selection of Diverse Peptide Libraries. Nucleic Acids Res. 31: e118. 2003.
Zhang et al. DNA Display Technique: Principle and Application. Int. J. Biological Sciences. 29: 126-129. 2006.
Zheng et al. Selection of Restriction Endonucleases Using Artificial Cells. Nucleic Acids Res. 35: e83. 2007.
Anarbaev et al. Klenow Fragment and DNA Polymerase α-primase From serva Calf Thymus in Water-in-Oil Microemulsions. Biochim. et Biophys. Acta. 1384: 315-324. 1998.
Bernath et al. In Vitro Compartmentalization by Double emulsions: Sorting and Gene Enrichment by Fluorescence Activated Cell Sorting. Analytical Biochem. 325: 151-157. 2004.
Bertschinger et al. Covalent DNA Display as a Novel Tool for Directed Evolution of Proteins in Vitro. Protein Engineering, Design & Selection. 17: 699-707. 2004.
Bertschinger et al. Selection of Single Domain Binding Proteins by Covalent DNA Display. Protein Engineering, Design & Selection. 20: 57-68. 2007.
Buller et al. Design and Synthesis of a Novel DNA-encoded Chemical Library Using Diels-Alder Cycloadditions. Bioorg. Med. Chem. Lett. 18: 5926-5931. 2008.
Calderone et al. Small-Molecule Diversification from Iterated Branching Reaction Pathways Enabled by DNA-Templated Synthesis. Angew. Chem. Int. Ed. 44: 7383-7386. 2005.

(Continued)

*Primary Examiner* — Tracy Vivlemore
*Assistant Examiner* — Sahana S Kaup
(74) *Attorney, Agent, or Firm* — Cheryl Agris; Agris & von Natzmer LLP

(57) ABSTRACT

A method for making an enriched library comprising specific nucleic acid sequence information allowing to identifying at least one binding entity that binds to at least one target wherein the specific binding entity has been present in an in vitro display library.

13 Claims, 7 Drawing Sheets

Specification includes a Sequence Listing.

(56) References Cited

OTHER PUBLICATIONS

Chee et al. A Diazirine-based Photoaffinity Etoposide Probe for Labeling Topoisomerase II. Bioorg. Med. Chem. 18(2): 830-838. 2010.
Chen et al. Cell-free selection of RNA-binding proteins using in vitro compartmentalization. Nucleic Acids Res. 36: e128. 2008.
Clark et al. Design, Synthesis and Selection of DNA-encoded Small-molecule Libraries. Nature Chem. Biol. 5: 647-654. 2009.
Clark. Selecting Chemicals: The Emerging Utility of DNA-Encoded Libraries. Current Opinion in Chemical Biology. 14:396-403. 2010.
Compton. Nucleic Acid Sequence-Based Amplification. Nature. 350(6303): 91-92. 1991.
Copeland et al. Drug-target Residence Time and Its Implications for Lead Optimization. Nat. Rev. Drug Discov. 5(9): 730-739. 2006.
Czlapinski et al. Nucleic Acid Template-Directed Assembly of Metallosalen-DNA Conjugates. J. Am. Chem. Soc. 123(35): 8618-8619. 2001.
Diehl et al. BEAMing: Single-molecule PCR on Microparticles in Water-in-oil Emulsions. Nat. Methods. 3(7): 551-559. 2006.
Doi et al. Stable: Protein-DNA fusion system for screening of combinatorial protein libraries in vitro. FEBS Lett. 457: 227-230. 1999.
Drabovich et al. Selection of Smart Small-molecule Ligands: The Proof of Principle. Anal. Chem. 81: 490-494. 2009.
Dressman et al. Transforming Single DNA Molecules Into Fluorescent Magnetic Particles for Detection and Enumeration of Genetic Variations. Proc. Natl. Acad. Sci. USA. 100: 8817-8822. 2003.
Ellington et al. In Vitro Selection of RNA Molecules That Bind Specific Ligands. Nature. 346: 818-822. 1990.
Fujimoto et al. Template-Directed Photoreversible Ligation of Deoxyoligonucleotides via 5-Vinyldeoxyuridine. J. Am. Chem. Soc. 122(23): 5646-5647. 2000.
Gartner et al. DNA-Templated Organic Synthesis and Selection of a Library of macrocycles. Science. 305:1601-1605. 2004.
Ghadessy et al. Directed Evolution of Polymerase Function by Compartmentalized Self-replication. Proc. Natl. Acad. Sci. USA 98: 4552-4557. 2001.
Griffiths et al. Miniaturising the Laboratory in Emulsion Droplets. Trends in Biotechnology. 24:395-402. 2006.
Gusev et al. Rolling Circle Amplification: A New Approach to Increase Sensitivity for Immunohistochemistry and Flow Cytometry. Am. J. Path. 159(1): 63-69. 2001.
Hansen et al. A yoctoliter-scale DNA reactor for small-molecule evolution. J. Am. Chem. Soc. 131: 1322-1327. 2009.
Hassan et al. Mapping the Subunit Interface of Ribonucleotide Reductase (RNR) Using Photo Cross-linking. Bioorg. Med. Chem. Lett. 18(22): 5923-5925. 2008.
Kanan et al. Reaction Discovery Enabled by DNA-templated Synthesis and In Vitro Selection. Nature. 431(7008): 545-549. 2004.
Kenrick et al. Bacterial Display Enables Efficient and Quantitative Peptide Affinity Maturation. Protein Eng. Des. Sel. 23:9-17. 2010.
Levy et al. Direct selection of trans-acting ligase ribozymes by in vitro compartmentalization. RNA. 11: 1555-1562. 2005.
Manocci et al. High-throughput Sequencing Allows the Identification of Binding Molecules Isolated from DNA-Encoded Chemical Libraries. Proc. Natl. Acad. Sci. USA. 105: 17671-17675. 2008.
Margulies et al. Genome Sequencing in Microfabricated High-density Picolitre Reactors. Nature. 437: 376-380. 2005.
Mastrobattista, et al. High-Throughput Screening of Enzyme Libraries: In Vitro Evolution of a Beta-Galactosidase by Fluorescence-Activated Sorting of Double Emulsions. Chem Biol. 12: 1291-1300. 2005.
Mays et al. Cyclic Disulfides as Functional Mimics of the Histone Deacetylase Inhibitor FK-228. Tetrahedron Lett. 48(26): 4579-4583. 2007.
Melkko et al. Encoded Self-Assembling Chemical Libraries. Nat. Biotechnol. 2004; 22: 568-574. 2004.
Metzker. Sequencing Technologies—The Next Generation. Nat. Rev. Genetics. 11(1): 31-46. 2010.
Miller et al. Directed evolution by in vitro compartmentalization. Nature Methods 3: 561-570. 2006.
Musyanovych et al. Miniemulsion Droplets as Single Molecule Nanoreactors for Polymerase Chain Reaction. Biomacromolecules. 6(4): 1824-1828. 2005.
Nakano et al. Single-molecule PCR Using Water-in-oil Emulsion. J. Biotech. 102: 117-124. 2003.
Nasal. 4'-(1-Azi-2,2,2-trifluoroethyl)phenylalanine, a Photolabile Carbene-Generating Analogue of Phenylalanine. J. Am. Chem. Soc. 106(24): 7540-7545. 1984.
Ong et al. Directed Evolution of DNA Polymerase, RNA Polymerase and Reverse Transcriptase Activity in a Single Polypeptide. J. Mol. Biol. 361: 537-550. 2006.
Pandurangi et al. Chemistry of Bifunctional Photoprobes II. Chemical and Photochemical Modification of Angiotensin Converting Enzyme Inhibitors: Implications in the Development of Cardiac Radionuclide Imaging Agents. Bioorg. Chem. 25: 77-87. 1997.
Poulin-Kerstien et al. DNA-Templated Dimerization of Hairpin Polyamides. J. Am. Chem. Soc. 125(51): 15811-15821. 2003.
Roberts et al. RNA-peptide fusions for the in vitro selection of peptides and proteins. Proc. Natl. Acad. Sci. USA 94: 12297-12302. 1997.
Rondelez et al. Microfabricated Arrays of Femtoliter Chambers Allow Single Molecule Enzymology. Nat. Biotech. 23(3): 361-365. 2005.
Salom et al. Characterization of Gramicidin A in an Inverted Micellar Environment. A Combined High-Performance Liquid Chromatographic and Spectroscopic Study. Biochem. 31(34): 8072-8079. 1992.
Saurabh et al. Compartmentalized Linkage of Genes Encoding Interacting Protein Pairs Proteonomics. 11:1335-1339. 2011.
Schena et al. Quantitative Monitoring of Gene Expression Patterns with a Complementary DNA Microarray. Science. 270(5235): 467-470. 1995.
Sepp et al. Cell-free Selection of Zinc Finger DNA-binding Proteins Using In Vitro Compartmentalization. J. Mol. Biol. 354: 212-219. 2005.
Tang et al. Proline-Modified DNA as Catalyst of the Aldol Reaction. Angew. Chem. Int. Ed. 46: 7297-7300. 2007.
Tawfik et al. Man-Made Cell-Like Compartments for Molecular Evolution. Nat. Biotechnol. 16: 652-656. 1988.
Tay et al. Selection of Bacteriophage Lambda Integrases with Altered Recombination Specificity by In Vitro Compartmentalization. Nucleic Acids Res. 38: e25. 2010.
U.S. Appl. No. 13/636,668, filed Sep. 21, 2012 and published as 20130288929 published Oct. 31, 2013, First Office Action dated Jan. 3, 2014.
U.S. Appl. No. 13/636,668, filed Sep. 21, 2012 and published as 20130288929 published Oct. 31, 2013, Interview Summary dated Apr. 16, 2014.
U.S. Appl. No. 13/636,668, filed Sep. 21, 2012 and published as 20130288929 published Oct. 31, 2013, Second Office Action dated Jun. 16, 2014.
U.S. Appl. No. 13/636,668, filed Sep. 21, 2012 and published as 20130288929 published Oct. 31, 2013, Advisory Office Action dated Oct. 3, 2014.
U.S. Appl. No. 13/636,668, filed Sep. 21, 2012 and published as 20130288929 published Oct. 31, 2013, Third Office Action dated Oct. 15, 2015.
U.S. Appl. No. 13/636,668, filed Sep. 21, 2012 and published as 20130288929 published Oct. 31, 2013, Fourth Office Action dated May 31, 2016.
PCT application No. PCT/EP2011/065117, filed Sep. 1, 2011, published as WO 2012041633 A1, published Apr. 5, 2012, International Search Report dated Nov. 17, 2011.
PCT application No. PCT/EP2011/065117, filed Sep. 1, 2011, published as WO 2012041633 A1, published Apr. 5, 2012, Written Opinion dated Mar. 27, 2013.
PCT application No. PCT/EP2011/065117, filed Sep. 1, 2011, published as WO 2012041633 A1, published Apr. 5, 2012, International Preliminary Report on Patentability dated Apr. 2, 2013.
CA Patent Application and Pub. No. 2,808,656, filed Sep. 1, 2011, published Apr. 5, 2012, Office Action dated Jun. 15, 2017.

(56) References Cited

OTHER PUBLICATIONS

CA Patent Application and Pub. No. No. 2,808,656, filed Sep. 1, 2011, published Apr. 5, 2012, response to Office Action, submitted Dec. 11, 2017.
CN Patent Application No. 201180046388, filed Sep. 1, 2011, pub. No. CN 103119165, published May 22, 2013, patent issued Apr. 12, 2017, 1st Office Action dated Mar. 31, 2014 (original and English translation).
CN Patent Application No. 201180046388, filed Sep. 1, 2011, pub. No. CN 103119165, published May 22, 2013, patent issued Apr. 12, 2017, Response to 1st Office Action submitted Jul. 28, 2014 (English translation).
CN Patent Application No. 201180046388, filed Sep. 1, 2011, pub. No. CN 103119165, published May 22, 2013, patent issued Apr. 12, 2017, 2nd Office Action dated Nov. 25, 2014 (original and English translation).
CN Patent Application No. 201180046388, filed Sep. 1, 2011, pub. No. CN 103119165, published May 22, 2013, patent issued Apr. 12, 2017, Response to 2nd Office Action submitted Apr. 10, 2015 (English translation).
CN Patent Application No. 201180046388, filed Sep. 1, 2011, pub. No. CN 103119165, published May 22, 2013, patent issued Apr. 12, 2017, 3rd Office Action dated Aug. 21, 2015 (original and English translation).
CN Patent Application No. 201180046388, filed Sep. 1, 2011, pub. No. CN 103119165, published May 22, 2013, patent issued Apr. 12, 2017, Response to 3rd Office Action submitted Dec. 29, 2015 (English translation).
CN Patent Application No. 201180046388, filed Sep. 1, 2011, pub. No. CN 103119165, published May 22, 2013, patent issued Apr. 12, 2017, 4th Office Action dated May 4, 2016 (original and English translation).
CN Patent Application No. 201180046388, filed Sep. 1, 2011, pub. No. CN 103119165, published May 22, 2013, patent issued Apr. 12, 2017, Response to 4th Office Action submitted Sep. 8, 2016 (English translation).
CN Patent Application No. 201180046388, filed Sep. 1, 2011, pub. No. CN 103119165, published May 22, 2013, patent issued Apr. 12, 2017, intention to grant dated Jan. 9, 2017 (English translation).
EP Patent Application No. 11749853, filed Sep. 1, 2011, pub. No. EP 2622073 A1, published Aug. 7, 2013, Reply to communication pursuant to Rule 161 (1) and 162 dated May 13, 2013 (response to PCT Written Opinion and invitation to amend claims), submitted Nov. 14, 2013.
EP Patent Application No. 11749853, filed Sep. 1, 2011, pub. No. EP 2622073 A1, published Aug. 7, 2013, 1st Communication pursuant to Article 94(3) EPC dated Feb. 11, 2015.
EP Patent Application No. 11749853, filed Sep. 1, 2011, pub. No. EP 2622073 A1, published Aug. 7, 2013, Response to Communication pursuant to Article 94(3) EPC, submitted Aug. 14, 2015.
EP Patent Application No. 11749853, filed Sep. 1, 2011, pub. No. EP 2622073 A1, published Aug. 7, 2013, 2nd Communication pursuant to Article 94(3) EPC dated Oct. 23, 2015.
EP Patent Application No. 11749853, filed Sep. 1, 2011, pub. No. EP 2622073 A1, published Aug. 7, 2013, Response to 2nd Communication pursuant to Article 94(3) EPC submitted Apr. 25, 2016.
EP Patent Application No. 11749853, filed Sep. 1, 2011, pub. No. EP 2622073 A1, published Aug. 7, 2013, 3rd Communication pursuant to Article 94(3) EPC dated May 25, 2016.
EP Patent Application No. 11749853, filed Sep. 1, 2011, pub. No. EP 2622073 A1, published Aug. 7, 2013, Response to 3rd Communication pursuant to Article 94(3) EPC submitted Nov. 29, 2016.
EP Patent Application No. 11749853, filed Sep. 1, 2011, pub. No. EP 2622073 A1, published Aug. 7, 2013, intention to grant dated Aug. 8, 2017.
IL Patent Application No. 22469413, filed Feb. 13, 2013, pub. No. IL 224694, published Jul. 31, 2013,1st Office Action dated Sep. 21, 2016 (translation).
IL Patent Application No. 22469413, filed Feb. 13, 2013, pub. No. IL 224694, published Jul. 31, 2013, summary of response filed Mar. 13, 2017.
JP Patent Application No. 201353066, filed Sep. 1, 2011, pub. No. JP 2013540440 A, published Nov. 7, 2013,1st Office Action dated Aug. 11, 2015 (original and translation).
JP Patent Application No. 201353066, filed Sep. 1, 2011, pub. No. JP 2013540440 A, published Nov. 7, 2013, response to 1st Office Action submitted Feb. 18, 2016 (translation).
JP Patent Application No. 201353066, filed Sep. 1, 2011, pub. No. JP 2013540440 A, published Nov. 7, 2013, Decision of final rejection dated Jul. 26, 2016 (original and translation).
JP Patent Application No. 201353066, filed Sep. 1, 2011, pub. No. JP 2013540440 A, published Nov. 7, 2013, Written amendment, submitted Nov. 28, 2016 (original and translation).
JP Patent Application No. 201353066, filed Sep. 1, 2011, pub. No. JP 2013540440 A, published Nov. 7, 2013, Report of Reconsideration dated Jan. 18, 2017(original and translation).
JP Patent Application No. 201353066, filed Sep. 1, 2011, pub. No. JP 2013540440 A, published Nov. 7, 2013, Written Argument dated May 11, 2017(original and translation).
JP Patent Application No. 201353066, filed Sep. 1, 2011, pub. No. JP 2013540440 A, published Nov. 7, 2013, Office Action dated Feb. 17, 2017 (translation).
JP Patent Application No. 201353066, filed Sep. 1, 2011, pub. No. JP 2013540440 A, published Nov. 7, 2013, response to Report of Reconsideration, submitted May 11, 2017 (original and translation).
JP Patent Application No. 2016229846, filed Nov. 28, 2016, pub. No. JP 2017060513 A, published Mar. 30, 2017, divisional application of JP Patent Application No. 201353066, filed Sep. 1, 2011, pub. No. JP 2013540440 A, published Nov. 7, 2013, claims as filed (original and translation).
JP Patent Application No. 2016229846, filed Nov. 28, 2016, pub. No. JP 2017060513 A, published Mar. 30, 2017, divisional application of JP Patent Application No. 201353066, filed Sep. 1, 2011, pub. No. JP 2013540440 A, published Nov. 7, 2013, statement submitted by Applicant, dated Dec. 28, 2016 (original and translation).
JP Patent Application No. 2016229846, filed Nov. 28, 2016, pub. No. JP 2017060513 A, published Mar. 30, 2017, divisional application of JP Patent Application No. 201353066, filed Sep. 1, 2011, pub. No. JP 2013540440 A, published Nov. 7, 2013, Reasons for Refusal dated Oct. 17, 2017(original and translation).
CA Patent Application and Pub. No. 2,808,656, filed Sep. 1, 2011, published Apr. 5, 2012, Office Action dated May 7, 2008.
CA Patent Application and Pub. No. No. 2,808,656, filed Sep. 1, 2011, published Apr. 5, 2012, response to Office Action, submitted Nov. 7, 2008.
IN Patent Application No. 1781/DELNP/2013, filed Feb. 27, 2013, published Oct. 24, 2014, 1st Office Action dated Jun. 14, 2018.

* cited by examiner

Illustrative example of the principle in ECC

Immobilized drug target

The Low range DNA marker (Fermentas) was loaded in the lane M. In lane 1, PCR product derived from the binding reaction without pre-incubation with biotin was loaded. In lane 2, PCR product derived from the binding reaction with pre-incubation with biotin was loaded.

Figure 5

| Condition | Spiked (1:1000) | Preincubation w biotin | # Total counts | # Biotin_yR counts | % Biotin_yR | Fold enrichment |
|---|---|---|---|---|---|---|
| A | Yes | No | 6339 | 2385 | 37.62 | 376 |
| A | Yes | No | 7032 | 2250 | 32.00 | 320 |
| B | Yes | Yes | 6897 | 21 | 0.30 | 3 |
| B | Yes | Yes | 7195 | 52 | 0.72 | 7 |
| C | No | No | 5750 | 1 | 0.02 | 0 |
| C | No | No | 6425 | 3 | 0.05 | 0 |

Results from DNA sequencing

Figure 7

| Sample | Library | BSB_yR spike | Target | Target conc (nM) | Target pre-incubated w 1 uM BSB | Emulsion force (rpm) | Dissociation time (min) | Total number of reads | Higest counts | 2nd higest counts | Counts for BSB_yR | Frequency (BSB_yR) | Fold enrichment |
|---|---|---|---|---|---|---|---|---|---|---|---|---|---|
| 1 | Lib01651 | 0.000005 | CA II | 10 |   | 5500 | 2 | 7808 | 54 | 24 | 54 | 0.0069 | 1383 |
| 2 | Lib01651 | 0.000005 | CA II | 10 | 1 | 5500 | 2 | 7970 | 17 | 15 | 0 | <0.0001 | NA |
| 3 | Lib01651 | 0.000005 | CA II | 10 |   | 5500 | 30 | 10470 | 15 | 14 | 0 | <0.0001 | NA |
| 4 | Lib01651 | 0.000005 | CA II | 10 | 1 | 5500 | 30 | 7053 | 18 | 15 | 0 | <0.0001 | NA |
| 5 | Lib01651 | 0.000005 | CA II | 10 |   | NA | NA | 15864 | 15 | 12 | 0 | <0.0001 | NA |

Results from DNA sequencing

SEQUENCE LISTING

```
<160> NUMBER OF SEQ ID NOS: 78

<210> SEQ ID NO 1
<211> LENGTH: 191
<212> TYPE: DNA
<213> ORGANISM: Artificial Sequence
<220> FEATURE:
<221> NAME/KEY: source
<222> LOCATION: 1..191
<223> OTHER INFORMATION: /mol_type="DNA"
      /note="Primer"
      /organism="Artificial Sequence"

<400> SEQUENCE: 1
cgctaatggt ccctggcagt ctccttagcg gaccgactcc tgctcgaaga caacggtgtt    60
ttacaccgtt gtcttcgagc tgtacctgcg caagtgcgtt ttacgcactt gcgcaggtac   120
tgtgcatcga caagaccgtt ttacggtctt gtcgatgcac tggagtcggt cctgttcgat   180
cttgggcgta t                                                        191

<210> SEQ ID NO 2
<211> LENGTH: 20
<212> TYPE: DNA
<213> ORGANISM: Artificial Sequence
<220> FEATURE:
<221> NAME/KEY: source
<222> LOCATION: 1..20
<223> OTHER INFORMATION: /mol_type="DNA"
      /note="Primer"
      /organism="Artificial Sequence"

<400> SEQUENCE: 2
atacgcccaa gatcgaacag                                                20

<210> SEQ ID NO 3
<211> LENGTH: 18
<212> TYPE: DNA
<213> ORGANISM: Artificial Sequence
<220> FEATURE:
<221> NAME/KEY: source
<222> LOCATION: 1..18
<223> OTHER INFORMATION: /mol_type="DNA"
      /note="Primer"
      /organism="Artificial Sequence"

<400> SEQUENCE: 3
tggtccctgg cagtctcc                                                  18

<210> SEQ ID NO 4
<211> LENGTH: 60
<212> TYPE: DNA
<213> ORGANISM: Artificial Sequence
<220> FEATURE:
<221> NAME/KEY: source
<222> LOCATION: 1..60
<223> OTHER INFORMATION: /mol_type="DNA"
      /note="Primer"
      /organism="Artificial Sequence"

<400> SEQUENCE: 4
ctgttcgatc ttgggcgtat gagaagagcc agaaacgtgg cttcaggcac caaggaagac    60
```

<210> SEQ ID NO 5
<211> LENGTH: 59
<212> TYPE: DNA
<213> ORGANISM: Artificial Sequence
<220> FEATURE:
<221> NAME/KEY: source
<222> LOCATION: 1..59
<223> OTHER INFORMATION: /mol_type="DNA"
      /note="Primer"
      /organism="Artificial Sequence"

<400> SEQUENCE: 5
gccttgccag cccgctcagg caagtcttac agccgatcag tcttccttgg tgcctgaag        59

<210> SEQ ID NO 6
<211> LENGTH: 20
<212> TYPE: DNA
<213> ORGANISM: Artificial Sequence
<220> FEATURE:
<221> NAME/KEY: source
<222> LOCATION: 1..20
<223> OTHER INFORMATION: /mol_type="DNA"
      /note="Primer"
      /organism="Artificial Sequence"

<400> SEQUENCE: 6
ctgttcgatc ttgggcgtat        20

<210> SEQ ID NO 7
<211> LENGTH: 19
<212> TYPE: DNA
<213> ORGANISM: Artificial Sequence
<220> FEATURE:
<221> NAME/KEY: source
<222> LOCATION: 1..19
<223> OTHER INFORMATION: /mol_type="DNA"
      /note="Primer"
      /organism="Artificial Sequence"

<400> SEQUENCE: 7
gccttgccag cccgctcag        19

<210> SEQ ID NO 8
<211> LENGTH: 19
<212> TYPE: DNA
<213> ORGANISM: Artificial Sequence
<220> FEATURE:
<221> NAME/KEY: source
<222> LOCATION: 1..19
<223> OTHER INFORMATION: /mol_type="DNA"
      /note="Primer"
      /organism="Artificial Sequence"

<400> SEQUENCE: 8
gccttgccag cccgctcag        19

<210> SEQ ID NO 9
<211> LENGTH: 16
<212> TYPE: DNA
<213> ORGANISM: Artificial Sequence
<220> FEATURE:
<221> NAME/KEY: source
<222> LOCATION: 1..16
<223> OTHER INFORMATION: /mol_type="DNA"
      /note="Primer"
      /organism="Artificial Sequence"

<400> SEQUENCE: 9
tggtccctgg cagtct                                              16

<210> SEQ ID NO 10
<211> LENGTH: 12
<212> TYPE: DNA
<213> ORGANISM: Artificial Sequence
<220> FEATURE:
<221> NAME/KEY: source
<222> LOCATION: 1..12
<223> OTHER INFORMATION: /mol_type="DNA"
      /note="Primer"
      /organism="Artificial Sequence"

<400> SEQUENCE: 10
gaacaggacc ga                                                  12

<210> SEQ ID NO 11
<211> LENGTH: 20
<212> TYPE: DNA
<213> ORGANISM: Artificial Sequence
<220> FEATURE:
<221> NAME/KEY: source
<222> LOCATION: 1..20
<223> OTHER INFORMATION: /mol_type="DNA"
      /note="Primer"
      /organism="Artificial Sequence"

<400> SEQUENCE: 11
ctgttcgatc ttgggcgtat                                          20

<210> SEQ ID NO 12
<211> LENGTH: 18
<212> TYPE: DNA
<213> ORGANISM: Artificial Sequence
<220> FEATURE:
<221> NAME/KEY: source
<222> LOCATION: 1..18
<223> OTHER INFORMATION: /mol_type="DNA"
      /note="Primer"
      /organism="Artificial Sequence"

<400> SEQUENCE: 12
acgcccaaga tcgaacag                                            18

<210> SEQ ID NO 13
<211> LENGTH: 61
<212> TYPE: DNA
<213> ORGANISM: Artificial Sequence
<220> FEATURE:
<221> NAME/KEY: source
<222> LOCATION: 1..61
<223> OTHER INFORMATION: /mol_type="DNA"
      /note="Primer"
      /organism="Artificial Sequence"

<400> SEQUENCE: 13
gccttgccag cccgctcagg ggaaggacgt tggtgtagaa gcgttcactt ggtggaagta    60
t                                                              61

<210> SEQ ID NO 14
<211> LENGTH: 20
<212> TYPE: DNA
<213> ORGANISM: Artificial Sequence
<220> FEATURE:
<221> NAME/KEY: source
<222> LOCATION: 1..20
<223> OTHER INFORMATION: /mol_type="DNA"
      /note="Primer"
      /organism="Artificial Sequence"

<400> SEQUENCE: 14
acttccacca agtgaacgct                                                    20

<210> SEQ ID NO 15
<211> LENGTH: 60
<212> TYPE: DNA
<213> ORGANISM: artificial sequences
<220> FEATURE:
<221> NAME/KEY: source
<222> LOCATION: 1..60
<223> OTHER INFORMATION: /mol_type="DNA"
      /note="Primer"
      /organism="artificial sequences"

<400> SEQUENCE: 15
ctgttcgatc ttgggcgtat tgttttagct gccccaactc cttcaggcac caaggaagac        60

<210> SEQ ID NO 16
<211> LENGTH: 20
<212> TYPE: DNA
<213> ORGANISM: artificial sequences
<220> FEATURE:
<221> NAME/KEY: source
<222> LOCATION: 1..20
<223> OTHER INFORMATION: /mol_type="DNA"
      /note="Primer"
      /organism="artificial sequences"

<400> SEQUENCE: 16
gcaagtctta cagccgatca                                                    20

<210> SEQ ID NO 17
<211> LENGTH: 18
<212> TYPE: DNA
<213> ORGANISM: artificial sequences
<220> FEATURE:
<221> NAME/KEY: source
<222> LOCATION: 1..18
<223> OTHER INFORMATION: /mol_type="DNA"
      /note="Primer"
      /organism="artificial sequences"

<400> SEQUENCE: 17
tggtccctgg cagtctcc                                                      18

<210> SEQ ID NO 18
<211> LENGTH: 50
<212> TYPE: DNA
<213> ORGANISM: artificial sequences
<220> FEATURE:
<221> NAME/KEY: source
<222> LOCATION: 1..50
<223> OTHER INFORMATION: /mol_type="DNA"
      /note="Primer"
      /organism="artificial sequences"

<400> SEQUENCE: 18
cctatcccct gtgtgccttg gcagtctcag gtcttccttg gtgcctgaag                    50

<210> SEQ ID NO 19
<211> LENGTH: 52
<212> TYPE: DNA
<213> ORGANISM: artificial sequences
<220> FEATURE:
<221> NAME/KEY: source
<222> LOCATION: 1..52
<223> OTHER INFORMATION: /mol_type="DNA"
      /note="Primer"

/organism="artificial sequences"

<400> SEQUENCE: 19
ccatctcatc cctgcgtgtc tccgactcag aggttggtcc ctggcagtct cc    52

<210> SEQ ID NO 20
<211> LENGTH: 52
<212> TYPE: DNA
<213> ORGANISM: artificial sequences
<220> FEATURE:
<221> NAME/KEY: source
<222> LOCATION: 1..52
<223> OTHER INFORMATION: /mol_type="DNA"
     /note="PRIMER"
     /organism="artificial sequences"

<400> SEQUENCE: 20
ccatctcatc cctgcgtgtc tccgactcag atcgtggtcc ctggcagtct cc    52

<210> SEQ ID NO 21
<211> LENGTH: 52
<212> TYPE: DNA
<213> ORGANISM: artificial sequences
<220> FEATURE:
<221> NAME/KEY: source
<222> LOCATION: 1..52
<223> OTHER INFORMATION: /mol_type="DNA"
     /note="Primer"
     /organism="artificial sequences"

<400> SEQUENCE: 21
ccatctcatc cctgcgtgtc tccgactcag atgctggtcc ctggcagtct cc    52

<210> SEQ ID NO 22
<211> LENGTH: 52
<212> TYPE: DNA
<213> ORGANISM: artificial sequences
<220> FEATURE:
<221> NAME/KEY: source
<222> LOCATION: 1..52
<223> OTHER INFORMATION: /mol_type="DNA"
     /note="Primer"
     /organism="artificial sequences"

<400> SEQUENCE: 22
ccatctcatc cctgcgtgtc tccgactcag cacttggtcc ctggcagtct cc    52

<210> SEQ ID NO 23
<211> LENGTH: 52
<212> TYPE: DNA
<213> ORGANISM: artificial sequences
<220> FEATURE:
<221> NAME/KEY: source
<222> LOCATION: 1..52
<223> OTHER INFORMATION: /mol_type="DNA"
     /note="Primer"
     /organism="artificial sequences"

<400> SEQUENCE: 23
ccatctcatc cctgcgtgtc tccgactcag cagatggtcc ctggcagtct cc    52

<210> SEQ ID NO 24
<211> LENGTH: 52
<212> TYPE: DNA
<213> ORGANISM: artificial sequences
<220> FEATURE:
<221> NAME/KEY: source
<222> LOCATION: 1..52
<223> OTHER INFORMATION: /mol_type="DNA"

```
        /note="Primer"
        /organism="artificial sequences"

<400> SEQUENCE: 24
ccatctcatc cctgcgtgtc tccgactcag ccattggtcc ctggcagtct cc        52

<210> SEQ ID NO 25
<211> LENGTH: 18
<212> TYPE: DNA
<213> ORGANISM: artificial sequences
<220> FEATURE:
<221> NAME/KEY: source
<222> LOCATION: 1..18
<223> OTHER INFORMATION: /mol_type="DNA"
        /note="Primer"
        /organism="artificial sequences"

<400> SEQUENCE: 25
tggtccctgg cagtctcc                                              18

<210> SEQ ID NO 26
<211> LENGTH: 36
<212> TYPE: DNA
<213> ORGANISM: artificial sequences
<220> FEATURE:
<221> NAME/KEY: source
<222> LOCATION: 1..36
<223> OTHER INFORMATION: /mol_type="DNA"
        /note="Primer"
        /organism="artificial sequences"

<400> SEQUENCE: 26
caccacgatg gcaatgcatt cttcgctgcc attctg                          36

<210> SEQ ID NO 27
<211> LENGTH: 20
<212> TYPE: DNA
<213> ORGANISM: artificial sequences
<220> FEATURE:
<221> NAME/KEY: source
<222> LOCATION: 1..20
<223> OTHER INFORMATION: /mol_type="DNA"
        /note="Primer"
        /organism="artificial sequences"

<400> SEQUENCE: 27
cgatgtcctg aggtggaagt                                            20

<210> SEQ ID NO 28
<211> LENGTH: 40
<212> TYPE: DNA
<213> ORGANISM: artificial sequences
<220> FEATURE:
<221> NAME/KEY: source
<222> LOCATION: 1..40
<223> OTHER INFORMATION: /mol_type="DNA"
        /note="Primer"
        /organism="artificial sequences"

<400> SEQUENCE: 28
ggcaagtgat tgtccatgtg catgagaaga ggcccacatt                      40

<210> SEQ ID NO 29
<211> LENGTH: 20
<212> TYPE: DNA
<213> ORGANISM: artificial sequences
<220> FEATURE:
<221> NAME/KEY: source
<222> LOCATION: 1..20
```

```
<223> OTHER INFORMATION: /mol_type="DNA"
      /note="Primer"
      /organism="artificial sequences"

<400> SEQUENCE: 29
cacatggaca atcacttgcc                                              20

<210> SEQ ID NO 30
<211> LENGTH: 20
<212> TYPE: DNA
<213> ORGANISM: artificial sequences
<220> FEATURE:
<221> NAME/KEY: source
<222> LOCATION: 1..20
<223> OTHER INFORMATION: /mol_type="DNA"
      /note="Primer"
      /organism="artificial sequences"

<400> SEQUENCE: 30
aatgtgggcc tcttctcatg                                              20

<210> SEQ ID NO 31
<211> LENGTH: 18
<212> TYPE: DNA
<213> ORGANISM: artificial sequences
<220> FEATURE:
<221> NAME/KEY: source
<222> LOCATION: 1..18
<223> OTHER INFORMATION: /mol_type="DNA"
      /note="Primer"
      /organism="artificial sequences"

<400> SEQUENCE: 31
tccacatcct ccagttca                                                18

<210> SEQ ID NO 32
<211> LENGTH: 40
<212> TYPE: DNA
<213> ORGANISM: artificial sequences
<220> FEATURE:
<221> NAME/KEY: source
<222> LOCATION: 1..40
<223> OTHER INFORMATION: /mol_type="DNA"
      /note="Primer"
      /organism="artificial sequences"

<400> SEQUENCE: 32
acttccacct caggacatcg agctggagct tgctgttagc                         40

<210> SEQ ID NO 33
<211> LENGTH: 40
<212> TYPE: DNA
<213> ORGANISM: artificial sequences
<220> FEATURE:
<221> NAME/KEY: source
<222> LOCATION: 1..40
<223> OTHER INFORMATION: /mol_type="DNA"
      /note="Primer"
      /organism="artificial sequences"

<400> SEQUENCE: 33
aggttcgctc cctccttaag tcaggaggat gtgacaccaa                         40

<210> SEQ ID NO 34
<211> LENGTH: 40
<212> TYPE: DNA
<213> ORGANISM: artificial sequences
<220> FEATURE:
<221> NAME/KEY: source
```

```
<222> LOCATION: 1..40
<223> OTHER INFORMATION: /mol_type="DNA"
      /note="Primer"
      /organism="artificial sequences"

<400> SEQUENCE: 34
cgatgtcctg aggtggaagt tgaactggag gatgtggaca                              40

<210> SEQ ID NO 35
<211> LENGTH: 40
<212> TYPE: DNA
<213> ORGANISM: artificial sequences
<220> FEATURE:
<221> NAME/KEY: source
<222> LOCATION: 1..40
<223> OTHER INFORMATION: /mol_type="DNA"
      /note="Primer"
      /organism="artificial sequences"

<400> SEQUENCE: 35
cttaaggagg gagcgaacct gctaacagca agctccagct                              40

<210> SEQ ID NO 36
<211> LENGTH: 20
<212> TYPE: DNA
<213> ORGANISM: artificial sequences
<220> FEATURE:
<221> NAME/KEY: source
<222> LOCATION: 1..20
<223> OTHER INFORMATION: /mol_type="DNA"
      /note="Primer"
      /organism="artificial sequences"

<400> SEQUENCE: 36
ttggtgtcac atcctcctga                                                   20

<210> SEQ ID NO 37
<211> LENGTH: 20
<212> TYPE: DNA
<213> ORGANISM: artificial sequences
<220> FEATURE:
<221> NAME/KEY: source
<222> LOCATION: 1..20
<223> OTHER INFORMATION: /mol_type="DNA"
      /note="Primer"
      /organism="artificial sequences"

<400> SEQUENCE: 37
atgaaagacg tggccattgc                                                   20

<210> SEQ ID NO 38
<211> LENGTH: 50
<212> TYPE: DNA
<213> ORGANISM: artificial sequences
<220> FEATURE:
<221> NAME/KEY: source
<222> LOCATION: 1..50
<223> OTHER INFORMATION: /mol_type="DNA"
      /note="Primer"
      /organism="artificial sequences"
<220> FEATURE:
<221> NAME/KEY: misc_feature
<222> LOCATION: 41

<400> SEQUENCE: 38
ctgacatggt ccctggcagt ctcctgtcag gaccgactcc gctcgaagac                   50

<210> SEQ ID NO 39
<211> LENGTH: 40
```

```
<212> TYPE: DNA
<213> ORGANISM: artificial sequences
<220> FEATURE:
<221> NAME/KEY: source
<222> LOCATION: 1..40
<223> OTHER INFORMATION: /mol_type="DNA"
      /note="Primer"
      /organism="artificial sequences"

<400> SEQUENCE: 39
ctatcggttt taccgatagg tcttcgagct gtacctgcgc                              40

<210> SEQ ID NO 40
<211> LENGTH: 40
<212> TYPE: DNA
<213> ORGANISM: artificial sequences
<220> FEATURE:
<221> NAME/KEY: source
<222> LOCATION: 1..40
<223> OTHER INFORMATION: /mol_type="DNA"
      /note="Primer"
      /organism="artificial sequences"

<400> SEQUENCE: 40
agctaggttt tacctagctg cgcaggtact gtgcatcgac                              40

<210> SEQ ID NO 41
<211> LENGTH: 40
<212> TYPE: DNA
<213> ORGANISM: artificial sequences
<220> FEATURE:
<221> NAME/KEY: source
<222> LOCATION: 1..40
<223> OTHER INFORMATION: /mol_type="DNA"
      /note="Primer"
      /organism="artificial sequences"

<400> SEQUENCE: 41
ctatcggttt taccgatagg tcgatgcact ggagtcggtc                              40

<210> SEQ ID NO 42
<211> LENGTH: 18
<212> TYPE: DNA
<213> ORGANISM: artificial sequences
<220> FEATURE:
<221> NAME/KEY: source
<222> LOCATION: 1..18
<223> OTHER INFORMATION: /mol_type="DNA"
      /note="Primer"
      /organism="artificial sequences"

<400> SEQUENCE: 42
cttatgctgg cagtttca                                                     18

<210> SEQ ID NO 43
<211> LENGTH: 40
<212> TYPE: DNA
<213> ORGANISM: artificial sequences
<220> FEATURE:
<221> NAME/KEY: source
<222> LOCATION: 1..40
<223> OTHER INFORMATION: /mol_type="DNA"
      /note="Primer"
      /organism="artificial sequences"

<400> SEQUENCE: 43
acttccacct caggacatcg agctggagct tgctgttagc                              40

<210> SEQ ID NO 44
```

-continued

```
<211> LENGTH: 40
<212> TYPE: DNA
<213> ORGANISM: artificial sequences
<220> FEATURE:
<221> NAME/KEY: source
<222> LOCATION: 1..40
<223> OTHER INFORMATION: /mol_type="DNA"
      /note="Primer"
      /organism="artificial sequences"

<400> SEQUENCE: 44
aggttcgctc cctccttaag ccagcagtgg taattcgaca                              40

<210> SEQ ID NO 45
<211> LENGTH: 40
<212> TYPE: DNA
<213> ORGANISM: artificial sequences
<220> FEATURE:
<221> NAME/KEY: source
<222> LOCATION: 1..40
<223> OTHER INFORMATION: /mol_type="DNA"
      /note="Primer"
      /organism="artificial sequences"

<400> SEQUENCE: 45
cgatgtcctg aggtggaagt tgaaactgcc agcataagga                              40

<210> SEQ ID NO 46
<211> LENGTH: 40
<212> TYPE: DNA
<213> ORGANISM: artificial sequences
<220> FEATURE:
<221> NAME/KEY: source
<222> LOCATION: 1..40
<223> OTHER INFORMATION: /mol_type="DNA"
      /note="Primer"
      /organism="artificial sequences"

<400> SEQUENCE: 46
cttaaggagg gagcgaacct gctaacagca agctccagct                              40

<210> SEQ ID NO 47
<211> LENGTH: 20
<212> TYPE: DNA
<213> ORGANISM: artificial sequences
<220> FEATURE:
<221> NAME/KEY: source
<222> LOCATION: 1..20
<223> OTHER INFORMATION: /mol_type="DNA"
      /note="Primer"
      /organism="artificial sequences"

<400> SEQUENCE: 47
tgtcgaatta ccactgctgg                                                   20

<210> SEQ ID NO 48
<211> LENGTH: 50
<212> TYPE: DNA
<213> ORGANISM: artificial sequences
<220> FEATURE:
<221> NAME/KEY: source
<222> LOCATION: 1..50
<223> OTHER INFORMATION: /mol_type="DNA"
      /note="Primer"
      /organism="artificial sequences"

<400> SEQUENCE: 48
cctatcccct gtgtgccttg gcagtctcag cgatgtcctg aggtggaagt                   50
```

```
<210> SEQ ID NO 49
<211> LENGTH: 52
<212> TYPE: DNA
<213> ORGANISM: artificial sequences
<220> FEATURE:
<221> NAME/KEY: source
<222> LOCATION: 1..52
<223> OTHER INFORMATION: /mol_type="DNA"
      /note="Primer"
      /organism="artificial sequences"

<400> SEQUENCE: 49
ccatctcatc cctgcgtgtc tccgactcag aacctggtcc ctggcagtct cc          52

<210> SEQ ID NO 50
<211> LENGTH: 52
<212> TYPE: DNA
<213> ORGANISM: artificial sequences
<220> FEATURE:
<221> NAME/KEY: source
<222> LOCATION: 1..52
<223> OTHER INFORMATION: /mol_type="DNA"
      /note="Primer"
      /organism="artificial sequences"

<400> SEQUENCE: 50
ccatctcatc cctgcgtgtc tccgactcag aaggtggtcc ctggcagtct cc          52

<210> SEQ ID NO 51
<211> LENGTH: 52
<212> TYPE: DNA
<213> ORGANISM: artificial sequences
<220> FEATURE:
<221> NAME/KEY: source
<222> LOCATION: 1..52
<223> OTHER INFORMATION: /mol_type="DNA"
      /note="Primer"
      /organism="artificial sequences"

<400> SEQUENCE: 51
ccatctcatc cctgcgtgtc tccgactcag acactggtcc ctggcagtct cc          52

<210> SEQ ID NO 52
<211> LENGTH: 52
<212> TYPE: DNA
<213> ORGANISM: artificial sequences
<220> FEATURE:
<221> NAME/KEY: source
<222> LOCATION: 1..52
<223> OTHER INFORMATION: /mol_type="DNA"
      /note="Primer"
      /organism="artificial sequences"

<400> SEQUENCE: 52
ccatctcatc cctgcgtgtc tccgactcag actgtggtcc ctggcagtct cc          52

<210> SEQ ID NO 53
<211> LENGTH: 52
<212> TYPE: DNA
<213> ORGANISM: artificial sequences
<220> FEATURE:
<221> NAME/KEY: source
<222> LOCATION: 1..52
<223> OTHER INFORMATION: /mol_type="DNA"
      /note="Primer"
      /organism="artificial sequences"

<400> SEQUENCE: 53
ccatctcatc cctgcgtgtc tccgactcag agagtggtcc ctggcagtct cc          52
```

<210> SEQ ID NO 54
<211> LENGTH: 52
<212> TYPE: DNA
<213> ORGANISM: artificial sequences
<220> FEATURE:
<221> NAME/KEY: source
<222> LOCATION: 1..52
<223> OTHER INFORMATION: /mol_type="DNA"
      /note="Primer"
      /organism="artificial sequences"

<400> SEQUENCE: 54
ccatctcatc cctgcgtgtc tccgactcag agcatggtcc ctggcagtct cc        52

<210> SEQ ID NO 55
<211> LENGTH: 52
<212> TYPE: DNA
<213> ORGANISM: artificial sequences
<220> FEATURE:
<221> NAME/KEY: source
<222> LOCATION: 1..52
<223> OTHER INFORMATION: /mol_type="DNA"
      /note="Primer"
      /organism="artificial sequences"

<400> SEQUENCE: 55
ccatctcatc cctgcgtgtc tccgactcag agtctggtcc ctggcagtct cc        52

<210> SEQ ID NO 56
<211> LENGTH: 52
<212> TYPE: DNA
<213> ORGANISM: artificial sequences
<220> FEATURE:
<221> NAME/KEY: source
<222> LOCATION: 1..52
<223> OTHER INFORMATION: /mol_type="DNA"
      /note="Primer"
      /organism="artificial sequences"

<400> SEQUENCE: 56
ccatctcatc cctgcgtgtc tccgactcag cctatggtcc ctggcagtct cc        52

<210> SEQ ID NO 57
<211> LENGTH: 52
<212> TYPE: DNA
<213> ORGANISM: artificial sequences
<220> FEATURE:
<221> NAME/KEY: source
<222> LOCATION: 1..52
<223> OTHER INFORMATION: /mol_type="DNA"
      /note="Primer"
      /organism="artificial sequences"

<400> SEQUENCE: 57
ccatctcatc cctgcgtgtc tccgactcag cgaatggtcc ctggcagtct cc        52

<210> SEQ ID NO 58
<211> LENGTH: 52
<212> TYPE: DNA
<213> ORGANISM: artificial sequences
<220> FEATURE:
<221> NAME/KEY: source
<222> LOCATION: 1..52
<223> OTHER INFORMATION: /mol_type="DNA"
      /note="Primer"
      /organism="artificial sequences"

<400> SEQUENCE: 58
ccatctcatc cctgcgtgtc tccgactcag ctactggtcc ctggcagtct cc        52

```
<210> SEQ ID NO 59
<211> LENGTH: 52
<212> TYPE: DNA
<213> ORGANISM: artificial sequences
<220> FEATURE:
<221> NAME/KEY: source
<222> LOCATION: 1..52
<223> OTHER INFORMATION: /mol_type="DNA"
      /note="Primer"
      /organism="artificial sequences"

<400> SEQUENCE: 59
ccatctcatc cctgcgtgtc tccgactcag ctcatggtcc ctggcagtct cc              52

<210> SEQ ID NO 60
<211> LENGTH: 52
<212> TYPE: DNA
<213> ORGANISM: artificial sequences
<220> FEATURE:
<221> NAME/KEY: source
<222> LOCATION: 1..52
<223> OTHER INFORMATION: /mol_type="DNA"
      /note="Primer"
      /organism="artificial sequences"

<400> SEQUENCE: 60
ccatctcatc cctgcgtgtc tccgactcag ctgttggtcc ctggcagtct cc              52

<210> SEQ ID NO 61
<211> LENGTH: 52
<212> TYPE: DNA
<213> ORGANISM: artificial sequences
<220> FEATURE:
<221> NAME/KEY: source
<222> LOCATION: 1..52
<223> OTHER INFORMATION: /mol_type="DNA"
      /note="Primer"
      /organism="artificial sequences"

<400> SEQUENCE: 61
ccatctcatc cctgcgtgtc tccgactcag cttgtggtcc ctggcagtct cc              52

<210> SEQ ID NO 62
<211> LENGTH: 52
<212> TYPE: DNA
<213> ORGANISM: artificial sequences
<220> FEATURE:
<221> NAME/KEY: source
<222> LOCATION: 1..52
<223> OTHER INFORMATION: /mol_type="DNA"
      /note="Primer"
      /organism="artificial sequences"

<400> SEQUENCE: 62
ccatctcatc cctgcgtgtc tccgactcag gaactggtcc ctggcagtct cc              52

<210> SEQ ID NO 63
<211> LENGTH: 52
<212> TYPE: DNA
<213> ORGANISM: artificial sequences
<220> FEATURE:
<221> NAME/KEY: source
<222> LOCATION: 1..52
<223> OTHER INFORMATION: /mol_type="DNA"
      /note="Primer"
      /organism="artificial sequences"

<400> SEQUENCE: 63
```
ccatctcatc cctgcgtgtc tccgactcag gacatggtcc ctggcagtct cc    52

<210> SEQ ID NO 64
<211> LENGTH: 52
<212> TYPE: DNA
<213> ORGANISM: artificial sequences
<220> FEATURE:
<221> NAME/KEY: source
<222> LOCATION: 1..52
<223> OTHER INFORMATION: /mol_type="DNA"
      /note="Primer"
      /organism="artificial sequences"

<400> SEQUENCE: 64
ccatctcatc cctgcgtgtc tccgactcag gagttggtcc ctggcagtct cc    52

<210> SEQ ID NO 65
<211> LENGTH: 52
<212> TYPE: DNA
<213> ORGANISM: artificial sequences
<220> FEATURE:
<221> NAME/KEY: source
<222> LOCATION: 1..52
<223> OTHER INFORMATION: /mol_type="DNA"
      /note="Primer"
      /organism="artificial sequences"

<400> SEQUENCE: 65
ccatctcatc cctgcgtgtc tccgactcag gatgtggtcc ctggcagtct cc    52

<210> SEQ ID NO 66
<211> LENGTH: 52
<212> TYPE: DNA
<213> ORGANISM: artificial sequences
<220> FEATURE:
<221> NAME/KEY: source
<222> LOCATION: 1..52
<223> OTHER INFORMATION: /mol_type="DNA"
      /note="Primer"
      /organism="artificial sequences"

<400> SEQUENCE: 66
ccatctcatc cctgcgtgtc tccgactcag gcaatggtcc ctggcagtct cc    52

<210> SEQ ID NO 67
<211> LENGTH: 52
<212> TYPE: DNA
<213> ORGANISM: artificial sequences
<220> FEATURE:
<221> NAME/KEY: source
<222> LOCATION: 1..52
<223> OTHER INFORMATION: /mol_type="DNA"
      /note="Primer"
      /organism="artificial sequences"

<400> SEQUENCE: 67
ccatctcatc cctgcgtgtc tccgactcag gtcttggtcc ctggcagtct cc    52

<210> SEQ ID NO 68
<211> LENGTH: 52
<212> TYPE: DNA
<213> ORGANISM: artificial sequences
<220> FEATURE:
<221> NAME/KEY: source
<222> LOCATION: 1..52
<223> OTHER INFORMATION: /mol_type="DNA"
      /note="Pprimer"
      /organism="artificial sequences"

<400> SEQUENCE: 68
ccatctcatc cctgcgtgtc tccgactcag gtgatggtcc ctggcagtct cc        52

<210> SEQ ID NO 69
<211> LENGTH: 52
<212> TYPE: DNA
<213> ORGANISM: artificial sequences
<220> FEATURE:
<221> NAME/KEY: source
<222> LOCATION: 1..52
<223> OTHER INFORMATION: /mol_type="DNA"
      /note="Primer"
      /organism="artificial sequences"

<400> SEQUENCE: 69
ccatctcatc cctgcgtgtc tccgactcag tacgtggtcc ctggcagtct cc        52

<210> SEQ ID NO 70
<211> LENGTH: 52
<212> TYPE: DNA
<213> ORGANISM: artificial sequences
<220> FEATURE:
<221> NAME/KEY: source
<222> LOCATION: 1..52
<223> OTHER INFORMATION: /mol_type="DNA"
      /note="Primer"
      /organism="artificial sequences"

<400> SEQUENCE: 70
ccatctcatc cctgcgtgtc tccgactcag tagctggtcc ctggcagtct cc        52

<210> SEQ ID NO 71
<211> LENGTH: 52
<212> TYPE: DNA
<213> ORGANISM: artificial sequences
<220> FEATURE:
<221> NAME/KEY: source
<222> LOCATION: 1..52
<223> OTHER INFORMATION: /mol_type="DNA"
      /note="Primer"
      /organism="artificial sequences"

<400> SEQUENCE: 71
ccatctcatc cctgcgtgtc tccgactcag tcagtggtcc ctggcagtct cc        52

<210> SEQ ID NO 72
<211> LENGTH: 52
<212> TYPE: DNA
<213> ORGANISM: artificial sequences
<220> FEATURE:
<221> NAME/KEY: source
<222> LOCATION: 1..52
<223> OTHER INFORMATION: /mol_type="DNA"
      /note="Primer"
      /organism="artificial sequences"

<400> SEQUENCE: 72
ccatctcatc cctgcgtgtc tccgactcag tccatggtcc ctggcagtct cc        52

<210> SEQ ID NO 73
<211> LENGTH: 52
<212> TYPE: DNA
<213> ORGANISM: artificial sequences
<220> FEATURE:
<221> NAME/KEY: source
<222> LOCATION: 1..52
<223> OTHER INFORMATION: /mol_type="DNA"
      /note="Primer"
      /organism="artificial sequences"

<400> SEQUENCE: 73
ccatctcatc cctgcgtgtc tccgactcag tcgttggtcc ctggcagtct cc            52

<210> SEQ ID NO 74
<211> LENGTH: 52
<212> TYPE: DNA
<213> ORGANISM: artificial sequences
<220> FEATURE:
<221> NAME/KEY: source
<222> LOCATION: 1..52
<223> OTHER INFORMATION: /mol_type="DNA"
      /note="Primer"
      /organism="artificial sequences"

<400> SEQUENCE: 74
ccatctcatc cctgcgtgtc tccgactcag tctctggtcc ctggcagtct cc            52

<210> SEQ ID NO 75
<211> LENGTH: 52
<212> TYPE: DNA
<213> ORGANISM: artificial sequences
<220> FEATURE:
<221> NAME/KEY: source
<222> LOCATION: 1..52
<223> OTHER INFORMATION: /mol_type="DNA"
      /note="Primer"
      /organism="artificial sequences"

<400> SEQUENCE: 75
ccatctcatc cctgcgtgtc tccgactcag tgactggtcc ctggcagtct cc            52

<210> SEQ ID NO 76
<211> LENGTH: 52
<212> TYPE: DNA
<213> ORGANISM: artificial sequences
<220> FEATURE:
<221> NAME/KEY: source
<222> LOCATION: 1..52
<223> OTHER INFORMATION: /mol_type="DNA"
      /note="Primer"
      /organism="artificial sequences"

<400> SEQUENCE: 76
ccatctcatc cctgcgtgtc tccgactcag tgtgtggtcc ctggcagtct cc            52

<210> SEQ ID NO 77
<211> LENGTH: 52
<212> TYPE: DNA
<213> ORGANISM: artificial sequences
<220> FEATURE:
<221> NAME/KEY: source
<222> LOCATION: 1..52
<223> OTHER INFORMATION: /mol_type="DNA"
      /note="Primer"
      /organism="artificial sequences"

<400> SEQUENCE: 77
ccatctcatc cctgcgtgtc tccgactcag ttcctggtcc ctggcagtct cc            52

<210> SEQ ID NO 78
<211> LENGTH: 52
<212> TYPE: DNA
<213> ORGANISM: artificial sequences
<220> FEATURE:
<221> NAME/KEY: source
<222> LOCATION: 1..52
<223> OTHER INFORMATION: /mol_type="DNA"
      /note="Primer"
      /organism="artificial sequences"

```
<400> SEQUENCE: 78
ccatctcatc cctgcgtgtc tccgactcag ttggtggtcc ctggcagtct cc            52
```

METHOD FOR MAKING AN ENRICHED LIBRARY

FIELD

The present invention relates to a method for making an enriched library comprising specific nucleic acid sequence information allowing to identifying at least one binding entity that binds to at least one target wherein the specific binding entity has been present in an in vitro display library.

BACKGROUND

Display technologies have been developed to combine information storage and amplification capabilities of nucleic acids with the functional activities of other compound. Display technologies rely on an association between a functional binding entity (i.e. phenotype) and a nucleic acid sequence informative (genotype) about the structure of the binding entity. Note: Nucleic acid aptamer technology is considered a display technology although a special case as the pheno- and genotype consist of the same molecule (DNA or RNA).

An advantage of such methods is that very large libraries can be constructed and probed for a desired activity of the functional binding entities. Library members having the desired activity can then be partitioned from library members not having the desired activity, thus creating an enriched library with a higher fraction of members having the desired activity. This process is called selection or enrichment. Some display technologies allows for rounds of selections, where the enriched library from one round is amplified and used to prepare a new enriched display library and used in a next round of selection and so forth. The structures of the library members in the enriched library can then be identified by their cognate nucleic acid sequence, thus allowing identification even from minute amounts of material.

Herein relevant libraries may according to the art be termed "in vitro display libraries".

The term "in vitro display library" shall herein be understood according to the art—i.e. as a library comprising numerous different binding entities wherein each binding entity is attached to a nucleic acid molecule and the nucleic acid molecule comprises specific nucleic acid sequence information allowing to identify the binding entity—i.e. once one knows the specific nucleic acid sequence information of the nucleic acid molecule one directly knows the structure of the specific binding entity attached to the nucleic acid molecule—the structure of the binding entity (i.e. phenotype) attached to the nucleic acid molecule (genotype) is herein termed B-structure.

The prior art describes a number of different methods to make such in vitro display libraries—herein suitable examples include e.g. EP1809743B1 (Vipergen), EP1402024B1 (Nuevolution), EP1423400B1 (David Liu), Nature Chem. Biol. (2009), 5:647-654 (Clark), WO 00/23458 (Harbury), Nature Methods (2006), 3(7), 561-570, 2006 (Miller), Nat. Biotechnol. 2004; 22, 568-574 (Melkko), Nature. (1990); 346(6287), 818-822 (Ellington), or Proc Natl Acad Sci USA (1997). 94 (23): 12297-302 (Roberts), WO06053571A2 (Rasmussen).

As described in e.g. above mentioned prior art—one can today make in vitro display libraries comprising very many (e.g. $10^{15}$) specific binding entities (e.g. $10^{15}$ different chemical compounds).

In view of this—it is evident that it would be very interesting to be able to improve the selection/enrichment step of such libraries to make an enriched library—e.g. to more efficient be able to identify the structure of a specific binding entity (e.g. a chemical compound) that binds to a target of interest (e.g. a medical important receptor molecule).

In FIG. 3 herein is shown an example of the in vitro display technology as described in EP1809743B1 (Vipergen)—as can be seen in this FIG. 3—the selection step of this example is performed by immobilizing the target (e.g. a receptor) to a solid surface (e.g. a bead or a glass plate).

Without being limited to theory—to our knowledge, the example in FIG. 3 herein may be seen as an example of herein relevant in vitro display technology prior art (e.g. above mentioned prior art)—i.e. to our knowledge the selection for suitable binding entities present within in vitro display libraries are in the prior art generally done by immobilizing the target (e.g. a receptor) to a solid support (e.g. a glass plate, a column, a bead, a nitrocellulose filter, a cell etc) before or after the display library binding event. Non-binders and low affinity binders are typically washed away, whereas the population enriched for binders are recovered from the solid support.

In prior art in vitro compartmentalization (IVC) have been described employed in technologies utilizing phenotype and genotype linkage for interrogating libraries. These prior art technologies can be divided into two groups: a) IVC utilized for facilitating establishing correct phenotype and genotype linkage, which allows for selection of function (e.g. specific target binding) later (post compartment disruption), and b) IVC for facilitating establishing correct phenotype and genotype linkage based on an activity of the phenotype inside the compartment, i.e in a compartment a gene is transcribed and translated and the resulting protein's function inside the compartment is used directly or indirectly for sorting, survival or amplification.

In other words herein relevant so-called IVC prior art technologies—may be described as a:

group a)—wherein the phenotype activity is interrogated AFTER the compartmentalized step; or group b)—wherein the phenotype activity is interrogated DURING the compartmentalized step.

Examples of IVC prior art belonging to group a):

Bertschinger et al. (2007) Protein Engineering, Design & Selection vol. 20 no. 2 pp. 57-68;

Miller O J, Bernath K, Agresti J J, Amitai G, Kelly B T, Mastrobattista E, Taly V, Magdassi S, Tawfik D S, Griffiths A D. Directed evolution by in vitro compartmentalization. Nat Methods. 2006 July; 3(7):561-70;

Doi, N. and Yanagawa, H. (1999) FEBS Lett., 457, 227-230; and Yonezawa, M., Doi, N., Kawahashi, Y., Higashinakagawa, T. and Yanagawa, H. (2003) Nucleic Acids Res., 31, e118.

Examples of IVC prior art belonging to group b):

Tawfik, D. S. and Griffiths, A. D. (1998) Man-made cell-like compartments for molecular evolution. Nat. Biotechnol., 16, 652-656;

Ghadessy, F. J., Ong, J. L. and Holliger, P. (2001) Proc. Natl Acad. Sci. USA, 98, 4552-4557;

Tay Y, Ho C, Droge P, Ghadessy F J. Selection of bacteriophage lambda integrases with altered recombination specificity by in vitro compartmentalization. Nucleic Acids Res. 2010 March; 38(4):e25. Epub 2009 Dec. 4;

Zheng Y, Roberts R J. Selection of restriction endonucleases using artificial cells. Nucleic Acids Res. 2007; 35(11):e83. Epub 2007;

Mastrobattista E, Taly V, Chanudet E, Treacy P, Kelly B T, Griffiths A D. High-throughput screening of enzyme libraries: in vitro evolution of a beta-galactosidase by fluorescence-activated sorting of double emulsions. Chem Biol. 2005 December; 12(12):1291-300;

Levy M, Griswold K E, Ellington A D. Direct selection of trans-acting ligase ribozymes by in vitro compartmentalization. RNA. 2005 October; 11(10):1555-62. Epub 2005 Aug. 30;

Sepp A, Choo Y. Cell-free selection of zinc finger DNA-binding proteins using in vitro compartmentalization. J Mol Biol. 2005 Nov. 25; 354(2):212-9. Epub 2005 Oct. 3;

Bernath K, Magdassi S, Tawfik D S. Directed evolution of protein inhibitors of DNA-nucleases by in vitro compartmentalization (IVC) and nano-droplet delivery. J Mol Biol. 2005 Feb. 4; 345(5):1015-26. Epub 2004 Dec. 7.

Examples of further IVC prior art may be found in:

Bertschinger et al, (2004) Protein Engineering, Design & Selection vol. 20 no. 2 pp. 699-707;

Chen Yu et al, (November 2008) Nucleic Acid Research, Vol. 36, Nr. 19, Pages: Article No. E128;

Hansen et al. J. Am. Chem. Soc., 2009, 131 (3), pp 1322-1327.

SUMMARY OF THE DISCLOSURE

The problem to be solved by the present invention may be seen as to provide an improved in vitro display based method in order to make an enriched library comprising at least one binding entity (e.g. a chemical compound) that binds to a target of interest (e.g. a medical relevant receptor).

In many cases, most notably in the development of therapeutics, two parameters for a binding entity (drug) are especially important, namely the potency (affinity) and the off rate (dissociative half-life of drug:target complex). The present invention provides an improved solution for in vitro display methods to enrich for both these important binding parameters.

In other cases, the on-rate characteristic for a binding identity is desired. The present invention provides an improved solution for in vitro display methods to enrich for on-rate characteristic for a binding identity.

The solution may be seen as based on that:

(i): making an in vitro display library of binding entities (i.e. phenotype) attached to nucleic acid molecules (genotype)—this step may be made according to known prior art techniques for making such in vitro display libraries;

(ii): making structures comprising target (i.e. phenotype) attached to a nucleic acid molecule (genotype)—this step may be made according to known prior art techniques for making such structures; and wherein the method as described herein may be seen as characterized by that:

(iii): the binding step is performed in solution (e.g. under aqueous conditions);

(iv): there is used a suitable in vitro compartmentalization system (e.g. a water-in-oil emulsion system) creating more individual compartments than target molecules;

(v): fuse co-compartmentalized target and binding entity genotypes;

(vi): de-compartmentalize; to get an enrichment of fused genotypes (positive binders in the in vitro display library will have a higher propensity for being fused than none-binders); and (vii): optionally e.g. purify and/or preferential amplify the fused genotypes.

Based on the detailed description herein and the common general knowledge—the skilled person may perform the steps (iii) to steps (vi) in a number of different ways.

Step (vii) is an optional step—as described herein once one has obtained the enriched library of step (vi) one may use this library in different ways according to art—e.g. the enriched library may be considered as an enriched in vitro display library that e.g. can be used in a second round of selection/enrichment or one may identify the structure of a specific binding entity of interest directly from the enriched library of step (vi).

As discussed above—herein relevant so-called IVC prior art technologies—may be described as a:

group a)—wherein the phenotype activity is interrogated AFTER the compartmentalized step; or group b)—wherein the phenotype activity is interrogated DURING the compartmentalized step.

As evident from above and as further discussed herein—the method as described herein is conceptionally different from such so-called IVC prior art technologies—e.g. due to that the phenotype activity is interrogated in step (iii) of first aspect, which is BEFORE the compartmentalized step (iv) of first aspect.

A simple way to explain the principle of the novel method as described herein, is that non-binders in the display library is randomly distributed in the compartments and therefore co-compartmentalize with the target in a random fashion, with a frequency depending on the ratio between the number of compartments and the number of target molecules. In contrast, binders, due to the binding activity, will co-compartmentalize together with target molecules—independently of the ratio between the number of compartments and the number of target molecules. Consequently, enrichment of a binder is achieved when the ratio between the number of compartments and the number of target molecules is larger than 1—the higher ratio the higher enrichment.

In FIGS. 1 and 2 herein are provided illustrative examples of the novel method as described herein.

In working examples 1 and 2 herein are provided an example with herein relevant numbers of e.g. binding entities and target of interest—as can be seen in the conclusion of the examples 1 and 2—by using the method as described herein one may get e.g. an 1000 times enrichment of binders in the library.

Accordingly, a first aspect of the invention relates to a method a method for making an enriched library comprising specific nucleic acid sequence information allowing to identifying at least one binding entity that binds to at least one target wherein the specific binding entity has been present in an in vitro display library and wherein the method comprises the steps of:

(i): making an in vitro display library of at least 100 different binding entities ($B_n$ (n=100 or more), wherein each binding entity is attached to a nucleic acid molecule and the nucleic acid molecule comprises specific nucleic acid sequence information allowing to identify the binding entity—i.e. once one knows the specific nucleic acid sequence information of the nucleic acid molecule one directly knows the structure of the specific binding entity attached to the nucleic acid molecule—the structure of the binding entity (i.e. phenotype) attached to the nucleic acid molecule (genotype) is herein termed B-structure;

(ii): making nucleic acid molecules with at least one target $T_n$ (n=1 or more) attached to a nucleic acid molecule and the nucleic acid molecule comprises specific nucleic acid sequence information allowing to identify the specific target, wherein the target is capable of binding to at least one of the binding entities present in the library of step (i)—the structure of the target (i.e. phenotype) attached to the nucleic acid molecule (genotype) is herein termed T-structure;

and wherein the method is characterized by that:

(iii): mixing a solution comprising X (X is a number greater than $10^4$) numbers of B-structures of the library of step (i) with a solution comprising Y (Y is a number greater than $10^2$) numbers of T-structures of step (ii) under binding conditions, i.e. conditions where a B-structure containing a binding entity capable of binding to a target molecule, binds more efficiently to the corresponding T-structure, than a B-structure containing a binding entity not capable of binding to the same target do and wherein one gets binding of at least one of the binding entities to at least one target thereby creating a complex comprising a B-structure bound to a T-structure (herein termed $B_{BoundTo}$T-structure);

(iv): applying an in vitro compartmentalization system—under binding conditions, i.e. conditions where a B-structure containing a binding entity capable of binding to a target molecule, binds more efficiently to the corresponding T-structure, than a B-structure containing a binding entity not capable of binding to the same target do—wherein the compartmentalization system comprises at least 2 times more individual compartments than the Y number of T-structures present in step (iii) under conditions wherein the B-structures, T-structures and $B_{BoundTo}$T-structures enter randomly into the individual compartments; and (v): fusing the nucleic acid molecules of a B-structure and a T-structure which are both present within the same individual compartment—i.e. fusing the nucleic acid molecule of the B-structure to the nucleic acid molecule of the T-structure—this structure is herein termed $BT_{Fused}$-structure and the $BT_{Fused}$-structure comprises the specific nucleic acid sequence information allowing to identify the binding entity of step (i) and the specific nucleic acid sequence information allowing to identify the specific target of step (ii); and (vi): combining the content of the individual compartments of step (v) under conditions wherein there is no fusing of the nucleic acid molecules of a B-structure and a T-structure—i.e. there is not created any new $BT_{Fused}$-structure not already created in step (v)—in order to get a library of $BT_{Fused}$-structures, wherein the library is an enriched library of species of $BT_{Fused}$-structures originating from binding pairs of target and binder entity when compared to $BT_{Fused}$-structures originating from nonbinding pairs of target and binder entity.

The method of the first aspect as described herein may be termed Enrichment by Co-Compartmentalization (ECC).

Advantageous in ECC method as described herein is that enrichment for important binding characteristics can be optimized for in isolation—because ECC is a homogenous assay—target is not immobilization to a solid support. Prior art methods are heterogenous—rely on target immobilization to a solid support (e.g. beads, columns, cells, plastic, filters etc). Heterogenous assays are notoriously more difficult to control than homogenous assay due e.g. avidity effects, density of coating, and interference of the solid support itself with the assay.

As discussed above, in herein relevant in vitro display technology prior art (e.g. above mentioned prior art)—selection for suitable binding entities present within in vitro display libraries are in the prior art generally done by immobilizing the target (e.g. a receptor) to a solid support (e.g. a glass plate, a column, a bead, a nitrocellulose filter, a cell etc) before or after the display library binding event. Non-binders and low affinity binders are typically washed away, whereas the population enriched for binders are recovered from the solid support.

Accordingly, as understood by the skilled person, when there above is said that herein relevant prior art methods "rely on target immobilization to a solid support" is it understood by the skilled person in the way that the selection for suitable binding entities relies on this immobilization of target to a solid support as an essential element to get the selection for suitable binding entities.

As evident to the skilled person, the method of the first aspect is not such a prior at method that rely on target immobilization to a solid support, since the selection of the binding entities is based on the separation of the $B_{BoundTo}$T-structures into the individual compartments as required in step (iv) of the first aspect.

In line of above and as understood by the skilled person—in the method of the first aspect one could theoretically image a situation, wherein the target T-structure of step (ii) would e.g. comprise a bead. It could theoretically be a T-structure, wherein the target is bound to a bead and the nucleic acid molecule that comprises the specific nucleic acid sequence information allowing identifying the specific target of the T-structure of step (ii) is then also bound to the bead.

As evident to the skilled person—such a special T-structure comprising a bead will not change the fact that the method of the first aspect is not a method, wherein the selection for suitable binding entities relies on this immobilization of target to a solid support.

In line of above and as understood by the skilled person in the present context, the method of the first aspect may be seen as a method which implies that the $B_{BoundTo}$T-structures (i.e. the target-binding entity complexes) remain suspended in solution in the individual/separated compartments of step (iv) of the first aspect.

ECC allows optimizing for major binding characteristic for binding of binding entity to target in isolation. For example potency (affinity), association rate (on rate) or dissociative half-life of binding entity and target (off rate).

Affinity based selection is achieved by using equilibrium conditions and controlled by the target concentration in the mixing step (binding step), i.e. 90% of the molecules of a binding entity in the display library having a $K_d$ equal to 10 times smaller than the target concentration are target bound, whereas 50% of the molecules of a binding entity having a $K_d$ equal to the target concentration are, and 10% of the molecules of a binding entity having a $K_d$ 10 times smaller than the target concentration are. Consequently, enrichment for affinity is easily controlled by the target concentration in the mixing step.

A separate aspect of the invention relates to an enriched library of step (vi) of the first aspect and which is obtainable by the method of the first aspect or herein related embodiments of the first aspect.

Embodiments of the present invention are described below, by way of examples only.

DRAWINGS

FIG. 1: Illustrative example of the principle of the principle of the method as described herein.

FIG. 2: Illustrative example of the principle of the principle of the method as described herein—it is an illustrative example wherein emulsion PCR is used in the fusion step (v) of the first aspect.

FIG. 3: Herein is shown an example of the in vitro display technology as described in EP1809743B1 (Vipergen)—as can be seen in this FIG. 3—the selection step of this example is performed by immobilizing the target (e.g. a receptor) to a solid surface (e.g. a bead or a glass plate).

FIG. 5 shows results from 454 sequencing as described in Example 4.

FIG. 7 shows DNA results from using emulsion breaking and DNA recovery protocol (see Example 6)

DETAILED DESCRIPTION

Figure 1:
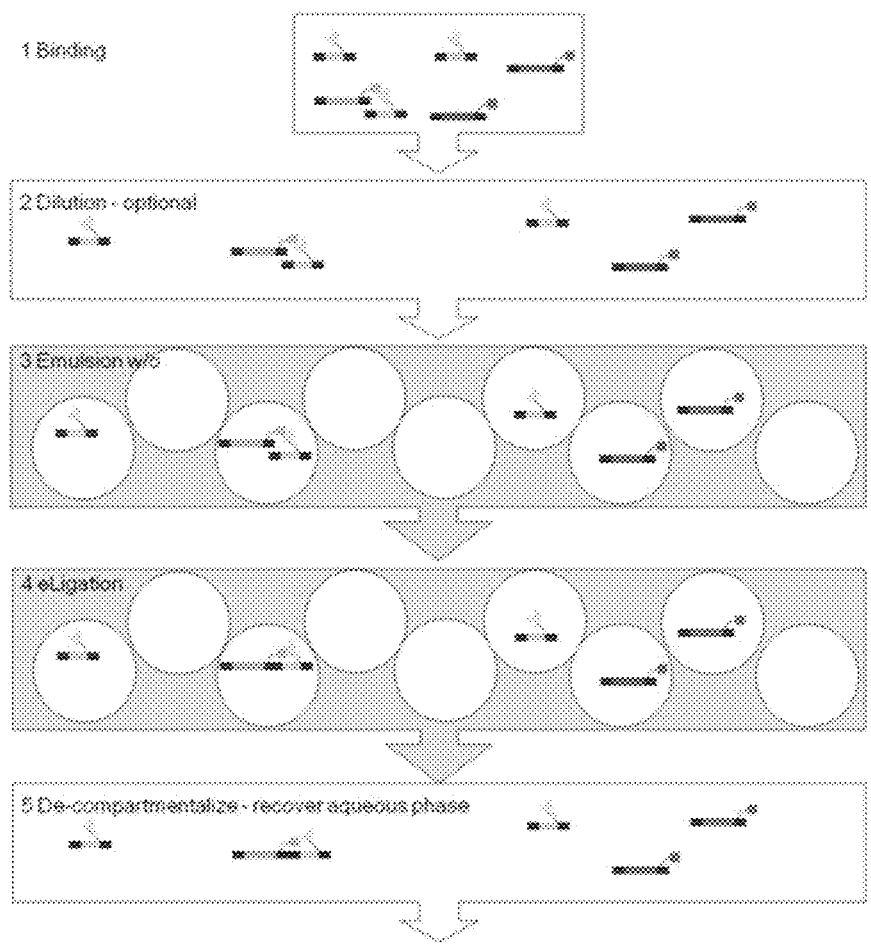

In Vitro Display Library—Step (i) of First Aspect

The term "in vitro display library" shall be understood according to the art—i.e. as a library comprising numerous different binding entities wherein each binding entity is attached to a nucleic acid molecule and the nucleic acid molecule comprises specific nucleic acid sequence information allowing to identify the binding entity—i.e. once one knows the specific nucleic acid sequence information of the nucleic acid molecule one directly knows the structure of the specific binding entity attached to the nucleic acid molecule—the structure of the binding entity (i.e. phenotype) attached to the nucleic acid molecule (genotype) is herein termed B-structure.

As discussed herein—the prior art describes a number of different methods to make such in vitro display libraries—i.e. an in vitro display library of step (i).

Said in other words, it is today routine work for the skilled person to properly make a structure of the binding entity (i.e. phenotype) attached to the nucleic acid molecule (genotype)—i.e. what is herein termed a "B-structure".

As known in the art—binding entity (i.e. phenotype) may be attached to the nucleic acid molecule (genotype) by e.g. a covalent binding or e.g. a high affinity non-covalent binding.

It may herein be preferred that the binding entity (i.e. phenotype) is attached to the nucleic acid molecule (genotype) by a covalent binding.

An in vitro display library of step (i) comprises a number of different B-structures—i.e. in line of above it is routine work for the skilled person to make an in vitro display library of step (i).

Herein suitable examples include e.g. EP1809743B1 (Vipergen), EP1402024B1 (Nuevolution), EP1423400B1 (David Liu), Nature Chem. Biol. (2009), 5:647-654 (Clark), WO 00/23458 (Harbury), Nature Methods (2006), 3(7), 561-570, 2006 (Miller), Nat. Biotechnol. 2004; 22, 568-574 (Melkko), Nature. (1990); 346(6287), 818-822 (Ellington), or Proc Natl Acad Sci USA (1997). 94 (23): 12297-302 (Roberts).

Said in other words, the in vitro display library of step (i) of first aspect may be made in a numbers of ways as described in the prior art.

Without being limited to theory—herein suitable examples of in vitro display library technologies include DNA Encoded Chemical Library technologies, Aptamer technologies, RNA/DNA display technologies such as CIS display, Ribosome display, mRNA display or bead display system (using nucleic acids for encoding).

As described in the prior art (see e.g. EP1809743B1 (Vipergen))—the nucleic acid molecule of the B-structure may e.g. be PNA, LNA, RNA, DNA or combinations thereof. Preferably, the nucleic acid molecule of the B-structure is DNA.

In a preferred embodiment of the present invention the nucleic acid molecule (genotype) attached to the binding entity (phenotype) in the B-structure may be a double stranded nucleic acid molecule.

In a preferred embodiment of the present invention the nucleic acid molecule (genotype) attached to the binding entity (phenotype) in the B-structure may be at least 0% double stranded (i.e. single stranded), may be at least 10% double stranded, at least 20% double stranded, at least 30% double stranded, at least 40% double stranded, at least 50% double stranded, at least 60% double stranded, at least 70% double stranded, at least 80% double stranded, at least 90% double stranded, or 100% double stranded.

In a preferred embodiment of the present invention the nucleic acid molecule (genotype) attached to the binding entity (phenotype) in the B-structure may contain a PCR priming site or a fraction hereof.

In a preferred embodiment of the present invention the nucleic acid molecule (genotype) attached to the binding entity (phenotype) in the B-structure may contain 2 PCR priming sites or fractions hereof.

In a preferred embodiment of the present invention the nucleic acid molecule (genotype) attached to the binding entity (phenotype) in the B-structure may contain at least 3 PCR priming sites or fractions hereof.

In some embodiments of the present invention a fraction of a PCR priming site comprises at least 5 nucleotides, at least 6 nucleotides, at least 7 nucleotides, at least 8 nucleotides, at least 9 nucleotides, at least 10 nucleotides, at least 11 nucleotides, at least 12 nucleotides, at least 13 nucleotides, at least 14 nucleotides, at least 15 nucleotides, at least 16 nucleotides, at least 17 nucleotides, at least 18 nucleotides, at least 19 nucleotides, or at least 20 nucleotides.

In some embodiments of the present invention the nucleic acid molecule (genotype) attached to the binding entity (phenotype) in the B-structure may contain a single stranded overhang reverse complement to a single stranded overhang of the genotype of the B structure.

In some embodiments of the present invention the nucleic acid molecule (genotype) attached to the binding entity (phenotype) in the B-structure may contain a single stranded overhang reverse complement to a single stranded overhang of the genotype of the B structure. The overhang may preferentially be 1 nucleotide, 2 nucleotides, 3 nucleotides, 4 nucleotides, 5 nucleotides, 6 nucleotides, 7 nucleotides, 8 nucleotides, 9 nucleotides, or 10 nucleotides long.

Binding Entity

The Binding entity may any suitable binding entity of interest.

Step (i) of first aspect reads "at least 100 different binding entities ($B_n$ (n=100 or more)".

In practice, there may many times be many more different binding entities present in the library of step (i)—such as e.g. at least $10^4$, at least $10^5$ or at least $10^6$ different binding entities—i.e. where n=at least $10^4$, n=at least $10^5$ or n=at least $10^6$.

Accordingly, in a theoretical situation, wherein the library comprises exactly $10^4$ different binding entities—one may herein express this as $B_n$ (n=$10^4$) or $B_{10}^{4}$.

Without being limited to theory it may be difficult to make a library with more than $10^{20}$ different binding entities.

Suitable examples may be wherein the binding entity is at least one binding entity selected from the group consisting of: a protein, a polypeptide, a nucleic acid and a chemical compound (preferably a small chemical compound with an average molecular weight MW below 10000 dalton, more preferably an average molecular weight MW below 5000 dalton, even more preferably an average molecular weight MW below 1000 dalton.

Suitable examples of a herein relevant binding entity (such as e.g. a chemical compound) may be found in the prior art—see e.g. EP1809743B1 (Vipergen), EP1402024B1 (Nuevolution), EP1423400B1 (David Liu), Nature Chem. Biol. (2009), 5:647-654 (Clark), WO 00/23458 (Harbury), Nature Methods (2006), 3(7), 561-570, 2006 (Miller), Nat. Biotechnol. 2004; 22, 568-574 (Melkko), Nature. (1990); 346(6287), 818-822 (Ellington), or Proc Natl Acad Sci USA (1997). 94 (23): 12297-302 (Roberts).

In short, the skilled person is aware of numerous different possible binding entities that could be of interest in the present context.

Step (ii) of First Aspect

As discussed herein—the target shall be capable of binding to at least one of the binding entities present in the library of step (i)—otherwise it is not a suitable target that can be used to identify a specific binding entity that binds to at least one target.

In line of above—it is today routine work for the skilled person to properly attach a target (i.e. phenotype) to a nucleic acid molecule (genotype) and thereby make a structure of the target (i.e. phenotype) attached to the nucleic acid molecule (genotype)—i.e. what is herein termed "T-structure".

Said in other words, one may make herein relevant "T-structure" based on e.g. the same prior art literature discussed above for making the in vitro display library of step (i).

As known in the art—target (i.e. phenotype) may be attached to the nucleic acid molecule (genotype) by e.g. a covalent binding or e.g. a high affinity non-covalent binding.

It may herein be preferred that the target (i.e. phenotype) is attached to the nucleic acid molecule (genotype) by a covalent binding.

Step (i) of first aspect reads "at least one target Tn (n=1 or more)".

As discussed herein—an advantage of the method as described herein is that one in an efficient and rapid way can simultaneous screen for binding entities that could bind to e.g. two or more targets.

For instance—the targets could be two different receptor molecules and the method as described herein could then simultaneous identify one binding entity that binds to one of the receptors and another binding entity that binds to the other receptor.

In the example above (with two different e.g. receptor targets) we would have a situation, wherein the target Tn (n=2) or alternatively expressed $T_2$.

In line of above—it may be relevant to have at least two different targets in step (ii) [i.e. Tn (n=2 or more], or to at least three different targets in step (ii) [i.e. Tn (n=3 or more], or to have at least ten different targets in step (ii) [i.e. Tn (n=10 or more], or to at least hundred different targets in step (ii) [i.e. Tn (n=100 or more].

Without being limited to theory it may be difficult to have than 100.000 different targets in step (ii)—i.e. more than 100.000 different T-structures.

As described in the prior art (see e.g. EP1809743B1 (Vipergen))—the nucleic acid molecule of the T-structure may e.g. be PNA, LNA, RNA, DNA or combinations thereof. Preferably, the nucleic acid molecule of the T-structure is DNA.

In a preferred embodiment of the present invention the nucleic acid molecule (genotype) attached to the target (phenotype) in the T-structure may be at least 5 nucleotides long, at least 10 nucleotides long, at least 20 nucleotides long, at least 30 nucleotides long, at least 40 nucleotides long, at least 50 nucleotides long, at least 60 nucleotides long, at least 70 nucleotides long, at least 80 nucleotides long, at least 90 nucleotides long, at least 100 nucleotides long, at least 200 nucleotides long, at least 300 nucleotides long, at least 400 nucleotides long, or at least 500 nucleotides long.

In a preferred embodiment of the present invention the nucleic acid molecule (genotype) attached to the target (phenotype) in the T-structure may be a double stranded nucleic acid molecule.

In a preferred embodiment of the present invention the double stranded nucleic acid molecule (genotype) attached to the target (phenotype) in the T-structure may be at least 5 base pairs long, at least 10 base pairs long, at least 20 base pairs long, at least 30 base pairs long, at least 40 base pairs long, at least 50 base pairs long, at least 60 base pairs long, at least 70 base pairs long, at least 80 base pairs long, at least 90 base pairs long, at least 100 base pairs long, at least 200 base pairs long, at least 300 base pairs long, at least 400 base pairs long, or at least 500 base pairs long.

In a preferred embodiment of the present invention the nucleic acid molecule (genotype) attached to the target (phenotype) in the T-structure may be at least 0% double stranded (i.e. single stranded), may be at least 10% double stranded, at least 20% double stranded, at least 30% double stranded, at least 40% double stranded, at least 50% double stranded, at least 60% double stranded, at least 70% double stranded, at least 80% double stranded, at least 90% double stranded, or 100% double stranded.

In a preferred embodiment of the present invention the nucleic acid molecule (genotype) attached to the target (phenotype) in the T-structure may contain a PCR priming site or a fraction hereof.

In a preferred embodiment of the present invention the nucleic acid molecule (genotype) attached to the target (phenotype) in the T-structure may contain 2 PCR priming sites or fractions hereof.

In a preferred embodiment of the present invention the nucleic acid molecule (genotype) attached to the target (phenotype) in the T-structure may contain at least 3 PCR priming sites or fractions hereof.

In some embodiments of the present invention a fraction of a PCR priming site comprises at least 5 nucleotides, at least 6 nucleotides, at least 7 nucleotides, at least 8 nucleotides, at least 9 nucleotides, at least 10 nucleotides, at least 11 nucleotides, at least 12 nucleotides, at least 13 nucleotides, at least 14 nucleotides, at least 15 nucleotides, at least 16 nucleotides, at least 17 nucleotides, at least 18 nucleotides, at least 19 nucleotides, or at least 20 nucleotides.

In some embodiments of the present invention the nucleic acid molecule (genotype) attached to the target (phenotype) in the T-structure may contain a single stranded overhang reverse complement to a single stranded overhang of the genotype of the B structure.

In some embodiments of the present invention the nucleic acid molecule (genotype) attached to the target (phenotype) in the T-structure may contain a single stranded overhang reverse complement to a single stranded overhang of the genotype of the B structure. The overhang may preferentially be 1 nucleotide, 2 nucleotides, 3 nucleotides, 4 nucleotides, 5 nucleotides, 6 nucleotides, 7 nucleotides, 8 nucleotides, 9 nucleotides, or 10 nucleotides long.

In some embodiments of the present invention the nucleic acid molecule (genotype) attached to the target (phenotype)

in the T-structure may contain a unique sequence specific for each target molecule (Unique Molecule Identifier—UMI).

In some embodiments of the present invention the nucleic acid molecule (genotype) attached to the target (phenotype) in the T-structure may contain a unique sequence specific for each target molecule (Unique Molecule Identifier—UMI) consisting of at least 16 Ns (N=A, C, G, or T), at least 17 Ns, at least 18 Ns, at least 19 Ns, at least 20 Ns, at least 21 Ns, at least 22 Ns, at least 23 Ns, at least 24 Ns, at least 25 Ns, at least 26 Ns, at least 27 Ns, at least 28 Ns, at least 29 Ns, or at least 30 Ns.

In some embodiments of the present invention the nucleic acid molecule (genotype) attached to the target (phenotype) in the T-structure may contain a unique sequence specific for each target molecule (Unique Molecule Identifier—UMI) consisting of a continuous sequence.

In some embodiments of the present invention the nucleic acid molecule (genotype) attached to the target (phenotype) in the T-structure may contain a unique sequence specific for each target molecule (Unique Molecule Identifier—UMI) consisting of a discontinuous sequence.

In some embodiments of the present invention the nucleic acid molecule (genotype) attached to a first target (phenotype) in the T-structure may contain a first sequence different from a second target's second genotype sequence (allowing multiplexing).

In some embodiments of the present invention the nucleic acid molecule (genotype) attached to a first target (phenotype) in the T-structure may contain a first sequence different from a second target's second genotype sequence (allowing multiplexing), wherein the first and second target genotype comprise different PCR priming sites.

Target

The target may be any suitable target of interest.

In a preferred embodiment of the present invention—specific enriching methods for the enrichment facilitating identification of binding entities with desired characteristics include but are not limited to: enrichment on nucleic acid attached target molecules. In this approach the target molecules is e.g. DNA, RNA, protein, carbohydrate, organic or inorganic molecule.

As known in the art—a suitable target could e.g. be a receptor molecule present in e.g. the human body and one would be interested in identifying a binding entity (e.g. a chemical compound) that can bind to the receptor.

In accordance with the prior art—suitable examples may be wherein the target is DNA, RNA, protein, carbohydrate, organic or inorganic molecule or fragments hereof.

In accordance with the prior art—suitable examples may be wherein the target is an autoantigen, a bacterial protein, a blood protein, a cell adhesion protein, a cytokine, a cytoskeleton protein, a DNA-binding protein, a developmental protein, an engineered protein, an enzyme, an extracellular matrix protein, a GTP-binding protein regulator, a glycoprotein, a growth factor, a heat shock protein, a lipoprotein, a membrane protein, a metalloprotein, a motor protein, a phosphoprotein, a prion, a protein complex, a protein domain, a RNA-binding protein, a receptor, a recombinant protein, a seed storage protein, a structural protein, a transcription coregulator protein, a transport protein, a viral protein or fragments hereof.

In short, the skilled person is aware of numerous different possible targets than could be of interest in the present context.

Step (iii) of First Aspect:

In the illustrative example of FIG. 1 herein—this step (iii) corresponds to the step "1 Binding".

As discussed above—step (iii) reads:

"mixing a solution comprising X (X is a number greater than $10^4$) numbers of B-structures of the library of step (i))"

The term "X" in relation to numbers of B-structures shall be understood as the total numbers of B-structures of the library of step (i).

For instance—if the library comprises 100 different binding entities ($B_n$ (n=100)) and there are 100 copies of each of the 100 different B-structures then the number "X" is equal to $100 \times 100 = 10^4$.

In practice the number X may many times be higher—for instance, if the library comprises $10^6$ different binding entities [$B_n$ (n=$10^6$)] and there are $10^4$ copies of each of the $10^6$ different B-structures then the number "X" is equal to $10^6 \times 10^4 = 10^{10}$.

As discussed above—step (iii) reads:

"a solution comprising Y (Y is a number greater than $10^2$) numbers of T-structures of step (ii)"

The term "Y" in relation to numbers of T-structures shall be understood as the total numbers of T-structures of the library of step (ii).

For instance—if there is only one target in step (ii) [$T_n$ (n=1)] and there are $10^2$ copies of each of the T-structure then the number "Y" is equal to $1 \times 10^2 = 10^2$.

As discussed above—one could have e.g. 2 different targets (e.g. two different receptor molecules)—in this case there would be two targets in step (ii) [$T_n$ (n=2)] and if there would be $10^2$ copies of each of the two different T-structures then the number "Y" would be equal to $2 \times 10^2 = 2 \times 10^2 = 200$.

In practice one may many times have significant more copies of a relevant T-structure—the reason for this is that one preferably wants to have numerous copies of a relevant T-structure in order to increase the probability for that the target on a T-structure bind to the binding entity of a B-structure.

Accordingly, in a preferred embodiment there are at least $10^0$, at least $10^1$, at least $10^2$, at least $10^3$, at least $10^4$, at least $10^5$, at least $10^6$, at least $10^7$ at least $10^8$, at least $10^9$, at least $10^{10}$, at least $10^{11}$, at least $10^{12}$, at least $10^{13}$, at least $10^{14}$, at least $10^{15}$ or at least $10^{16}$ copies of a T-structure of interest.

Advantageous in ECC method as described herein is that enrichment for important binding characteristics can be optimized for in isolation—because ECC is a homogenous assay—target is not immobilization to a solid support. Prior art methods are heterogenous—rely on target immobilization to a solid support (e.g. beads, columns, cells, plastic, filters etc). Heterogenous assays are notoriously more difficult to control than homogenous assay due e.g. avidity effects, density of coating, and interference of the solid support itself with the assay.

ECC allows optimizing for major binding characteristic for binding of binding entity to target in isolation. For example potency (affinity), association rate (on rate) or dissociative half-life of binding entity and target (off rate).

Affinity based selection is achieved in step (iii) e.g. by using equilibrium conditions and controlled by the target concentration in the mixing step (binding step), i.e. 90% of the molecules of a binding entity in the display library having a $K_d$ equal to 10 times smaller than the target concentration are target bound, whereas 50% of the molecules of a binding entity having a $K_d$ equal to the target concentration are, and 10% of the molecules of a binding entity having a $K_d$ 10 times smaller than the target concentration are.

Consequently, enrichment for affinity is easily controlled by the target concentration in the mixing step.

In a preferred embodiment of the present invention—the concentration of T-structures in the "mixing step (iii)" is at least $10^{-16}$ M, at least $10^{-14}$ M, at least $10^{-13}$ M, at least $10^{-12}$ M, at least $10^{-11}$ M, at least $10^{-10}$ M, at least $10^{-9}$ M, at least $10^{-8}$ M, at least $10^{-7}$ M, at least $10^{-6}$ M, at least $10^{-5}$ M, at least $10^{-4}$ M, or at least $10^{-3}$ M.

Alternatively, association rate based selection is achieved by controlling the time allowed for the mixing step (iii)—accordingly, the "mixing step" may be performed for a time period shorter than the time needed to reach binding equilibrium conditions.

Step (iii) further reads:

"under binding conditions, i.e. conditions where a B-structure containing a binding entity capable of binding to a target molecule, binds more efficiently to the corresponding T-structure, than a B-structure containing a binding entity not capable of binding to the same target do and wherein one gets binding of at least one of the binding entities to at least one target thereby creating a complex comprising a B-structure bound to a T-structure (herein termed $B_{BoundTo}$T-structure)"

The term "binds more efficiently" shall be understood according to common practice e.g. higher affinity, faster on rate, or slower dissociation rate.

As known to the skilled person—in the present context it is routine work for the skilled person to perform step (iii) under conditions, wherein one get this "binds more efficiently" effect.

For instance—one may easy obtain this "binds more efficiently" effect by e.g. using B and T-structures genotypes that essentially do not binds (e.g. by hybridization base pairing) under the binding conditions of step (iii)—as evident to the skilled person this could e.g. be obtained by using e.g. double stranded DNA with none or very small single stranded base-pairing overlap as genotypes for the B and T-structures.

It would be routine work for the skilled person to optimize the binding conditions of step (iii) in order to get the required "binds more efficiently" effect of step (iii).

As known to the skilled person—herein relevant optimization parameters may e.g. be inonic strength, temperature etc.

Accordingly, under any practical herein relevant circumstance—the skilled person would not be in any reasonable doubt if he (after e.g. proper routine adjustment of the binding conditions) would work under binding conditions of step (iii) or not.

In a preferred embodiment, step (iii) is performed under binding conditions, wherein a B-structure containing a binding entity capable of binding to a target molecule, binds 10 fold (more preferably 100 fold, even more preferably 1000 fold) more efficiently to the corresponding T-structure, than a B-structure containing a binding entity not capable of binding to the same target do.

Step (iii-b)—Dilution Step—Preferred Embodiment:

In the illustrative example of FIG. 1 herein—this optional step (iii-b) corresponds to the step "2 Dilution".

The mixing step (iii) may preferably be followed by a dilution step—this is herein termed step (iii-b) and is performed before the step (iv) of the first aspect.

Accordingly, in a preferred embodiment the method of the first aspect comprises an additional step (iii-b) that is performed before the step (iv) of the first aspect, comprising:

(iii-b): diluting the solution of step (iii) at least 2 fold under binding conditions, i.e. conditions where a B-structure containing a binding entity capable of binding to a target molecule, binds more efficiently to the corresponding T-structure, than a B-structure containing a binding entity not capable of binding to the same target do.

The dilution solution introduced and the conditions (e.g. temperature) in the dilution step (iii-b) may be different from the binding conditions of the mixing step (iii)—but the above described effects shall be maintained in dilution step (iii-b).

It may be preferred in step (iii-b) to have a diluting the solution of step (iii) at least $10^2$ fold, or have a diluting the solution of step (iii) at least $10^3$ fold, or have a diluting the solution of step (iii) at least $10^4$ fold, or have a diluting the solution of step (iii) at least $10^5$ fold, or have a diluting the solution of step (iii) at least $10^6$ fold, or have a diluting the solution of step (iii) at least $10^7$ fold, or have a diluting the solution of step (iii) at least $10^8$ fold or have a diluting the solution of step (iii) at least $10^9$ fold.

An advantage of this diluting step is that enrichment can be performed based on dissociative half-life of the BT-structures and easily controlled by the degree of dilution and the incubation time. When the mixing solution of step (iii) is diluted biding of binding entity and target is a less likely event to happened whereas the "un-binding event"—the off rate (the dissociative half-life) is independent of the dilution. Consequently, in a very dilute solution (T-structure concentration<<$K_d$) essentially only dissociation will take place.

Therefore, enrichment for dissociative half-life of the BT-structures is conveniently controlled by the degree of dilution and the incubation time.

The dissociative half-life together with the affinity is of greatest importance in the usability of a binding entity. Most notable, for development of effective new drugs where high affinity and long dissociative half-life are critical parameters for pharmacological effect (Nature Reviews Drug Discovery (2006) 5, 730-739, (Copeland). Hence, the method of the present new invention permits enrichment for these two parameters in an unprecedented effective and controllable manner. Moreover, the two parameters can be controlled independently of each other.

Step (iv) of First Aspect:

A simple way to view this step is that the binding of target with binding entity of step (iii) is "transformed" into co-compartmentalization of B-structures and T-structures.

The conditions of this step (iv) shall be "under binding conditions" that gives an effect corresponding to the effect in step (iii)—see above.

In the illustrative example of FIG. 1 herein—this step (iv) corresponds to the step "3 Emulsion w/o".

Step (iv) of first aspect further reads:

"wherein the compartmentalization system comprises at least 2 times more individual compartments than the Y number of T-structures present in step (iii)"

This may herein be seen as an essential step of the method as described herein—i.e. it is essential to have "at least 2 times more individual compartments than the Y number of T-structures present in step (iii)".

In the FIG. 1 herein—the in vitro compartmentalization system may be e.g. a water-in-oil emulsion system—as further discussed below herein suitable water-in-oil emulsion systems are well known in the art.

In the hypothetical theoretical illustrative example in FIG. 1 there is only one target in step (ii) [$T_n$ (n=1)] and there are 3 copies of each of the T-structure—i.e. the number "Y" is 3.

Accordingly, in this theoretical illustrative example of FIG. 1 there should be at least (2×3)=6 individual compartments (e.g. oil droplets) in the in vitro compartmentalization system—please note that in FIG. 1 herein are there less than 30 individual compartments (i.e. FIG. 1 is just an illustration of some of the elements of the method as described herein).

As discussed above—in practice there may be for instance at least $10^4$ copies of a T-structure of interest—i.e. Y could in this case be $10^4$ and there should in this case be at least $(2 \times 10^4) = 2 \times 10^4$ individual compartments (e.g. oil droplets) in the in vitro compartmentalization system.

An advantage of having this "at least 2 times more individual compartments than the Y number of T-structures" is that non-binders in the display library is randomly distributed in the compartments and therefore co-compartmentalize with the target in a random fashion, with a frequency depending on the ratio between the number of compartments and the number of target molecules (in this case 1 out of 10), whereas binders, due to the binding activity, will co-compartmentalize together with target molecules independently of the ratio between the number of compartments and the number of target molecules (in the ideal case 1 out of 1). Consequently, in this case binders will be enriched 2 fold when compared to non-binders.

In line of above one may say one gets an even better enrichment if there is relatively more individual compartments in the in vitro compartmentalization system—accordingly, in a preferred embodiment there is "at least 10 times more individual compartments than the Y number of T-structures present in step (iii)", more preferably there is "at least 100 times more individual compartments than the Y number of T-structures present in step (iii)", more preferably there is "at least 10 000 times more individual compartments than the Y number of T-structures present in step (iii)", more preferably there is "at least 100 000 times more individual compartments than the Y number of T-structures present in step (iii)", more preferably there is "at least 1 000 000 times more individual compartments than the Y number of T-structures present in step (iii)".

In a preferred embodiment of the present invention the number of compartments is larger than 2, 5, 10, 50, 100, 1000, 5000, 10 000, 50 000, 100 000, 500 000, 1 000 000, 5 000 000, or 10 000 000 times the Y number of T-structures of step (iii).

Step (iv) of first aspect further reads:

"under conditions wherein the B-structures, T-structures and BT-structures enter randomly into the individual compartments"

This should understood as the skilled person would understand it in the present context—relating to that in order to get the herein advantageous enrichment one needs to have conditions wherein the B-structures, T-structures and BT-structures enter randomly into the individual compartments.

Said in other words—the propensity for any B-structures, T-structures and BT-structures for being compartmentalized in any given compartment is dependent on the volume of said compartment and the total volume.

Said in other words—if virtually all the B-structures, T-structures and BT-structures would only enter into one specific individual compartment one will obviously not get the advantageous enrichment as discussed herein.

As discussed below—if one e.g. uses a suitable water-in-oil emulsion system as the in vitro compartmentalization system one can easily identify conditions, wherein the B-structures, T-structures and BT-structures enter randomly into the individual compartments (e.g. an individual oil droplets)—in fact it would be quite difficult to identify conditions, where it is not randomly—i.e. wherein virtually all the B-structures, T-structures and BT-structures would only enter into one specific individual compartment (e.g. an individual oil droplets).

In a preferred embodiment of step (iv)—there is at least square root 10 (3.16) times more individual compartments than the X number of B-structures in step (iii).

A Poisson distribution is assumed to describe the distribution of B-structures in the compartments. This implies that all compartments are of equal volumes. The probability that a compartment has n=0, 1, 2 or more B-structures molecules can be calculated using the formula:

$$f(n, \lambda) = \frac{e^{-\lambda} \lambda^n}{n!}$$

where I is the ratio between X number of B-structures and number of compartments. When I is square root 10 (3.16) less than 5% (4.1%) of the compartments will have more than one B-structures. This means that the effect of this is to lowering the enrichment of positive binding entity with less than 5%, which is insignificant in most cases.

As discussed above and as understood by the skilled person in the present context, the method of the first aspect may be seen as a method which implies that the $B_{BoundTo}$T-structures (i.e. the target-binding entity complexes) remain suspended in solution in the individual/separated compartments of step (iv) of the first aspect.

Accordingly, just to make it 100% clear, one may express this as that the method of the first aspect and herein relevant embodiments of this method, is a method wherein the $B_{BoundTo}$T-structures remain suspended in solution in the individual compartments of step (iv) of the first aspect.

Said in other words, the method does not rely on target immobilization on a solid support as for herein relevant prior art methods as discussed above.

In Vitro Compartmentalization System

As discussed above, a herein suitable in vitro compartmentalization system may e.g. be a water-in-oil emulsion system.

In case wherein the in vitro compartmentalization system is a water-in-oil emulsion system—one may say that the "applying an in vitro compartmentalization system . . . to the solution of step (iii)" of step (iv) may be expressed as "adding the solution of step (iii) to an water-in-oil emulsion system".

Herein suitable water-in-oil emulsion systems are described in the art e.g. Nat Methods. 2006 July; 3(7):545-50 (Williams et al), Nat Methods. 2006 July; 3(7):551-9 (Diehl et al), Proc Natl Acad Sci USA. 2003 Jul. 22; 100(15):8817-22 (Dressman et al), J Biotechnol. 2003 Apr. 24; 102(2):117-24. (Nakano et al), or Biomacromolecules. 6, 1824-1828 (2005) (Musyanovych et al).

As evident to the skilled person—in the case of using emulsions as the compartmentalization system and in analogy with similar size distributions, the compartment volume distribution is modeled as a log-normal distribution, also called a Galton distribution. By assuming a log-normal distribution and performing measurements of the actual droplet sizes the expected value (mean) and the standard deviation can be calculated for a specific experiment. According to this distribution, 95% of the compartment volumes will be within L logarithmic units from the mean (log) volume, where L is 1.96 times the standard deviation of the log-volumes.

In a preferred embodiment of the present invention the average compartments size, the variation, and the standard deviation is taken into account when analyzing the data.

In a preferred embodiment of the present invention compartments with a volume, larger than 2, 3, 4, 5, 6, 7, 8, 9, 10, 20, 30, 40, 50, 60, 70, 80, 90, or 100 times the average compartment size are removed from the experiment.

In a preferred embodiment of the present invention compartments with a volume, smaller than $1/100$, $1/90$, $1/80$, $1/70$, $1/60$, $1/50$, $1/40$, $1/30$, $1/20$, $1/10$, $1/9$, $1/8$, $1/7$, $1/6$, $1/5$, $1/4$, $1/3$, or $1/2$, times the average compartment size are removed from the experiment.

As evident to the skilled person—several technologies may be employed to exclude compartments from the experiment based on the volume of the compartments, for example by FACS sorting, equilibrium centrifugation, filtration, or microfluridic systems etc.

Alternatively, the in vitro compartmentalization system may be agarose droplet microfluidics. (Lab Chip. 2010 Sep. 13. [Epub ahead of print] Agarose droplet microfluidics for highly parallel and efficient single molecule emulsion PCR. Leng X, Zhang W, Wang C, Cui L, Yang C J).

Alternatively, the in vitro compartmentalization system may simply be to disperse the solution into e.g. "a micro titer plate" and of step (iii) is simply randomly putted into the individual wells (i.e. the individual compartments) of the micro titer plate—as known this may today be done rapidly and efficient by e.g. a suitable robot machine or an open well system. An example of such a system based on a high-density array of nanoliter PCR assays, functionally equivalent to a microtiter plate, the nanoplate system makes possible up to 3,072 simultaneous PCR reactions in a device, the size of a standard microscope slide (Methods Mol Biol. 2009; 496:161-74. (Brennan et al)).

Another example is a silicone device presenting a large array of micrometer-sized cavities, which can be used it to tightly enclose volumes of solution, as low as femtoliters, over long periods of time. The microchip insures that the chambers are uniform and precisely positioned (Nat Biotechnol. 2005 March; 23(3):361-5 (Rondelez et al)).

As evident to the skilled person—microfluridic devices can be employed in the in vitro compartmentalization system (For review see e.g. Angew Chem Int Ed Engl. 2010 Aug. 9; 49(34):5846-68 (Theberge et al)).

In a preferred embodiment of the present invention a suitable average compartments volume is less than $10^{-6}$ liter, less than $10^{-7}$ liter, less than $10^{-8}$ liter, less than $10^{-9}$ liter, less than $10^{-19}$ liter, less than $10^{-11}$ liter, less than $10^{-12}$ liter, less than $10^{-13}$ liter, less than $10^{-14}$ liter, less than $10^{-15}$ liter, less than $10^{-16}$ liter, less than $10^{-17}$ liter, less than $10^{-18}$ liter, less than $10^{-19}$ liter, less than $10^{-29}$ liter, less than $10^{-21}$ liter, or less than $10^{-22}$ liter.

As evident to the skilled person—the compartment volume cannot be infinitely small as the compartment should be larger than the molecules compartmentalized.

In short, the skilled person is aware of numerous different in vitro compartmentalization systems than could be of interest in the present context.

Step (v) of First Aspect

Step (v) of first aspect reads:

"fusing the nucleic acid molecules of a B-structure and a T-structure which are both present within the same individual compartment—i.e. fusing the nucleic acid molecule of the B-structure to the nucleic acid molecule of the T-structure"

A simple way to view this step is that the co-compartmentalization of B-structures and T-structures origination of (iv) is "transformed" into fused cognate genotypes.

In the present context "fusing the nucleic acid molecules of a B-structure and a T-structure" shall be understood as joining the genetic information carried by the two genotypes in the compartment.

As known to the skilled person, this can be accomplished in several ways such as e.g.:

a) information transfer by e.g. overlap PCR or overlap genome extension (overlap PCR without outer primers)—one strand originating from one genotype acts as a primer and uses a strand originating from the other genotype as a template;

b) information joining catalyzed by an enzyme forming an amplifiable facilitating bond—e.g. by a DNA ligase where a phosphordiester bond between at least one of the strands from each genome is form;

c) information joining catalyzed by an enzyme forming an non-amplifiable facilitating bond—e.g. having a moiety on each genome thus upon induction an enzyme capable of linking the two moieties between at least one of the strands from each genotype is form;

d) information joining not catalyzed by an enzyme—e.g. having a inducible chemical reactive group on each genome thus upon induction a chemical bond between at least one of the strands from each genotype is form; and e) information joining transient—e.g. having a affinity tag (these may be different or identical) on each genome thus by providing an agent with affinity for both tags a ternary complex containing both genotype is formed.

In the illustrative example of FIG. 1 herein—this step (v) corresponds to fusing the nucleic acid molecules of the B-structure and the T-structure present in the individual compartment number three from the left.

A herein very important advantage is that during this step one may say that the binding between the binding entity and target is no longer relevant—i.e. when one here performs the fusion of the nucleic acid molecules step one can do it under conditions, wherein one does not have to worry about this binding entity to target binding and spatial arrangements. A simple way to view this step is that the binding of target with binding entity origination from step (i) is now transformed into co-compartmentalization of B-structures and T-structures.

This may be seen as a very big advantage of the method as described herein.

For instance, if one wants to make the fusion of the nucleic acid molecules of the B-structure and the T-structure by hybridization of overlapping base pairing regions one can in this step (v) adequately change e.g. the temperature to get the relevant base pairing hybridization without being worried if the binding between the binding entity and target could be destroyed.

Accordingly, the step (v) may be performed under conditions, wherein there is essentially no binding of any of the binding entities of step (i) to any of the target(s) of step (ii).

As already discussed above—the fusing of the nucleic acid molecules of the B-structure and the T-structure may be done in different ways than e.g. by hybridization of overlapping base pairing regions.

For instance, if a e.g. a ligase enzyme is used in step (v) to get the fusing nucleic acid molecules—then one does not need to have any base pairing overlapping regions between the nucleic acid molecules (genotype) of the B-structures step (i) and the nucleic acid molecules (genotype) of the T-structures of step (ii).

As evident to the skilled person—if e.g. a ligase or a polymerase enzyme is used—this ligase enzyme should preferably have been added to the solution of step (iii) or during the optional diluting step (iii-b) in order to properly be present in the relevant individual compartments of step (v).

As evident to the skilled person—several different enzymatic reactions may be employed to fuse the genome—a large number enzymatic reactions have been reported in the literature e.g. Kabanov et al., Biochimica et Biophysica Acta, 996 (1989) 147-152, Salon et al. Biochemistry 1992, 31, 8072-8079, Anarbaev et al, Biochimica et Biophysica Acta 1384 1998. 315-324, Ong et al., (2006). J. Mol. Biol. 361: 537-50, Ghadessy, F. J. Ong, J. L. and Holliger, P. (2001). Proc. Natl. Acad. Sci. USA 98: 4552-4557, Protein Engineering, Design & Selection vol. 17 no. 3 pp. 201-204, 2004, Levy et al, RNA (2005), 11:1555-1562, Turner et al., Nucleic Acids Res. 2008 August; 36(13): e82.

In a preferred embodiment of the present invention the co-compartmentalized genotypes are fused by an enzyme.

As evident to the skilled person—despite the concentration of genotypes in the solution before compartmentalization may be very low e.g. picomolar-micromolar range the concentration of genotypes in a compartment with co-compartmentalized genotypes may be high e.g. when the compartment volume is in the femtoliter ($10^{-15}$ liters) range the concentration of the genotypes are in the nanomolar range ($10^{-9}$ M), when the compartment volume is in the attoliter ($10^{-18}$ liters) range the concentration of the genotypes are in the micromolar ($10^{-8}$ M) range, or when the compartment volume is in the zeptoliter ($10^{-21}$ liters) range the concentration of the genotypes are in the millimolar ($10^{-3}$ M) range. Consequently, the genotype concentration in a compartment may be controlled for facilitating enzymatic reactions and even traditional chemical reactions.

As evident to the skilled person—if e.g. inducible chemical cross-linking in emulsion is used—neither the inducer nor other reagents may be mandatory before compartmentalization as these may be "delivered" later to the formed compartments. For example inducers may be light, temperature or a chemical activator delivered though the continuous phase. Such embodiments may be advantageous when small compartments are desired.

In a preferred embodiment of the present new invention a chemical cross-linking is performed by Nucleophilic Substitution $S_N2$

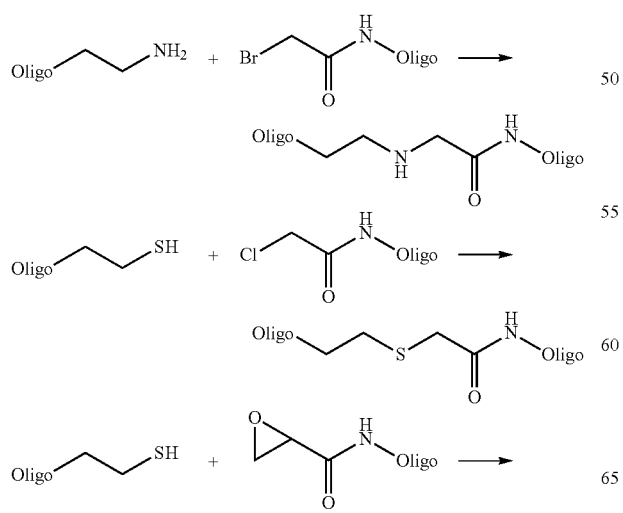

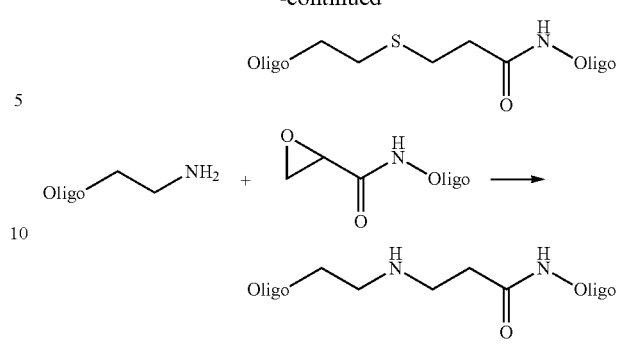

The nucleophilic substitution reaction can essentially be performed as described by:

Z. J. Gartner, et al. J. Am. Chem. Soc. 2001, 123, 6961.

In a preferred embodiment of the present new invention a chemical cross-linking is performed by Nucleophilic Aromatic Substitution

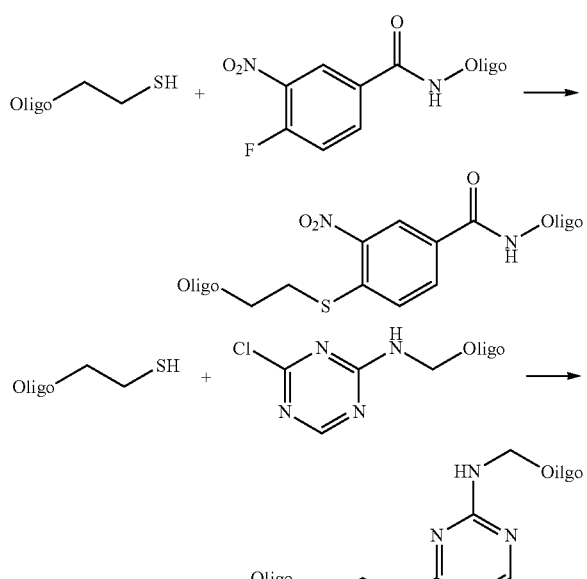

21
-continued

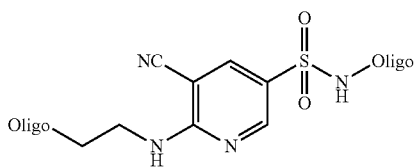

The nucleophilic aromatic substitution reaction can essentially be performed as described by: Clark et al, Nature Chemical Biology 5, 647-654 (2009)

In a preferred embodiment of the present new invention a chemical cross-linking is performed by Conjugate Addition

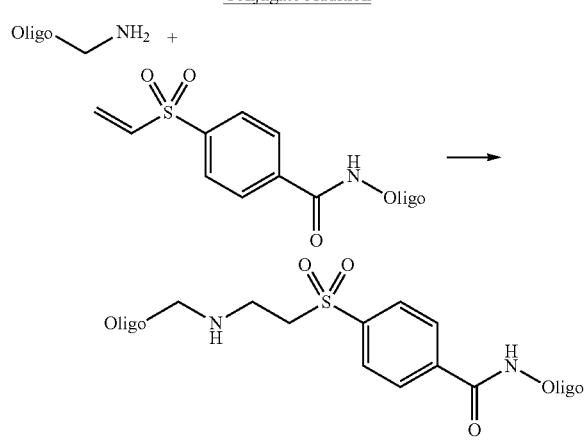

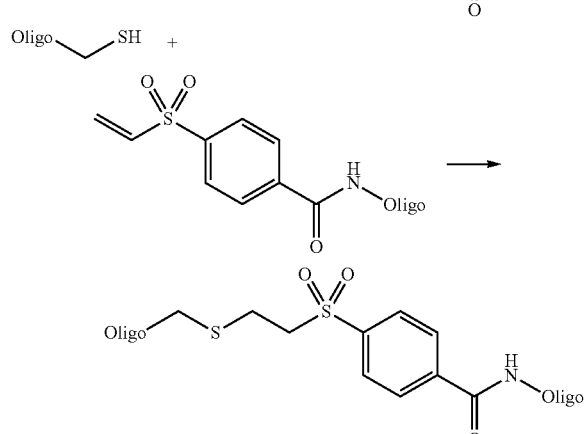

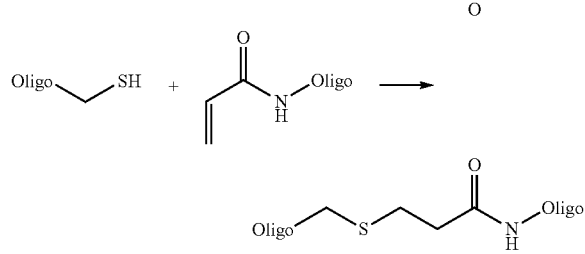

The nucleophilic substitution reaction can essentially be performed as described by:

Z. J. Gartner, et al. J. Am. Chem. Soc. 2001, 123, 6961.

In a preferred embodiment of the present new invention a chemical cross-linking is performed by

22

Reductive Amination

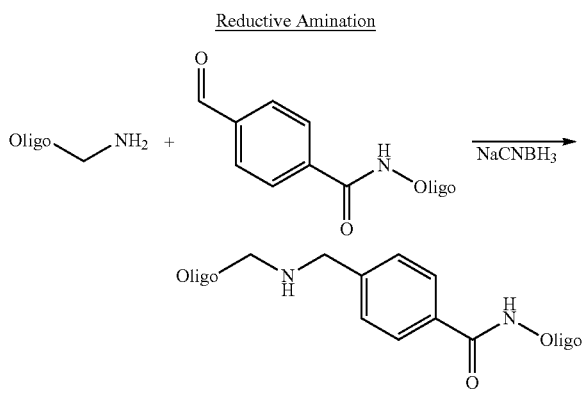

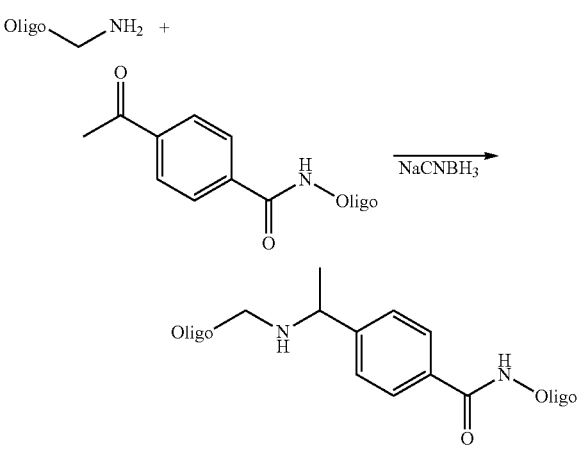

The reductive amination can essentially be performed as described by:

Z. J. Gartner, et al. Angew. Chem. Int. Ed. 2002, 41, 1796.

In a preferred embodiment of the present new invention a chemical cross-linking is performed by Amine Acylation

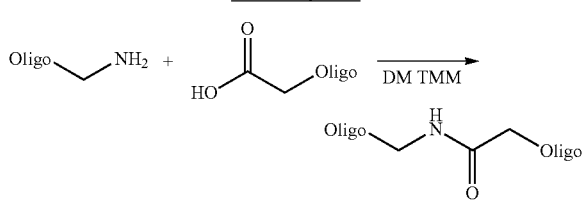

The Amine acylation can essentially be performed as described by:

Z. J. Gartner, et al. Angew. Chem. Int. Ed. 2002, 41, 1796.

In a preferred embodiment of the present new invention a chemical cross-linking is performed by Phosphoramidate formation

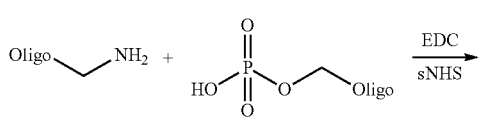

-continued

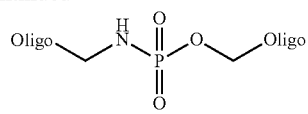

The Phosphoramidate formation can essentially be performed as described by:
Luther A, et al. Nature 1998, 396:245-248.

In a preferred embodiment of the present new invention a chemical cross-linking is performed by Aldol Condensation

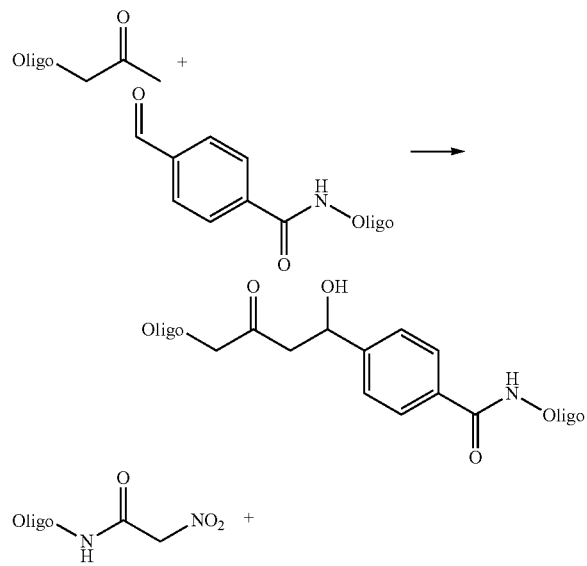

The Aldol condensation reaction can essentially be performed as described by:
Zhuo Tang et al. Angew. Chem. Int. Ed. 2007, 46, 7297-7300

In a preferred embodiment of the present new invention a chemical cross-linking is performed by Cycloaddition Crosslinks Diels-Alder Cycloaddition

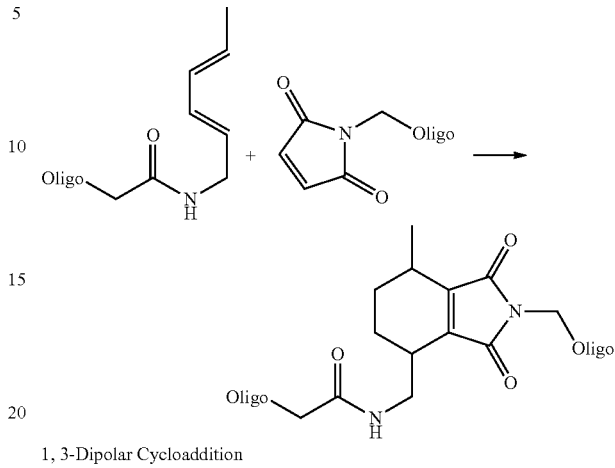

1, 3-Dipolar Cycloaddition

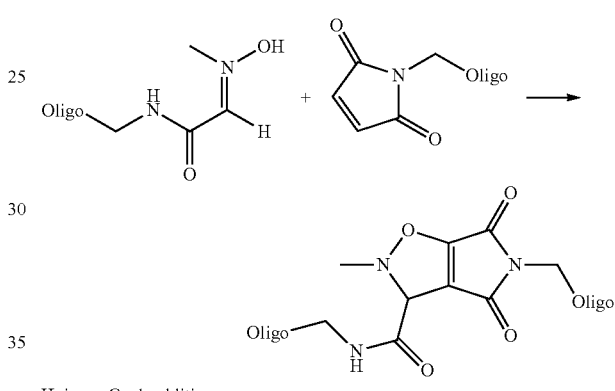

Huisgen Cycloaddition

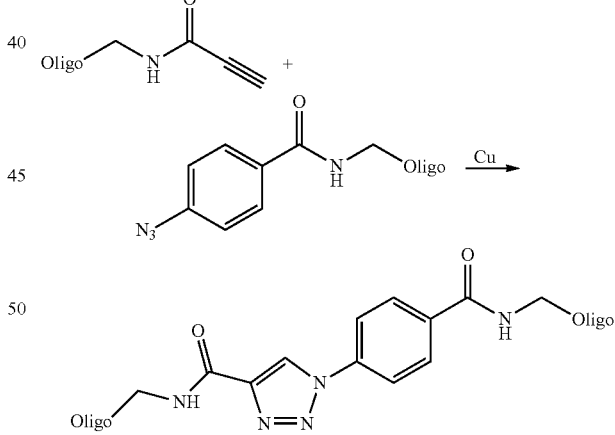

The Cycloaddition reactions can essentially be performed as described by:
Buller et al. Bioorganic & Medicinal Chemistry Letters 18 (2008) 5926-5931
Fujimoto K, J Am Chem Soc 2000, 122:5646-5647.
Gartner Z. J. et al. Angew Chem Int Ed Engl 2002, 41:1796-1800.
Gartner Z. J. et al. Angew Chem Int Ed Engl 2003, 42:1370-1375.
Poulin-Kerstien A. T. et al. J Am Chem Soc 2003, 125: 15811-15821.

In a preferred embodiment of the present new invention a chemical cross-linking is performed by Disulfide Crosslinks

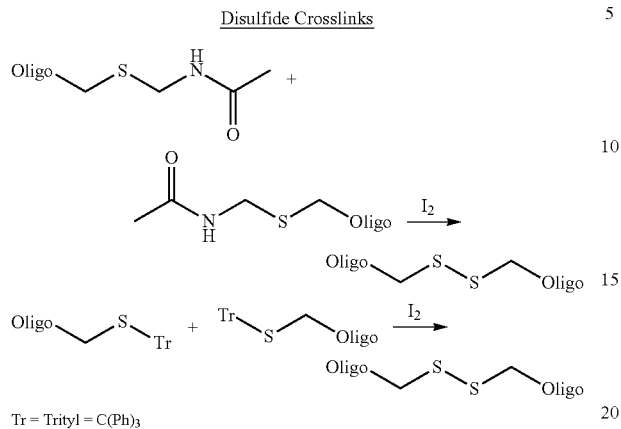

Tr = Trityl = C(Ph)₃

The Disulfide crosslink can essentially be performed as described by:

Mays, J. R. et al. Tetrahedron Lett. 2007, 48, 4579.

Theodoropoulos, D. et al. Journal of Medicinal Chemistry, 1985, vol. 28, 10, p. 1536-1539

Lorenz, Katrin B. et al. Journal of Organic Chemistry, 2004, vol. 69, 11 p. 3917-3927

In a preferred embodiment of the present new invention a chemical cross-linking is performed by Urea Croslinks

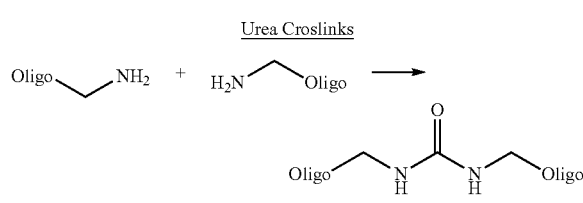

Coupling reagens: bis-(4-nitrophenyl)carbonate

The urea crosslink can essentially be performed as described by:

EP1809743B1 (Vipergen)

In a preferred embodiment of the present new invention a chemical cross-linking is performed by Olefination Crosslinks Wittig Olefination

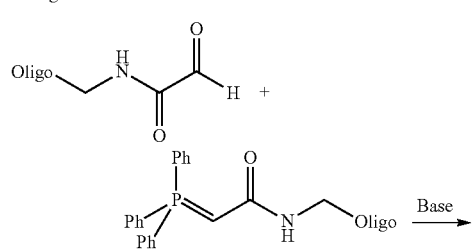

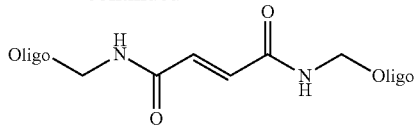

The Wittig olefination reaction can be performed as described by:

Gartner Z. J. et al. Angew Chem Int Ed Engl 2002, 41:1796-1800

In a preferred embodiment of the present new invention a chemical cross-linking is performed by Olefination Crosslinks Wittig Olefination

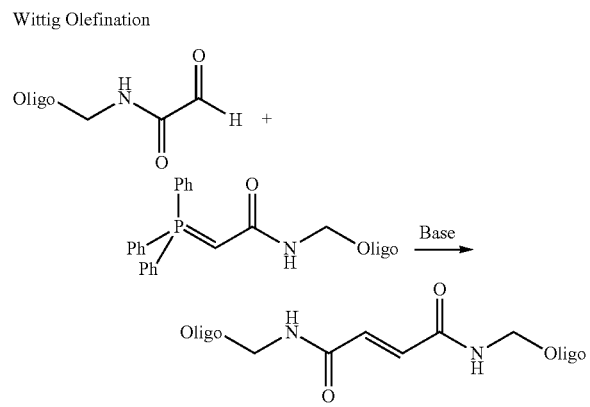

The Wittig olefination reaction can essentially be performed as described by:

Gartner Z. J. et al. Angew Chem Int Ed Engl 2002, 41:1796-1800.

In a preferred embodiment of the present new invention a chemical cross-linking is performed by Transition metal catalysed crosslink Heck Coupling

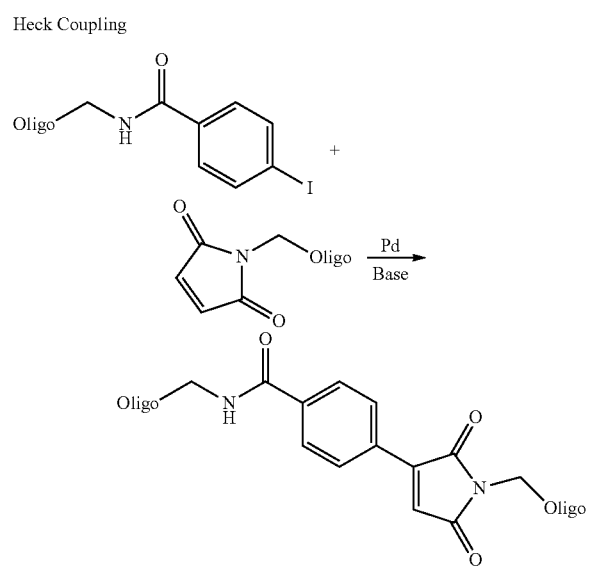

Sonogashira Coupling

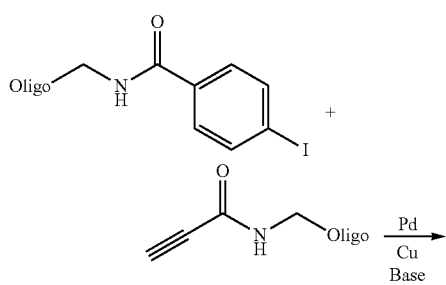

Suzuki Coupling

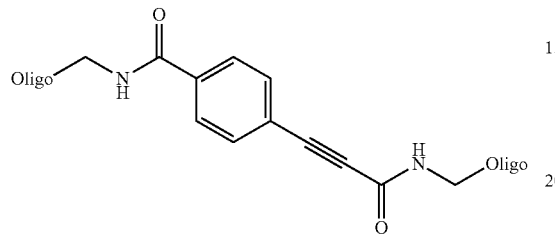

Alken-Alkyn Coupling

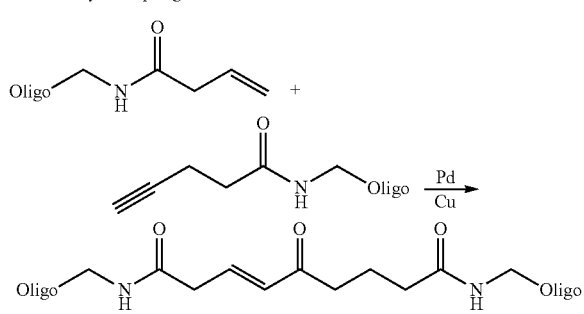

Transition metal catalysed reactions can essentially be performed as described by:
Czlapinski J. L. et al. J Am Chem Soc 2001, 123: 8618-8619.
Gartner Z. J. et al. Angew Chem Int Ed Engl 2002, 41: 1796-1800
Calderone C. T. et al. Angew Chem Int Ed Engl 2005, 44: 1-5

Kanan M. W. et al. Nature 431, 545-549, 2004

In a preferred embodiment of the present new invention a chemical cross-linking is performed by Photo Crosslinking

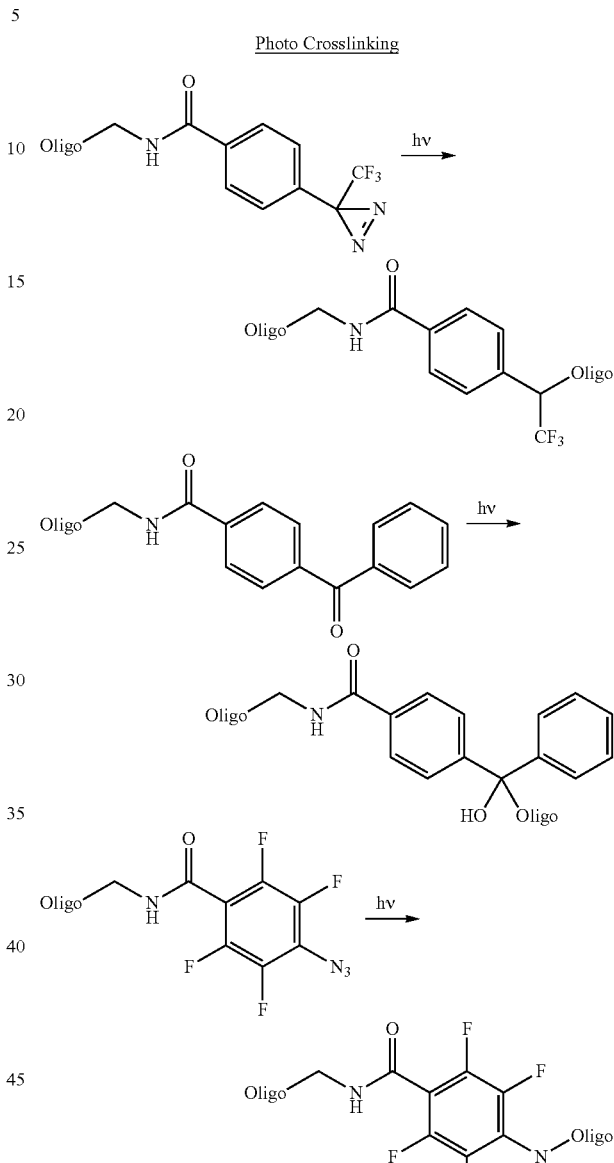

Photo crosslinking can essentially be performed as described by:
Quamrul, A. et al. Bioorganic & Medicinal Chemistry Letters 18 (2008) 5923-5925
Weber, T. et al. Journal of the American Chemical Society; 117; 11; (1995); 3084-3095
Chee, G. et al. Bioorganic and Medicinal Chemistry; 18; 2; (2010); 830-838
Nassal, M. Journal of the American Chemical Society; 106; (1984); 7540-7545
Pandurangi, R. S. et al. Bioorganic Chemistry; 25; 2; (1997); 77-87
Patent; KENT STATE UNIVERSITY; LELAND STANFORD JUNIOR UNIVERSITY; US2010/29952; (2010); (A1)

In short, the skilled person is aware of numerous different ways of fusing the nucleic acid molecules of a B-structure and a T-structure which are both present within the same individual compartment.

As understood by the skilled person in the present context—it is preferred that there is no herein significant fusion of the nucleic acid molecules of a B-structure and a T-structure in the steps (iii) and (iv) of the method of the first aspect—said in other words, there is preferably no significant creation of the $BT_{Fused}$-structures before step (v).

Step (vi) of First Aspect

Step (vi) reads:

"combining the content of the individual compartments of step (v) . . . "

It is evident that the "combining the content of the individual compartments of step (v)" is done in a suitable way depending on the in vitro compartmentalization system used in step (iv).

For instance, if the in vitro compartmentalization system used in step (iv) is a micro titer plate like format (see above) the content of the individual wells are simply combined (put together).

For instance, if the in vitro compartmentalization system used in step (iv) is a suitable water-in-oil emulsion—the individual oil compartments may simply be disrupted by e.g. centrifugation, increase the temperature or by adding a suitable organic solvent.

In short, in the present context it is routine work for the skilled person to combine the content of the individual compartments of step (v).

Step (vi) further reads:

" . . . under conditions wherein there is no fusing of the nucleic acid molecules of a B-structure and a T-structure—i.e. there is not created any new $BT_{Fused}$-structure not already created in step (v)—in order to get a library of $BT_{Fused}$-structures . . . "

As discussed above—one may say that the enrichment for the herein wanted $BT_{Fused}$-structures has already been obtained in the steps above—accordingly, as evident to the skilled person one is in this step not interested in creating more "new" $BT_{Fused}$-structures as such.

It is routine work for the skilled person to perform step (vi) under such conditions—for instance, if a ligase has been used in step (v) to obtain the wanted $BT_{Fused}$-structures, this ligase could be inactivated (e.g. by properly raising the temperature) before step (vi) is performed.

In view of the discussions herein—it is evident for the skilled person that this step (vi) will results in a library of $BT_{Fused}$-structures.

As evident to the skilled person—this library of $BT_{Fused}$-structures may be described as an enriched library of species of $BT_{Fused}$-structures, comprising nucleic acid sequence information allowing to identify the binding entity and the target—i.e. the sequence information of step (i) and (ii), originating from binding pairs of target and binder entity when compared to $BT_{Fused}$-structures originating from non-binding pairs of target and binder entity.

Optional Step (vii)—i.e. Subsequently Use of the Enriched Library of Step (iv) of First Aspect.

As discussed above—step (vii) is an optional step.

As described herein once one has obtained the enriched library of step (vi) one may use this library in different ways according to art—e.g. the enriched library may be considered as an enriched in vitro display library that e.g. can be used in a second round of selection/enrichment or one may identify the structure of a specific binding entity of interest directly from the enriched library of step (vi).

Accordingly, an embodiment of the invention relates to the method as described herein, wherein there is an extra step (vii) comprising use the enriched library of step (vi) to identify at least one individual binding entity that binds to at least one target of interest.

Purification of Fused Genotypes:

In a suitable embodiment of the present invention the fused genotypes (i.e. the $BT_{Fused}$-structures) may be purified.

The skilled person in the art can routinely identify numerous different strategies in order to purify the fused genotypes, without being limited for example by: agarose gel electrophoresis, polyacrylamide gel electrophoresis, spun-columns, enzymatic treatment, HPLC purified, affinity purified or capillary electrophoresis (Molecular Cloning: A Laboratory Manual (3-Volume Set), 3rd Edition, 2001-01 by Joseph Sambrook, David W. Russell, Publisher: Cold Spring Harbor Laboratory Press)

In a preferred embodiment of the present invention the fused genotypes are purified post compartmentalization e.g. by gel purification or enzymatic degradation of undesired nucleic acid species. For a skilled person in the art it is evident to design such procedures. For example in the case of using overlap PCR for genotype fusing the size of the genotypes may be chosen to facilitate gel purification e.g the length of the display library genotype could be chosen to around 250 bp and the length of the target genotype could be around 100 bp and the overlap region to be around 20 bases, the resulting fused genotypes will then be around 330 bp which are easily separated and purified from the original un-fused species by standard agarose gels electrotrophoresis or polyacrylamide gel electrotrophoresis. Furthermore, unused primers and ssDNA originating from primer extension using un-fused genotypes as templates may conveniently degraded enzymatically e.g. by ExoSAP-IT (Amersham Biosciences). Another example in the case of using ligase or chemical crosslinking or transient linking for genotype fusing the size of the genotypes may be chosen to facilitate gel purification e.g the length of the display library genotype could be chosen to around 250 bp and the length of the target genotype could be around 100 bp, the resulting fused genotypes will then be around 350 bp which are easily separated and purified from the original un-fused species by standard agarose gels electrotrophoresis or polyacrylamide gel electrotrophoresis In a preferred embodiment of the present invention the fused genotypes is gel purified.

In short, the skilled person is aware of numerous different ways of purifying fused nucleic acid molecules of a B-structure and a T-structure which was both present within the same individual compartment.

Polish Fused Genotypes:

In a preferred embodiment of the present invention the fused genotype may be polished (in cases where the genotypes are not fused by an approach compatible with DNA amplification), i.e. to form an amplifiable bond between the two genotypes in the fused genomes—an amplifiable bond is a phosphordiester bond (or alike) between a 3' end of one genotype with a 5' end of the other genotype in the fused genotype.

The skilled person in the art can routinely identify numerous different strategies in order to purify the fused genotypes, for example without being limited: enzymatically (e.g. E. coli DNA Ligase, Taq DNA Ligase, 9° N™ DNA Ligase, T4 DNA Ligase, T4 RNA Ligase 1 (ssRNA Ligase), T4 RNA Ligase 2 (dsRNA Ligase), T4 RNA Ligase 2, truncated) or chemically.

As evident to the skilled person—correct phosphordiester bond (or alike) formation between cognate genotypes (genotypes originating from the same compartment) post compartmentalization is easily controlled because these are pseudo-intramolecular reaction, thus, independent of concentration of the genotypes. In contrast, incorrect phosphordiester bond (or alike) formation between non-cognate genotypes is an intermolecular reaction, thus, dependent on the concentration of the genotypes.

In a preferred embodiment of the present invention a DNA ligase is used for polishing.

In short, the skilled person is aware of numerous different ways of polishing fused nucleic acid molecules of a B-structure and a T-structure which were both present within the same individual compartment.

Removal or Inactivation of the Target Attached to the Nucleic Acid

In a preferred embodiment of the present invention the target attached to the fused genotypes may be removed or inactivated.

The skilled person in the art can routinely identify numerous different strategies in order to remove or inactivate the target attached to the fused genotypes, for example without being limited: heat, protease treatment, 6 M Guanidinium chloride, or linker cleavage in case the target was attached by a cleavable linker, In a preferred embodiment of the present invention the target attached to the fused genotypes is removed or inactivated by heat protease treatment, or 6 M Guanidinium chloride.

In a preferred embodiment of the present invention the target attached to the fused genotypes is removed proteinase K treatment.

In a preferred embodiment of the present invention the target attached to the fused genotypes is removed displacement by primer extension.

In short, the skilled person is aware of numerous different ways of removing or destroying the target attached to the fused nucleic acid molecules of a B-structure and a T-structure which were both present within the same individual compartment.

Next Round of ECC:

In a preferred embodiment of the present invention the fused genotype may be subjected to a next round of ECC, i.e. in a next round the fused genotypes will be fused with the new target's genotype—the new target may be the same or a different type as the previous target.

The skilled person in the art can appreciate that the enriched library of fused genotypes of step (iv) is an in vitro display library.

In a preferred embodiment of the present invention the earlier round of ECC target attached to the nucleic acid is removed or destroyed prior to a next round of ECC.

In a preferred embodiment of the present invention the target in a next round of ECC is the same as in an earlier round of ECC.

In a preferred embodiment of the present invention the target in a next round of ECC is not the same as in an earlier round of ECC.

In a preferred embodiment of the present invention the genotype of the target in a next round of ECC is fused to a free terminus end of the original genotype for the binding entity.

In a preferred embodiment of the present invention the genotype of the target in a next round of ECC is fused to a free terminus end of a target genotype from an earlier round of ECC.

Traditional Selection/Enrichment Methods:

In a preferred embodiment of the present invention the fused genotype may be subjected to a round of prior art known traditional selection/enrichment methods.

In a preferred embodiment of the present invention the earlier round of ECC target attached to the nucleic acid is removed or destroyed prior to a round of traditional selection/enrichment methods.

The skilled person in the art can routinely identify numerous different strategies in order to perform a round of a round of traditional selection/enrichment methods, for example without being limited: EP1809743B1 (Vipergen), EP1402024B1 (Nuevolution), EP1423400B1 (David Liu), Nature Chem. Biol. (2009), 5:647-654 (Clark), WO 00/23458 (Harbury), Nature Methods (2006), 3(7), 561-570, 2006 (Miller), Nat. Biotechnol. 2004; 22, 568-574 (Melkko), Nature. (1990); 346(6287), 818-822 (Ellington), or Proc Natl Acad Sci USA (1997). 94 (23): 12297-302 (Roberts).

In short, the skilled person is aware of numerous different ways to perform a round of traditional selection/enrichment methods of the library of fused nucleic acid molecules of a B-structure and a T-structure which was both present within the same individual compartment.

Amplification of Fused Genotypes:

In a preferred embodiment of the present invention the nucleic acid in the fused genotypes may be amplified—i.e. the $BT_{Fused}$-structures present in the enriched library of step (vi) may be amplified.

The skilled person in the art can routinely identify numerous different strategies in order to amplify the nucleic acid in the fused genotypes, for example without being limited: PCR (U.S. Pat. No. 4,683,202; Mullis), Emulsion PCR (Nakano et al., J Biotechnol. 2003; 102(2):117-24), Digital PCR (Vogelstein, B; Kinzler K W (1999). "Digital PCR". Proc Natl Acad Sci USA. 96 (16): 9236-41), NASBA (Compton J. Nucleic acid sequence-based amplification. Nature. 1991; 350(6313):91-2), or Rolling Circle Amplification (American Journal of Pathology. 2001; 159:63-69)

In a preferred embodiment of the present invention the nucleic acid in the fused genotypes is amplified subsequently to the de-compartmentalization step.

In a preferred embodiment of the present invention the nucleic acid in the fused genotypes is amplified subsequently to the compartmentalization step performed by PCR.

In a preferred embodiment of the present invention the nucleic acid in the fused genotypes is amplified subsequently to the compartmentalization step performed by PCR, where the forward PCR priming site is in the B-structure genotype and the backward priming site is in the T-structure genotype.

In a preferred embodiment of the present invention the nucleic acid in the fused genotypes is amplified subsequently to the compartmentalization step performed by PCR where the forward PCR priming site is in the B-structure genotypes and a part of the backward priming site is in the first T-structure genotypes and the remaining part is in the second T-structure genotype.

In a preferred embodiment of the present invention the nucleic acid in the fused genotypes is amplified subsequently to the compartmentalization step performed by PCR where the forward PCR priming is in the first T-structure genotypes site and part of the backward priming site is in the B-structure genotypes and the remaining part is in the second T-structure genotype.

In a preferred embodiment of the present invention the nucleic acid in the fused genotypes is amplified subsequently to the compartmentalization step performed by PCR where part of the forward PCR priming is in the first T-structure genotypes site and the remaining part of the forward PCR priming is in the B-structure genotypes and a part of the backward priming site is in the B-structure genotypes and the remaining part is in the second T-structure genotype.

In a preferred embodiment of the present invention the nucleic acid in the fused genotypes is amplified subsequently to the compartmentalization step performed by PCR where the forward PCR priming site is in the B-structure genotypes and 30-70% of the backward priming site is in the first T-structure genotypes and the remaining 30-70% is in the second T-structure genotype.

In a preferred embodiment of the present invention the nucleic acid in the fused genotypes is amplified subsequently to the compartmentalization step performed by PCR where the forward PCR priming is in the first T-structure genotypes site and 30-70% of the backward priming site is in the B-structure genotypes and the remaining 30-70% is in the second T-structure genotype.

In a preferred embodiment of the present invention the nucleic acid in the fused genotypes is amplified subsequently to the compartmentalization step performed by PCR where 30-70% of the forward PCR priming is in the first T-structure genotypes site and the remaining 30-70% of the forward PCR priming is in the B-structure genotypes and 30-70% of the backward priming site is in the B-structure genotypes and the remaining 30-70% is in the second T-structure genotype.

In short, the skilled person is aware of numerous different ways of amplifying the nucleic acid in fused nucleic acid molecules of a B-structure and a T-structure which was both present within the same individual compartment.

Translation:

In a preferred embodiment of the present invention the nucleic acid of fused genotypes may be amplified and subjected to a translation process where the library of enriched fused genotypes is translated into a new enriched in vitro display library.

The skilled person in the art can routinely identify numerous different strategies in order to amplify and subject the fused genotypes to a translation process, for example without being limited: EP1809743B1 (Vipergen), EP1423400B1 (David Liu), WO 00/23458 (Harbury), Nature Methods (2006), 3(7), 561-570, 2006 (Miller), Nature. (1990); 346 (6287), 818-822 (Ellington), or Proc Natl Acad Sci USA (1997). 94 (23): 12297-302 (Roberts).

In short, the skilled person is aware of numerous different ways to amplify and perform a translation process of nucleic acid molecules of a B-structure and a T-structure which was both present within the same individual compartment.

Analysis for Identities and Composition:

In a preferred embodiment of the present invention the nucleic acid of the fused genotype may be analyzed for identities and composition.

The skilled person in the art can routinely identify numerous different strategies in order to analyzed for identities of the nucleic acid of the fused genotypes, for example without being limited: sequencing (for review: Metzker, Michael L. (2010). "Sequencing technologies—the next generation". Nat Rev Genet 11 (1): 31-46.), DNA hybridization technologies (Science 270 (5235): 467-470), restriction enzyme digest, PCR, methods in EP1809743B1 (Vipergen), EP1402024B1 (Nuevolution), EP1423400B1 (David Liu), Nature Chem. Biol. (2009), 5:647-654 (Clark), WO 00/23458 (Harbury), Nature Methods (2006), 3(7), 561-570, 2006 (Miller), Nat. Biotechnol. 2004; 22, 568-574 (Melkko), Nature. (1990); 346(6287), 818-822 (Ellington), or Proc Natl Acad Sci USA (1997). 94 (23): 12297-302 (Roberts), WO06053571A2 (Rasmussen).

In a preferred embodiment of the present invention the nucleic acid of the fused genotype may be analyzed for identities and composition by DNA sequencing.

In a preferred embodiment of the present invention the nucleic acid of the fused genotype may be analyzed for identities and composition by DNA sequencing using the 454 technology (Margulies M, Egholm M, Altman W E, et al (September 2005). "Genome sequencing in microfabricated high-density picolitre reactors". Nature 437 (7057): 376-80).

In short, the skilled person is aware of numerous different ways for analysis for identities and composition of the nucleic acid of the fused genotype of a B-structure and a T-structure which was both present within the same individual compartment.

A Separate Independent Aspect of the Invention

A separate independent aspect of the invention is described below.

As understood by the skilled person—the method of this separate independent aspect of the invention uses the same basic technical principles as described above for the first aspect of the invention and thereto related embodiments.

In line of this and as understood by the skilled person—specific preferred embodiments of the first aspect of the invention (such as e.g. that the in vitro compartmentalization system of step (iv) is a water-in-oil emulsion system) may also be corresponding preferred embodiments of this separate independent aspect of the invention.

Accordingly, a separate independent aspect of the invention relates to a method for making an enriched library comprising specific nucleic acid sequence information allowing to identifying at least one binding entity that binds to at least one target wherein the specific binding entity has been present in an in vitro display library and wherein the method comprises the steps of:

(i): making an in vitro display library of at least 100 different binding entities ($B_n$ (n=100 or more), wherein each binding entity is attached to a nucleic acid molecule and the nucleic acid molecule comprises specific nucleic acid sequence information allowing to identify the binding entity—i.e. once one knows the specific nucleic acid sequence information of the nucleic acid molecule one directly knows the structure of the specific binding entity attached to the nucleic acid molecule—the structure of the binding entity (i.e. phenotype) attached to the nucleic acid molecule (genotype) is herein termed B-structure;

(ii): making structures with one target T attached to an enzyme capable of fusing two DNA molecules, wherein the target is capable of binding to at least one of the binding entities present in the library of step (i)—the structure of the target attached to the enzyme capable of fusing two DNA molecules is herein termed T-structure;

and wherein the method is characterized by that:

(iiia): mixing a solution comprising X (X is a number greater than $10^4$) numbers of B-structures of the library of step (i) with a solution comprising Y (Y is a number greater than $10^2$) numbers of T-structures of step (ii) under binding conditions, i.e. conditions where a B-structure containing a binding entity capable of binding to a target molecule, binds more efficiently to the corresponding T-structure, than a B-structure containing a binding entity not capable of binding to the same target do and wherein one gets binding of at least one of the binding entities to at least one target thereby creating a complex comprising a B-structure bound to a T-structure (herein termed $B_{BoundTo}$T-structure);

(iiib): mixing to the solution of step (iiia) a solution comprising at least 2 times more nucleic acid molecules than the Y number of T-structures present in step (iiia), wherein the nucleic acid molecules comprise specific nucleic acid sequence information allowing to identify the specific target (herein termed Target-DNA);

(iv): applying an in vitro compartmentalization system—under binding conditions, i.e. conditions where a B-structure containing a binding entity capable of binding to a target molecule, binds more efficiently to the corresponding T-structure, than a B-structure containing a binding entity not capable of binding to the same target do—wherein the compartmentalization system comprises at least 2 times more individual compartments than the Y number of T-structures present in step (iii) under conditions wherein the B-structures, T-structures, $B_{BoundTo}$T-structures and Target-DNA enter randomly into the individual compartments; and (v): fusing the nucleic acid molecules of a B-structure and a Target-DNA which are both present within the same individual compartment—this structure is herein termed $BT_{Fused}$-structure and the $BT_{Fused}$-structure comprises the specific nucleic acid sequence information allowing to identify the binding entity of step (i) and the specific nucleic acid sequence information allowing to identify the specific target of step (ii); and (vi): combining the content of the individual compartments of step (v) under conditions wherein there is no fusing of the nucleic acid molecules of a B-structure and a T-structure—i.e. there is not created any new $BT_{Fused}$-structure not already created in step (v)—in order to get a library of $BT_{Fused}$-structures, wherein the library is an enriched library of species of $BT_{Fused}$-structures originating from binding pairs of target and binder entity when compared to $BT_{Fused}$-structures originating from nonbinding pairs of target and binder entity.

As known to the skilled person—suitable examples of an enzyme capable of fusing two DNA molecules are e.g. a ligase or a polymerase.

In line of above discussion of the first aspect of the invention and herein relates embodiment to this—it may be preferred that the herein relevant nucleic acid molecules are DNA molecules and in line of this it may be preferred that the ligase or polymerase is a DNA ligase or a DNA polymerase.

As understood by the skilled person in the present context—the fusing of the nucleic acid molecules of a B-structure and a Target-DNA of step (v) of this separate independent aspect of the invention is done by the enzyme capable of fusing two DNA molecules (e.g. a ligase or a polymerase) as present in the T-structure of step (ii) of this separate independent aspect of the invention.

Contrary to the method of the first aspect as discussed herein (wherein there may be more than one different target T present)—there is only one target T present in this separate independent aspect of the invention.

Accordingly, the specific nucleic acid sequence information allowing identifying the specific target of the nucleic acid molecules of step (iiib) of this separate independent aspect of the invention may simply be a herein relevant characterizing single sequence.

In line of above discussion of the first aspect of the invention it is preferred that this specific nucleic acid sequence information allowing to identify the specific target is a PCR amplifiable sequence, since the $BT_{Fused}$-structure of step (v) can then be PCR amplified.

EXAMPLES

Example 1

Enrichment by Co-Compartmentalization Using Overlap ePCR for Genetype-Genotype Fusion—Spiking Experiment.

Figure 2:
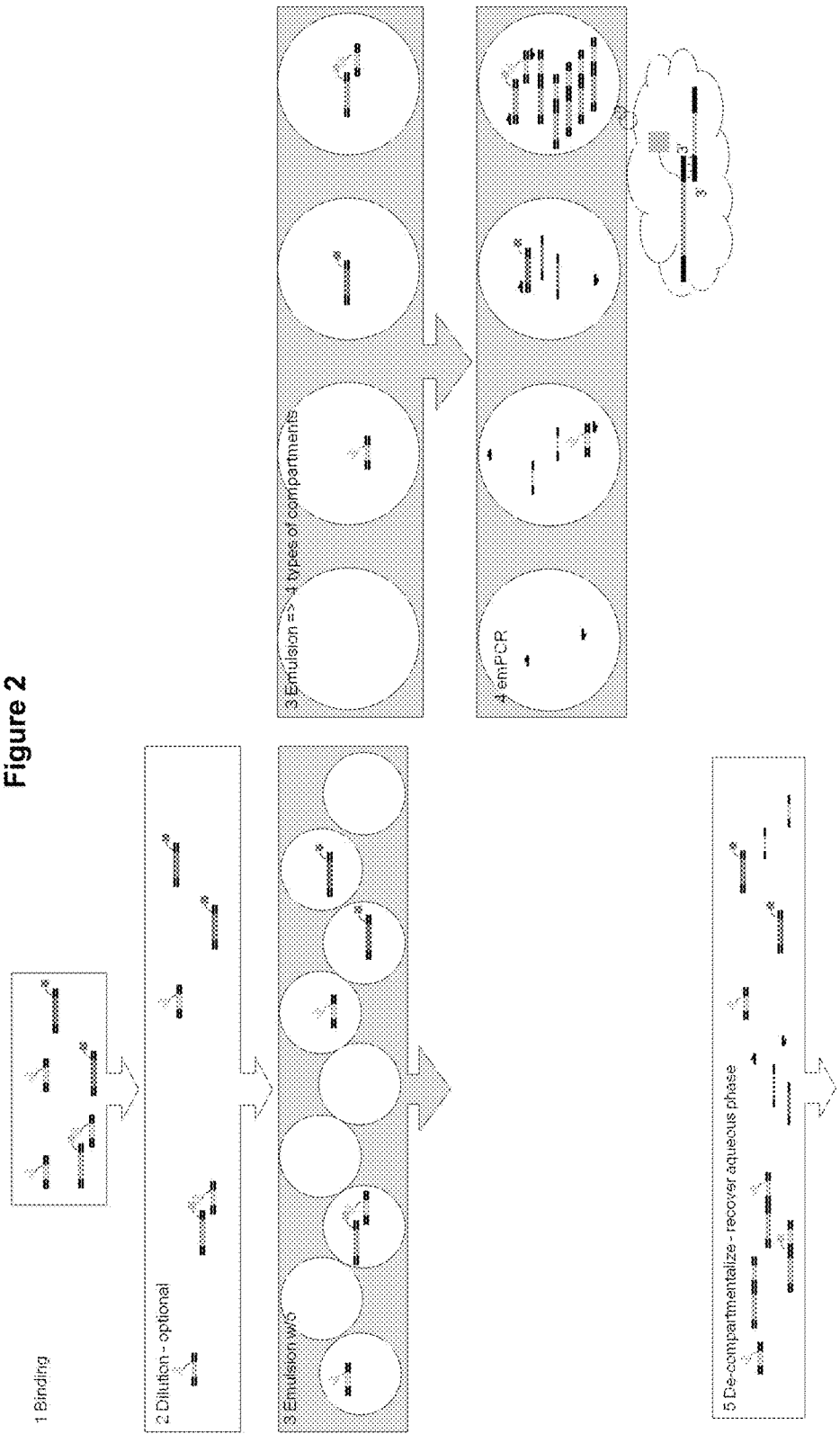
Figure 3:
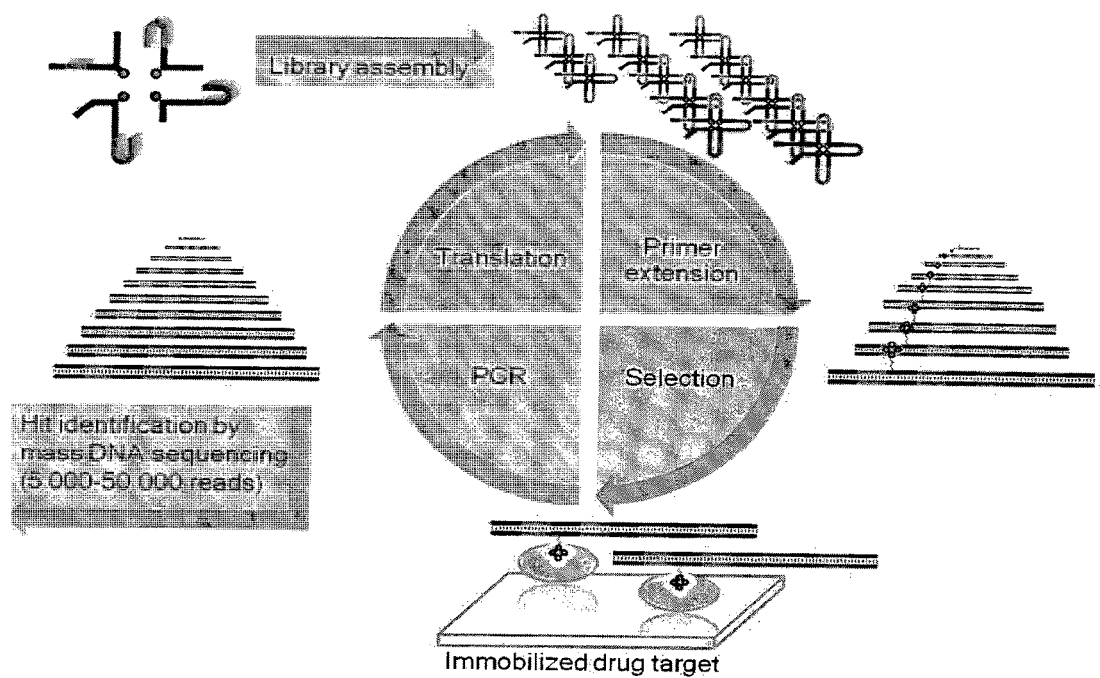

For overview see FIG. 2.
Methods
DNA Oligonucleotides Used
Continuous strand of DNA analogue to the yoctoreactor [Hansen et al. J. Am. Chem. Soc., 2009, 131 (3), pp 1322-1327]:

```
                                          (SEQ ID NO: 1)
CGCTAAtggtccctggcagtctccTTAGCGgaccGACTCcTgctcGAAGA CAACGGTgttttacACCGTTGTCTTCgagcTgtACCTGCgcAAGTGCgtt ttacGCACTTgcGCAGGTacTgtGCATCgacAAGACCgttttacGGTCTT gtcGATGCacTgGAGTCggtcCTGTTCGATCTTGGGCGTAT vip1461:
                                          (SEQ ID NO: 2)
ATACGCCCAAGATCGAACAG vip2501:
                                          (SEQ ID NO: 3)
x-TGGTCCCTGGCAGTCTCC  (x = 5'-biotin-TEG)

vip2504:
                                          (SEQ ID NO: 4)
CTGTTCGATCTTGGGCGTATGAGAAGAGCCAGAAACGTGGCTTCAGGCAC
CAAGGAAGAC vip2512:
                                          (SEQ ID NO: 5)
GCCTTGCCAGCCCGCTCAGGCAAGTCTTACAGCCGATCAGTCTTCCTTGG
TGCCTGAAG vip2502:
                                          (SEQ ID NO: 6)
CTGTTCGATCTTGGGCGTAT vip2500:
                                          (SEQ ID NO: 7)
x-GCCTTGCCAGCCCGCTCAG  (x = 5' carboxyl)

vip157:
                                          (SEQ ID NO: 8)
GCCTTGCCAGCCCGCTCAG vip660:
                                          (SEQ ID NO: 9)
TGGTCCCTGGCAGTCT vip1481:
                                          (SEQ ID NO: 10)
GAACAGGACCGA vip1471:
                                          (SEQ ID NO: 11)
CTGTTCGATCTTGGGCGTAT
```

Preparation of Yoctoreactor Library

The library is constructed according to Hansen et al. J. Am. Chem. Soc., 2009, 131 (3), pp 1322-1327) with the following modification: The splint oligonucleotide vip1481 (SEQ ID NO:10) and the oligonucleotide vip1471 (SEQ ID NO:11) are used for introducing the backward priming site.

Preparation of Known Target Binder (Biotin) Attached to Encoding DNA

A continuous stranded DNA analogue to the yoctoreactor library sequences is used for PCR using the vip1461 (SEQ ID NO: 2) primer and the vip2501 (SEQ ID NO:3) primer, which has a 5'-biotin. Thus, a 5'-biotin is introduced in the yoctoreactor DNA analogue (SEQ ID NO:1).

Protocol

PCR mixture:

50 µL 2×PCR mastermix (40 mM Tris-HCl, 20 mM $(NH_4)_2SO_4$, 20 mM KCl, 16 mM $MgSO_4$, 0.2% Triton X-100, 0.2 mg/mL BSA, 0.4 mM each of dATP, dTTP, dGTP, and dCTP, pH 8.8 @ 25° C.)

10 µL 5M Betaine (final conc. 0.5M)

1 µL 50 µM vip2501 (SEQ ID NO:3) (final conc 0.5 µM)

1 µL 50 µM vip1461 (SEQ ID NO: 2) (final conc. 0.5 µM)

1 µL ($10^7$ molecules) of continuous stranded DNA analogue to the yoctoreactor

1 µL (2 u/µL) Vent (exo-) polymerase

36 µL water

The mixture is subjected to thermal cycling by applying the following program in a PCR machine:

92 degrees 2 min, 25 cycles of (92 degrees 30 seconds, 72 degrees 1 min), 72 degrees 2 min), 72 degrees for 2 min.

The 185 bp DNA fragment is purified by PAGE purification according to standard procedure (Molecular Cloning: A Laboratory Manual (3-Volume Set), 3rd Edition, 2001-01 by Joseph Sambrook, David W. Russell, Publisher: Cold Spring Harbor Laboratory Press) and ethanol precipitated Preparation of Target DNA (TD)

The 99-mer target DNA is prepared in a one-step overlapping PCR protocol and subsequently purified on a 10% TBE-PAGE native gel Protocol PCR mixture:

50 µL 2×PCR mastermix (40 mM Tris-HCl, 20 mM $(NH_4)_2SO_4$, 20 mM KCl, 16 mM $MgSO_4$, 0.2% Triton X-100, 0.2 mg/mL BSA, 0.4 mM each of dATP, dTTP, dGTP, and dCTP, pH 8.8 @ 25° C.)

10 µL 5M Betaine (final conc. 0.5M)

1 µL 50 µM vip2500 (final conc 0.5 µM) (SEQ ID NO:7)

1 µL 50 µM vip2502 (final conc. 0.5 µM) (SEQ ID NO:6)

1 µL 20 pM vip2504 (SEQ ID NO:4) (final concentration 0.2 pM)

1 µL 20 pM vip2512 (SEQ ID NO:5) (final concentration 0.2 pM)

1 µL (2 u/µL) Vent (exo-) polymerase

35 µL water

The mixture is subjected to thermal cycling by applying the following program in a PCR machine:

92 degrees 2 min, 25 cycles of (92 degrees 30 seconds, 72 degrees 1 min), 72 degrees for 2 min.

The 99 bp DNA fragment is purified by PAGE purification according to standard procedure (Molecular Cloning: A Laboratory Manual (3-Volume Set), 3rd Edition, 2001-01 by Joseph Sambrook, David W. Russell, Publisher: Cold Spring Harbor Laboratory Press). and ethanol precipitated DNA—Target Conjugation Materials 1-Ethyl-3-[3-dimethylaminopropyl]carbodiimide hydrochloride (EDC, 100 mM stock freshly prepared, Aldrich E6383)

N-Hydroxysulfosuccinimide (s-NHS, 200 mM stock, Aldrich 56485)

Morpholinoethanesulfonic acid, MES buffer pH 6.0, 500 mM beta-Mercaptoethanol, 500 mM stock PCR product with 5' carboxyl group on lower strand (see above)

Streptavidin protein (AbCam 78833) (Target protein)

Protocol

The carboxyl modified oligonucleotide (ssDNA) or PCR product with terminal carboxyl can be pre-activated using EDC/s-NHS system prior to reaction with target protein (see refs for examples of activation of various types of carboxyls). Exposure of target protein to EDC may render it inactive, e.g. by chemically modifying tyrosine or cysteine residues. Thus, before mixing the activated DNA-carboxyl with target protein, residual EDC optionally may be quenched by addition of e.g. beta-mercaptoethanol to a final concentration of 20 mM.

Example Pre-Activation Mixture

|  | Final conc |
|---|---|
| 10 µL DNA (ssDNA or dsDNA) | |
| 10 µL 500 mM MES, pH 6 | 100 mM |
| 2.5 µL 100 mM EDC | 5 mM |
| 2.5 µL 200 mM s-NHS | 10 mM |
| 25 µL water | |
| Total 50 µL | |

Carboxylic acid activation is allowed to incubate at 20 C for 15-30 min.

Optional: To quench residual EDC, 2 µL of 500 mM beta-mercaptoethanol in water was added (final conc. 20 mM).

Subsequently, the s-NHS-activated ester should be used immediately.

Test of Pre-Activation

An aliquot of the preactivation mixture (25 pmoles ssDNA) can be diluted with water and a 1% phenethylamine in MeCN (primary amine that quenches the activated ester). This mixture can be allowed to react for 15 min, followed by precipitated using EtOH. After dissolution in 100 mM triethylammonium acetate (TEAA, pH 7), the DNA product can be analyzed by RP-HPLC using a gradient of MeCN in 100 mM TEAA.

Shift from initial retention time to higher retention time indicates 1) transformation of carboxyl→NHS ester and 2) subsequent reaction with amine.

Reaction with Target Protein

Check enzyme shipment buffer composition for primary amines. This protocol should tolerate the presence of e.g. DTT or EDTA in the protein stock solution, but primary amines must be removed e.g. by dialysis. Primary amines will quench the activated ester thus abolishing DNA—protein cross-link.

Otherwise, mix pre-activation mixture and enzyme as concentrated as possible to drive chemical reactions.

This should be allowed to incubate for 1-2 h at 20 C (possibly overnight in cases of slow reaction) then purify DNA—protein complex by e.g. electrophoresis.

Association Mixture

A diverse YoctoReactor library consisting of $10^6$ different molecules and a total of $10^9$ molecules i.e. potential ligands coupled to double stranded (ds) DNA, is spiked with $10^6$ biotin molecules coupled to ds DNA (known target binder). The spiked library is mixed with $10^7$ molecules streptavadin coupled to dsDNA (target attached to DNA). The molecules in the mixtures are allowed to associate in a total volume of 3 µl Binding Buffer (PBS, 0.05% tween 20, 0.2% BSA for 1 hour at room temperature to reach equilibrium. The concentration of streptavidin (the target) is around 6 pM which is more that 100 fold more than the reported $K_d$ of the biotin-streptavidin complex of ~$10^{-14}$ mol/L, which means that practical all biotin will be streptavidin bound at equilibrium.

PCR mixture 67 mM Tris-HCl (pH 8.8), 16.6 mM $NH_4SO_4$, 6.7 mM $MgCl_2$, 10 mM 2-mercaptoethanol, 1 mM of each dNTP, 7.5 µM of each primer (vip157 (SEQ ID NO: 8) and vip660 (SEQ ID NO:9)), 45 units of Taq polymerase in a total volume of 610 µl Emulsion PCR Two mL of an emulsion consisting of approx. $5 \times 10^9$ compartments per ml is prepared by a method similar to the method described by Dressman et al., 2003.

The DNA fragments coupled to the target (streptavadin) or ligands (non-binding or binding), respectively, have overlapping regions resulting in the potential assembly of the three fragments to combined fragments i.e. two types of combined fragment may be generated through assembly PCR per mixture; fragment (A) signifies that Streptavadin and Biotin have been present in the same compartment and fragment (B) signifies that Streptavadin and a random library molecule (not biotin linked) have been present in the same compartment. The two types of fragments can be differentiated through sequencing or restriction site digestion.

One mL and 500 µL (1.5 mL) continuous phase is prepared by dissolving 4.5% (vol/vol) Span80 in mineral oil, followed by 0.40% (vol/vol) Tween80 and 0.05% (vol/vol) Triton X-100 under constant stirring (1,400 rpm) in a 5 ml round bottom Cryo vial, using a magnetic stirring bar with a pivot ring. The continuous phase is split into two times 600 µL in separate 5 ml round bottom Cryo vials.

The aqueous phase is made by adding 597 µl PCR mixture to the 3 µL association mixture. Three hundred (300) µL of the aqueous phases is gradually added (10 µL every 15 s) to each of the two continuous phases under constant stirring (1400 rpm) using a magnetic stirring bar with a pivot ring. After addition of the aqueous phases, the stirring is continued for 30 min.

The emulsions are aliquoted into approx. twenty wells of a 96-well PCR plate, each containing 100 µL. The amplification program comprises of 30 cycles with the following steps: initial denaturation at 92° C. for 2 min; 20 cycles consisting of dsDNA denaturation at 92° C. for 30 s, primer annealing and extension at 72° C. for 2 min and 30 s; and final elongation at 72° C. for 2 min.

Breaking the Emulsion

The DNA fragments from the emulsion PCR are rescued by pooling the emulsions and centrifuging at 13,000 g for 5 min at 25° C. The oil phase is discarded. Residual mineral oil and surfactants are removed from the emulsion by performing the following extraction twice: add 1 ml of water-saturated diethyl ether, vortex the tube, and dispose of the upper (solvent) phase.

Anticipated Results

Assuming; equal size spherical compartments, random distribution of molecules and complex in compartments, 100% association of Streptavadin-Biotin complex, no dissociation of Streptavadin-Biotin complex, assuming none or few binders with adequate binding affinity for streptavidin in the yR library, no bias of the PCR reaction, and 100% reaction efficiency in "primer extension" (only one priming site present—no co-compartmentalization) during the PCR cycling and 10 000 fold amplification when both priming sites present (co-compartmentalization).

After emulsion PCR the theoretical amounts of the different DNA species are:

Streptavadin fragment (100 bp): $10^7$ molecules

Streptavadin fragment (100 nt): 20 cycles times $10^7$ molecules=$2 \times 10^8$ molecules YoctoReactor fragment (250 bp): $10^9$ molecules YoctoReactor fragment (250 nt): 20 cycles times $10^9$ molecules=$2 \times 10^{10}$ molecules (all original Biotin fragment assumed converted to fused species see below)

Fused genotype—known binder: Fragment A (Streptavadin-Biotin DNA fragment) (330 bp): 10 000×$10^6$ molecules=$10^{10}$ (PCR amplification times number of biotin fragments)—the probability under the above mentioned assumption for co-compartmentalize the Biotin fragment with target DNA is 1.

Fused genotype—non-binder: Fragment B (random co-compartmentalized fragments) (330 bp): 10 000×$10^{-3}$×$10^9$ molecules=$10^{10}$ (PCR amplification times probability for random co-compartmentalization times number of initial yR library molecules)—the probability under the above mentioned assumption for co-compartmentalize a non-binder is #target molecules/# compartments=$10^7/10^{10}=10^{-3}$ Consequently, after this process 50% of the 330 bp fragments contain DNA origination from biotin. Moreover, the 330 bp fragment constitutes about 15 ng and constitutes most of the total double stranded DNA. The single stranded DNA is conveniently removed by ExoSAP-IT (Amersham Biosciences) according to manufactures instructions and the 330 bp fragment is conveniently PAGE purified by standard procedure.

Analysis of Enrichment by DNA Sequencing Using 454 Sequencing Technology

The 454 sequencing priming sites is introduced by PCR using primers with terminal A and B sequences. The resulting fragment is PAGE purified and submitted for 454 DNA sequencing using manufactures protocol.

The DNA sequences are analyzed and the frequency of the biotin genotype calculated.

Conclusions

As can be understood from above—by using the method as described herein one gets an 1000 times enrichment—It is expected from the above calculation that the biotin genotype will be observed with a high frequency ~1 out 2 whereas each of the assumed non-binding yoctoreactor library members will be observed ~1 out of 2 million on average. Consequently, the binder has been enriched 1000 fold over each of the non-binders. This will demonstrate the feasibility of the present new invention.

Example 2

Enrichment by Co-Compartmentalization Using eLigation for Genotype-Genotype Fusion—Spiking Experiment.
For overview see FIG. 1.
Methods

```
DNA oligonucleotides used
vip1481:
                                      (SEQ ID NO: 10)
GAACAGGACCGA vip1471:
                                      (SEQ ID NO: 11)
CTGTTCGATCTTGGGCGTAT
```

```
vip2513:
                                    (SEQ ID NO: 12)
ACGCCCAAGATCGAACAG
```

Biotin-modified continuous one-stranded DNA analogue to the yoctoreactor: x-CGCTAAtggtccctggcagtctccT-TAGCGgaccGACTCcTgctcGAAGACAACGGTgttttacAC-CGT TGTCTTCgagcTgtACCTGCgcAAGTGCgttttacG-CACTTgcGCAGGTacTgtGCATCgacAAG ACCgttttacGGTCTTgtcGATGCacTgGAGTCggtcCTGT-TCGATCTTGGGCGTAT (x=5'-biotin-TEG) (SEQ ID NO:1)

The biotin-modified continuous one-stranded DNA analogue to the yoctoreactor may be assembled by smaller oligonucleotides essentially as described in Hansen et al. J. Am. Chem. Soc., 2009, 131 (3), pp 1322-1327) using a 5'-biotin TEG-modified oligonucleotide in the 5'-position

```
vip2514: x-
                                    (SEQ ID NO: 13)
GCCTTGCCAGCCCGCTCAGGGGAAGGACGTTGGTGTAGAAGCGTTCACTT
GGTGGAAGTAT (x = 5' carboxyl)

vip2515:
                                    (SEQ ID NO: 14)
ACTTCCACCAAGTGAACGCT vip157:
                                    (SEQ ID NO: 8)
GCCTTGCCAGCCCGCTCAG vip660:
                                    (SEQ ID NO: 9)
TGGTCCCTGGCAGTCT
```

Preparation of Yoctoreactor Library

The library is constructed according to Hansen et al. J. Am. Chem. Soc., 2009, 131 (3), pp 1322-1327) with the following modifications:
1) The splint oligonucleotide vip1481 (SEQ ID NO:10) and the oligonucleotide vip1471 (SEQ ID NO; 11) are used for introducing the backward priming site
2) The oligonucleotide vip2513 (SEQ ID NO:12) is used for the dismantling of the yoctoreactor by primer extension Preparation of Known Target Binder (Biotin) Attached to Encoding DNA The known target binder (biotin) attached to double-stranded encoding DNA is made by dismantling the biotin-modified continuous one-stranded DNA analogue to the yoctoreactor by primer extension using vip2513 (SEQ ID NO:12). (Hansen et al. J. Am. Chem. Soc., 2009, 131 (3), pp 1322-1327). The primer is chosen, so a 3'-overhang of 2 nt is made. The 3'-overhang will facilitate the subsequent ligation.

The double stranded DNA fragment is purified by PAGE purification according to standard procedure (Molecular Cloning: A Laboratory Manual (3-Volume Set), 3rd Edition, 2001-01 by Joseph Sambrook, David W. Russell, Publisher: Cold Spring Harbor Laboratory Press) and ethanol precipitated.

Preparation of Target DNA (TD)

Protocol

The 61-mer target DNA is prepared by primer extension and subsequently purified on a 10% TBE-PAGE native gel. The primer is chosen, so a 2 nucleotide 3'-overhang, complementary to the 3'-overhang of the yoctoreactor 3'-overhang, is made. Furthermore, ligation is enabled by phosphorylating the primer.

Example:

Phosphorylation of Primer

2 µL (200 pmol) vip2515 (SEQ ID NO:14)
20 µL 10× buffer 0 (50 mM Tris-HCl (pH 7.5 at 37° C.),
10 mM MgCl2,
100 mM NaCl, 0.1 mg/ml BSA)
2 µl 100 mM ATP (final concentration 2 mM)
10 µL T4 Polynucleotide Kinase (100 u)
66 µL Water, nuclease-free The phosphorylation reaction is incubated @37 degrees C. for 30 minutes, and the kinase is inactivated by incubation @75 degrees C. for 10 minutes The DNA is precipitated by ethanol precipitation, washed in 70% ethanol, and resuspended in 10 µL TE buffer.

Primer Extension:

10 µL phosphorylated vip2515 (200 pmoles) (SEQ ID NO:14)
10 µL 10× buffer 0 (New England Biolabs)
2 µL 10 mM dNTP mix (final concentration 0.2 mM of dATP, dCTP, dGTP, and dTTP)
77 µL water
1 µL (5u) Klenow (exo-, 5 u/µL)

The reaction is allowed to proceed for 15 minutes, and the double stranded DNA purified by extraction from a 15% acrylamide gel according to standard procedure (Molecular Cloning: A Laboratory Manual (3-Volume Set), 3rd Edition, 2001-01 by Joseph Sambrook, David W. Russell, Publisher: Cold Spring Harbor Laboratory Press). and ethanol precipitated DNA—target conjugation Materials 1-Ethyl-3-[3-dimethylaminopropyl]carbodiimide hydrochloride (EDC, 100 mM stock freshly prepared, Aldrich E6383)

N-Hydroxysulfosuccinimide (s-NHS, 200 mM stock, Aldrich 56485)

Morpholinoethanesulfonic acid, MES buffer pH 6.0, 500 mM beta-Mercaptoethanol, 500 mM stock PCR product with 5' carboxyl group on lower strand (see above)

Streptavidin protein (AbCam 78833) (Target protein)

Protocol

The carboxyl modified oligonucleotide (ssDNA) or PCR product with terminal carboxyl can be pre-activated using EDC/s-NHS system prior to reaction with target protein (see refs for examples of activation of various types of carboxyls). Exposure of target protein to EDC may render it inactive, e.g. by chemically modifying tyrosine or cysteine residues. Thus, before mixing the activated DNA-carboxyl with target protein, residual EDC optionally may be quenched by addition of e.g. beta-mercaptoethanol to a final concentration of 20 mM.

Example Pre-Activation Mixture

| | Final conc |
|---|---|
| 10 µL DNA (ssDNA or dsDNA) | |
| 10 µL 500 mM MES, pH 6 | 100 mM |
| 2.5 µL 100 mM EDC | 5 mM |
| 2.5 µL 200 mM s-NHS | 10 mM |
| 25 µL water | |
| Total 50 µL | |

Carboxylic acid activation is allowed to incubate at 20 C for 15-30 min.

Optional: To quench residual EDC, 2 µL of 500 mM beta-mercaptoethanol in water was added (final conc. 20 mM).

Subsequently, the s-NHS-activated ester should be used immediately.

Test of Pre-Activation

An aliquot of the preactivation mixture (25 pmoles ssDNA) can be diluted with water and a 1% phenethylamine in MeCN (primary amine that quenches the activated ester). This mixture can be allowed to react for 15 min, followed by precipitated using EtOH. After dissolution in 100 mM triethylammonium acetate (TEAA, pH 7), the DNA product can be analyzed by RP-HPLC using a gradient of MeCN in 100 mM TEAA.

Shift from initial retention time to higher retention time indicates 1) transformation of carboxyl→NHS ester and 2) subsequent reaction with amine.

Reaction with Target Protein

Check enzyme shipment buffer composition for primary amines. This protocol should tolerate the presence of e.g. DTT or EDTA in the protein stock solution, but primary amines must be removed e.g. by dialysis. Primary amines will quench the activated ester thus abolishing DNA—protein cross-link.

Otherwise, mix pre-activation mixture and enzyme as concentrated as possible to drive chemical reactions.

This should be allowed to incubate for 1-2 h at 20 C (possibly overnight in cases of slow reaction) then purify DNA—protein complex by e.g. electrophoresis.

Association Mixture

A diverse YoctoReactor library consisting of $10^6$ different molecules and a total of $10^9$ molecules i.e. potential ligands coupled to double stranded (ds) DNA, is spiked with $10^6$ biotin molecules coupled to ds DNA (known target binder). The spiked library is mixed with $10^7$ molecules streptavadin coupled to dsDNA (target attached to DNA). The molecules in the mixtures are allowed to associate in a total volume of 3 µl Binding Buffer (PBS, 0.05% tween20, 0.2% BSA for 1 hour at room temperature to reach equilibrium. The concentration of streptavidin (the target) is around 6 pM which is more that 100 fold more than the reported $K_d$ of the biotin-streptavidin complex of $\sim 10^{-14}$ mol/L, which means that practically all biotin will be streptavidin bound at equilibrium.

Ligation Mixture

1× Taq ligation buffer (20 mM Tris-HCl, 25 mM potassium acetate, 10 mM Magnesium Acetate, 1 mM NAD, 10 mM Dithiothreitol 0.1% Triton X-100 pH 7.6 @ 25° C.) is added 2 µL (40 u/µL) Taq DNA ligase in a total volume of 610 µL.

67 mM Tris-HCl (pH 8.8), 16.6 mM $NH_4SO_4$, 6.7 mM $MgCl_2$, 10 mM 2-mercaptoethanol, 1 mM of each dNTP, 7.5 µM of each primer (vip157 (SEQ ID NO:8) and vip660 (SEQ ID NO:9)), 45 units of Taq polymerase in a total volume of 610 µl Ligation in Emulsion Two mL of an emulsion consisting of approx. $5\times10^9$ compartments per ml is prepared by a method similar to the method described by Dressman et al., 2003.

The DNA fragments coupled to the target (streptavadin) or ligands (non-binding or binding), respectively, are able to be ligated on one strand. i.e. two types of combined fragment may be generated through ligation; fragment (A) signifies that Streptavadin and Biotin have been present in the same compartment and fragment (B) signifies that Streptavadin and a random library molecule (not biotin linked) have been present in the same compartment.

The two types of fragments can be differentiated through sequencing or restriction site digestion.

One mL and 500 µL (1.5 mL) continuous phase is prepared by dissolving 4.5% (vol/vol) Span80 in mineral oil, followed by 0.40% (vol/vol) Tween80 and 0.05% (vol/vol) Triton X-100 under constant stirring (1,400 rpm) in a 5 ml round bottom Cryo vial, using a magnetic stirring bar with a pivot ring. The continuous phase is split into two times 600 µL in separate 5 ml round bottom Cryo vials and is kept ice-cold.

The aqueous phase is made by adding 597 µl ice-cold ligation mixture to the 3 µL association mixture. Three hundred (300) µL of the aqueous phase is gradually added (10 µL every 15 s) to each of the two continuous phases under constant stirring (1400 rpm) using a magnetic stirring bar with a pivot ring. After addition of the aqueous phase, the stirring is continued for 30 min under ice-cold conditions.

The emulsions are heated to 45 degrees C. and allowed to ligate for one hour.

Breaking the Emulsion

The ligation mixtures are added 30 µL 500 mM EDTA each and vortexed briefly. The DNA fragments are rescued by pooling the emulsions and centrifuging at 13,000 g for 5 min at 25° C. The oil phase is discarded. Residual mineral oil and surfactants are removed from the emulsion by performing the following extraction twice: add 1 ml of water-saturated diethyl ether, vortex the tube, and dispose of the upper (solvent) phase.

The DNA is concentrated by precipitation, is fractionated by size on denaturing 10% polyacrylamide gels and the ligated fragments isolated by PAGE purification according to standard procedure (Molecular Cloning: A Laboratory Manual (3-Volume Set), 3rd Edition, 2001-01 by Joseph Sambrook, David W. Russell, Publisher: Cold Spring Harbor Laboratory Press), ethanol precipitated and resuspended in 10 µL TE buffer.

Amplification of ligated DNA

Finally, the ligated fragments are amplified by PCR

Example:

PCR Mixture:

10 µL purified ligated DNA

50 µL 2×PCR mastermix (40 mM Tris-HCl, 20 mM $(NH_4)_2SO_4$, 20 mM KCl, 16 mM $MgSO_4$, 0.2% Triton X-100, 0.2 mg/mL BSA, 0.4 mM each of dATP, dTTP, dGTP, and dCTP, pH 8.8 @ 25° C.)

10 µL 5M Betaine (final conc. 0.5M)

1 µL 50 µM vip167 (SEQ ID NO:8) (final conc 0.5 µM)

1 µL 50 µM vip660 (SEQ ID NO:9) (final conc. 0.5 µM)

1 µL (2 u/µL) Vent (exo-) polymerase

27 µL water

The mixture is subjected to thermal cycling by applying the following program in a PCR machine:

92 degrees C., 2 min, 25 cycles of (92 degrees C. 30 seconds, 72 degrees C. 1 min), 72 degrees C. for 2 min.

The resulting library of DNA fragments is sequenced, and the enrichment for the binding fragment calculated.

Anticipated Results

Assuming; equal size spherical compartments, random distribution of molecules and complex in compartments, 100% association of Streptavadin-Biotin complex, no dissociation of Streptavadin-Biotin complex, assuming none or few binders with adequate binding affinity for streptavidin in the yR library, no bias of the ligation reaction or the following PCR reaction,—no co-compartmentalization)

during the ligation and 100 reaction efficiency when the library and target DNA fragments are co-compartmentalized.

After emulsion ligation, theoretical amounts of the ligated DNA species are: (all original Biotin fragment assumed converted to fused species see below)

Ligated genotype—known binder: Fragment A (Streptavadin-Biotin DNA fragment) (250 bp): $10^6$ molecules—the probability under the above mentioned assumption for co-compartmentalize the Biotin fragment with target DNA is 1.

Fused genotype—non-binder: Fragment B (random co-compartmentalized fragments) (250 bp): $10^{-3} \times 10^9$ molecules=$10^6$ (Probability for random co-compartmentalization times number initial yR library molecules)—the probability under the above mentioned assumption for co-compartmentalize a non-binder is #target molecules/# compartments=$10^7/10^{19}=10^{-3}$ The final PCR amplification is expected to be of same efficiency for the two types of molecules, and Consequently, after this process 50% of the 330 bp fragments contain DNA originating from the biotin-streptavidin binding.

Analysis of Enrichment by DNA Sequencing Using 454 Sequencing Technology

The 454 sequencing priming sites is introduced by PCR using primers with terminal A and B sequences. The resulting fragment is PAGE purified and submitted for 454 DNA sequencing using manufactures protocol.

The DNA sequences are analyzed and the frequency of the biotin genotype calculated.

Conclusions

As can be understood from above—by using the method as described herein one gets an 1000 times enrichment—It is expected from the above calculation that the biotin genotype will be observed with a high frequency ~1 out 2 whereas each of the assumed non-binding yoctoreactor library members will be observed ~1 out of 2 million on average. Consequently, the binder has been enriched 1000 fold over each of the non-binders. This will demonstrate the feasibility of the present new invention.

Examples Below:

All the Examples below were made based on the technical information disclosed above (e.g. in the working examples above) plus based on the common general knowledge of the skilled person.

Example 3

Enrichment by Co-Compartmentalization Using Overlap ePCR for Genotype-Genotype Fusion The fundamental principle of ECC, co-compartmentalization of binding partners and fusion of their attached DNA as a result hereof, was demonstrated, using biotin and streptavidin (SA) as the binding partners. Biotin DNA conjugate (yR_biotin) was subjected to ECC using SA conjugated to DNA (SA_TD001) as the target. As a negative control ECC was run in parallel using SA_TD001 preincubated with biotin as the targets. For overview see FIG. 2.

Methods

DNA Oligonucleotides Applied:

Applied for continuous strand of DNA analogue to the yoctoreactor (Hansen et al. J. Am. Chem. Soc., 2009, 131 (3), pp 1322-1327):

(SEQ ID NO: 1)
CGCTAAtggtccctggcagtctccTTAGCGgaccGACTCcTgctcGAAGA
CAACGGTgttttacACCGTTGTCTTCgagcTgtACCTGCgcAAGTGCgtt
ttacGCACTTgcGCAGGTacTgtGCATCgacAAGACCgttttacGGTCTT
gtcGATGCacTgGAGTCggtcCTGTTCGATCTTGGGCGTAT vip1481:
(SEQ ID NO: 10)
GAACAGGACCGA vip1471:
(SEQ ID NO: 11)
CTGTTCGATCTTGGGCGTAT Applied for yR_biotin
vip1461:
(SEQ ID NO: 2)
ATACGCCCAAGATCGAACAG vip2501:
(SEQ ID NO: 3)
x-TGGTCCCTGGCAGTCTCC (x = biotin-TEG)

Applied for e PCR
vip157:
(SEQ ID NO: 8)
GCCTTGCCAGCCCGCTCAG vip660:
(SEQ ID NO: 9)
TGGTCCCTGGCAGTCT Applied for TD001
vip2500:
(SEQ ID NO: 7)
x-GCCTTGCCAGCCCGCTCAG (x = carboxyl modification)

vip2502:
(SEQ ID NO: 6)
CTGTTCGATCTTGGGCGTAT vip2512:
(SEQ ID NO: 5)
GCCTTGCCAGCCCGCTCAGGCAAGTCTTACAGCCGATCAGTCTTCCTTGG
TGCCTGAAG vip2507:
(SEQ ID NO:15)
CTGTTCGATCTTGGGCGTATTGTTTTAGCTGCCCCAACTCCTTCAGGCAC
CAAGGAAGAC Applied for Rescue PCR
vip2549:
(SEQ ID NO: 16)
GCAAGTCTTACAGCCGATCA vip660:
(SEQ ID NO: 9)
TGGTCCCTGGCAGTCT Preparation of yR Continuous strand of DNA analogue to the yoctoreactor (SEQ ID NO: 1) was constructed as described in example 1

Preparation of yR_Biotin

Preparation of known target binder (biotin) attached to yR was constructed as described in example 1

Preparation of Target DNA (TD001)

The TD001 was prepared as described in example 1 except the oligo vip2507 (SEQ ID NO:15) being applied instead of Vip2504 (SEQ ID NO: 4).

Materials

MOPS 3-(N-Morpholino) propanesulfonic acid (Sigma-Aldrich)

Silicone polyether/cyclopentasiloxane (Dow Corning, DC5225C)

Cyclopentasiloxane/trimethylsiloxysilicate (Dow Corning, DC749)

AR20 silicone oil (Sigma-Aldrich)

1-Ethyl-3-[3-dimethylaminopropyl]carbodiimide hydrochloride (EDC, 100 mM stock freshly prepared, Aldrich E6383)

N-Hydroxysulfosuccinimide (s-NHS, 200 mM stock, Aldrich 56485)

Morpholinoethanesulfonic acid, MES buffer pH 6.0, 500 mM beta-Mercaptoethanol, 500 mM stock PCR product with 5' carboxyl group on lower strand (see above)

Streptavidin protein (AbCam 78833) (Target protein)

Slide-A-lyzer mini (Pierce)

TissueLyzer II (Qiagen)

DNA—Target Conjugation

Pre-Activation

Pre-activation was done by mixing 5.4 µl TD001 [9.3 µM] with 1 µl MOPS pH 6 [1 M], 1 µl EDC [50 mM], 1 µl s-NHS [100 mM] and 1.6 µl water. Carboxylic acid activation is allowed to incubate at 20° C. for 30 min.

To quench residual EDC, 1 µl of 250 mM beta-mercaptoethanol in water was added.

Reaction with Target Protein

Prior to conjugation, SA was dialyzed 2 times 30 min against Dialysis Buffer (10 mM MOPS (pH 8), 50 mM NaCl) using Slide-A-Lyzer mini dialysis device according to manufactures instructions (Pierce).

5 µl of dialyzed SA [58 µM] was added to 1.6 µl MOPS pH 6 [1 M], 1.6 µl NaCl in water [1 M] and 11 µl TD001 [4.6 µM]. The reaction was allowed for 2 hours at 20° C.

To quench the reaction, 2 µl Tris pH 8 [1 M] was added. The SA_TD001 conjugate was isolated from reactants by PAGE from a 6% TBE gel that was run for 40 min at 200V.

The bands are extracted 3 times in 500 µl Extraction Buffer (50 mM Tris pH8, 150 mM NaCl, 0.1% Tween20) at 4° C. (30 min/o.n./30 min).

Residual gel was removed by filtration, and the samples concentrated in a Microcon YM30 device according to manufactures instructions (Millipore). The concentration of the conjugate was estimated to be 0.38 µM by measuring the DNA concentration using Picogreen according to manufactures instructions (Molecular Probes).

Association Reactions (Binding Reaction)

Prior to yR_biotin and SA_TD001 binding, 6e8 molecules SA_TD001 molecules/µl in a total volume of 50 µl Association Buffer (10 mM Tris-HCl (pH 7.8), 0.05% Triton-X100.) was incubated with or without 1 µM biotin (6e11 molecules biotin/µl) for 30 min at 20° C.

The following binding reactions were made in Association Buffer:

1) 3e8 yR_biotin molecules/µl and 3e8 SA_TD001 molecules/µl in a total volume of 50 µl, using SA_TD001 that had not been pre-incubated with biotin 2) 3e8 yR_biotin molecules/µl and 3e8 SA_TD001 molecules/µl in a total volume of 50 µl, using SA_TD001 that had been pre-incubated with biotin.

The binding reaction was incubated for 1 h at 20° C. and hereafter diluted to a concentration of 3e6 molecules/µl of yR_biotin and 3e6 molecules/µl SA_TD001 in Association Buffer.

Emulsion PCR (ePCR)

Assembly of yR and TD001 and amplification of yR_TD001 fusion molecule in emulsion using PCR.

Continuous Phase

Continuous phase was prepared as described by (Turner and Hurles, Nat Protoc. 2009; 4(12): 1771-1783).

1200 µl continuous phase was made per reaction

480 µl Silicone polyether/cyclopentasiloxane (DC5225C)

360 µl Cyclopentasiloxane/trimethylsiloxysilicate (DC749)

360 µl AR20 silicone oil

PCR Aqueous Phase

600 µl PCR aq. was made per reaction:

60 µl Pfu buffer (10×)

12 µl BSA (50 mg/ml)

12 µl dNTP (10 mM)

3 µl Vip157 (SEQ ID NO: 8) (100 µM)

3 µl Vip660 (SEQ ID NO: 9) (100 µM)

4 µl Pfu—turbo (2.5 u/µl)

446 µl water

60 µl template the resulting concentration of yR_biotin and SA_TD001 are 3e5 molecules/µl of each Emulsification In a 2 ml Eppendorf tube 1000 µl continuous phase and 500 µl PCR phase, and a 5 mm steel bead were added per reaction The reaction was emulsified by mixing for 8 min at 30 Hz in a Tissuelyser II at 20° C. 100 µl emulsion was added per PCR tube and the mixture was subjected to thermal cycling by applying the following program in a PCR machine: 92° C. for 2 min, 30 cycles of (92° C. 30 seconds, 55° C. for 1 min and 72° C. for 1.5 min), 72° C. for 5 min.

Recovery of DNA

The emulsion was broken by adding 100 µl 1-butanol per PCR tube. The contents of 8 PCR tubes per condition were pooled and 600 µl NaCl in water [4 M] was added. The content was mixed by vortexing for 10 sec at max speed, and the organic phase was removed after centrifugation at 14000 g for 1 min. Another 800 µl 1-butanol was added to the pooled PCR product and the vortexing and centrifugation step was repeated. The extraction with 1-butanol was repeated one more time.

The DNA was further purified by PCR purification columns (Macherey-Nagel) according to manufactures instructions. Elute with 50 µl elution buffer per condition The eluted DNA was diluted 20 fold in Dilution Buffer (10 mM Tris (pH 7.8), 20 mM NaCl, 0.1% Triton-X100) prior to the rescue PCR.

Rescue PCR

Amplification of yR_TD001 fusion molecule

PCR Mixture Per Reaction:

50 µL 2×PCR mastermix (40 mM Tris-HCl, 20 mM $(NH_4)_2SO_4$, 20 mM KCl, 16 mM $MgSO_4$, 0.2% Triton X-100, 0.2 mg/mL BSA, 0.4 mM each of dATP, dTTP, dGTP, and dCTP, pH 8.8 at 25° C.)

1 µL 50 µM vip2549 (final conc 0.5 µM) (SEQ ID NO:16)

1 µL 50 µM vip660 (SEQ ID NO:9) (final conc. 0.5 µM)

1 µL (2 u/µL) Vent (exo-) polymerase

10 µl template

37 µL water

The mixture was subjected to thermal cycling by applying the following program in a PCR machine:

92° C. for 2 min, 20 cycles of (92° C. 30 seconds, 55° C. for 1 min and 72° C. for 1.5 min), 72° C. for 5 min.

Results

Figure 4:
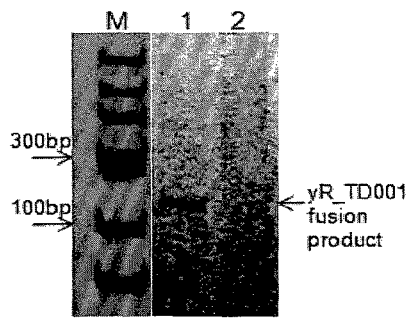
FIG. 4 shows a gel of fusion products obtained using the procedures described in Example 3.

The fusion product yR_TD001 has a predicted length of 245 bp. The DNA products were visualized on a 10% TBE PAGE run for 40 min. at 200V. The results showed the presence of a band with the expected size, if the association reaction was performed without pre-incubation with biotin (lane 1) and the absence of a band if association reaction was performed on molecules that had been pre-incubated with biotin (lane 2), see FIG. 4.

Conclusion

This result demonstrated co-compartmentalization of binding partners and fusion of their attached DNA as a result hereof.

Example 4

Enrichment by Co-Compartmentalization Using Overlap ePCR for Genotype-Genotype Fusion—Spiking Experiment ECC was demonstrated by enriching for yR_biotin that was spiked into a diverse yR library using SA_TD001 as the target. As a negative control ECC was run in parallel using SA_TD001 preincubated with biotin as the targets.

Methods

DNA Oligonucleotides Applied

Applied for continuous strand of DNA analogue to the yoctoreactor (Hansen et al. J. Am. Chem. Soc., 2009, 131 (3), pp 1322-1327):

```
                                            (SEQ ID NO: 1)
CGCTAAtggtccctggcagtctccTTAGCGgaccGACTCcTgctcGAAG ACAACGGTgttttacACCGTTGTCTTCgagcTgtACCTGCgcAAGTGCg ttttacGCACTTgcGCAGGTacTgtGCATCgacAAGACCgttttacGGT CTTgtcGATGCacTgGAGTCggtcCTGTTCGATCTTGGGCGTAT vip1481:
                                            (SEQ ID NO: 10)
GAACAGGACCGA vip1471:
                                            (SEQ ID NO: 11)
CTGTTCGATCTTGGGCGTAT Applied for yR_biotin
vip1461:
                                            (SEQ ID NO: 2)
ATACGCCCAAGATCGAACAG vip2501:
                                            (SEQ ID NO: 3)
x-TGGTCCCTGGCAGTCTCC  (x = biotin-TEG)

Applied for e PCR
vip157:
                                            (SEQ ID NO: 8)
GCCTTGCCAGCCCGCTCAG vip660:
                                            (SEQ ID NO: 9)
TGGTCCCTGGCAGTCT Applied for TD001
vip2500:
                                            (SEQ ID NO: 7)
x-GCCTTGCCAGCCCGCTCAG  (x = carboxyl modification)

vip2502:
                                            (SEQ ID NO: 6)
CTGTTCGATCTTGGGCGTAT vip2512:
                                            (SEQ ID NO: 5)
GCCTTGCCAGCCCGCTCAGGCAAGTCTTACAGCCGATCAGTCTTCCTTG
TGCCTGAAG vip2507:
                                            (SEQ ID NO: 15)
CTGTTCGATCTTGGGCGTATTGTTTTAGCTGCCCCAACTCCTTCAGGCAC
CAAGGAAGAC Applied for Rescue PCR
vip2549:
                                            (SEQ ID NO: 16)
GCAAGTCTTACAGCCGATCA vip660:
                                            (SEQ ID NO: 9)
TGGTCCCTGGCAGTCT Applied for PCR of a yR diverse library
vip341:
                                            (SEQ ID NO: 17)
TGGTCCCTGGCAGTCTCC vip1461:
                                            (SEQ ID NO: 2)
ATACGCCCAAGATCGAACAG Applied for 454 PCR
vip2593:
                                            (SEQ ID NO: 18)
CCTATCCCCTGTGTGCCTTGGCAGTCTCAGGTCTTCCTTGGTGCCTGAAG vip2465:
                                            (SEQ ID NO: 19)
CCATCTCATCCCTGCGTGTCTCCGACTCAGAGGTTGGTCCCTGGCAGTCT
CC vip2467:
                                            (SEQ ID NO: 20)
CCATCTCATCCCTGCGTGTCTCCGACTCAGATCGTGGTCCCTGGCAGTCT
CC vip2468:
                                            (SEQ ID NO: 21)
CCATCTCATCCCTGCGTGTCTCCGACTCAGATGCTGGTCCCTGGCAGTCT
CC vip2469:
                                            (SEQ ID NO; 22)
CCATCTCATCCCTGCGTGTCTCCGACTCAGCACTTGGTCCCTGGCAGTCT
CC vip2470:
                                            (SEQ ID NO: 23)
CCATCTCATCCCTGCGTGTCTCCGACTCAGCAGATGGTCCCTGGCAGTCT
CC vip2471:
                                            (SEQ ID NO: 24)
CCATCTCATCCCTGCGTGTCTCCGACTCAGCCATTGGTCCCTGGCAGTCT
CC
```

Preparation of yR_Biotin yR_biotin was prepared as described in example 1

Preparation of a Diverse Yoctoreactor Library

The yR library was essentially constructed as described by (Hansen et al. J. Am. Chem. Soc., 2009, 131 (3), pp 1322-1327). The diverse yR library was PCR amplified by the following method;

PCR mixture per reaction:

50 µL 2×PCR mastermix (40 mM Tris-HCl, 20 mM $(NH_4)_2SO_4$, 20 mM KCl, 16 mM $MgSO_4$, 0.2% Triton X-100, 0.2 mg/mL BSA, 0.4 mM each of dATP, dTTP, dGTP, and dCTP, pH 8.8 at 25° C.)

10 µL 5M Betaine (final conc. 0.5M)

1 µL 50 µM vip341 (SEQ ID NO: 17) (final conc 0.5 µM)

1 µL 50 µM vip1461 (final conc. 0.5 µM) (SEQ ID NO:2)

1 µL ($10^8$ molecules) of continuous stranded DNA analogue to the yoctoreactor (SEQ ID NO:1)

1 µL (2 u/µL) Vent (exo-) polymerase

36 µL water

The mixture was subjected to thermal cycling by applying the following program in a PCR machine:

92° C. for 2 min, 15 cycles of (92° C. for 30 seconds, 72° C. for 1 min), 72° C. for 2 min.

The 185 bp DNA fragment was purified by PAGE purification according to standard procedure (Molecular Cloning: A Laboratory Manual (3-Volume Set), 3rd Edition, 2001-01 by Joseph Sambrook, David W. Russell, Publisher: Cold Spring Harbor Laboratory Press) and ethanol precipitated Association Reactions (Binding Reactions)

Binding reactions was performed as described in example 3, with the following changes.

Prior to yR_biotin and SA_TD001 binding, 6e8 molecules SA_TD001 molecules/μl in a total volume of 50 μl association buffer was incubated with or without 1 μM biotin (6e11 molecules biotin/μl) for 30 min at 20° C.

The following association reactions were made in Association Buffer:

1) 3e7 yR_biotin molecules/μl and 3e8 SA_TD001 molecules/μl in a total volume of 50 μl, using SA_TD001 that had not been pre-incubated with biotin
2) 3e7 yR_biotin molecules/μl and 3e8 SA_TD001 molecules/μl in a total volume of 50 μl, using SA_TD001 that had been pre-incubated with biotin.

Binding reactions were incubated for 1 h at 20° C.

Hereafter the following conditions were setup:

A) Without biotin pre-incubation: A 1000 fold dilution of binding reaction (1) to a concentration of 3e4 molecules/μl of yR_biotin and 3e5 molecules/μl SA_TD001 in Association Buffer containing 3e7 molecules yR library/μl (final concentration).
B) With biotin pre-incubation: A 1000 fold dilution of association reaction (2) to a concentration of 3e4 molecules/μl of yR_biotin and 3e5 molecules/μl SA_TD001 in Association Buffer containing 3e7 molecules yR library/μl (final concentration).
C) Without yR-biotin: Association Buffer containing a 3e7 yR library molecules/μl and 3e5 molecules/μl SA_TD001 in Association Buffer was made Emulsion PCR ePCR was performed as described in example 3, but performed in duplicate and with 40 PCR cycles Recovery of DNA Breaking of emulsions was performed as described in example 3, but performed by pooling the emulsions from 16 PCR tubes and eluting with 100 μl elution buffer per condition Rescue PCR Rescue PCR was performed as described in example 3, but with the following thermal profile during PCR amplification; 92° C. for 2 min, 20 cycles of (92° C. for 30 seconds, 72° C. for 1.5 min), 72° C. for 5 min.

Preparation for 454-Sequencing

PCR protocol for amplification of yR_TD001 fusion molecules hereby including 454 sequence tags into the sequences leading to a predicted size of 309 bp. For each condition and duplicate a unique forward primer was applied.

PCR Mixture Per Reaction:

50 μL 2×PCR mastermix (40 mM Tris-HCl, 20 mM $(NH_4)_2SO_4$, 20 mM KCl, 16 mM $MgSO_4$, 0.2% Triton X-100, 0.2 mg/mL BSA, 0.4 mM each of dATP, dTTP, dGTP, and dCTP, pH 8.8 at 25° C.)

10 μL 5M Betaine (final conc. 0.5M)

1 μL 50 μM vip2593 (SEQ ID NO:18) (final conc 0.5 μM)

2 μL 25 μM vip2465 (SEQ ID NO:19), vip2467 (SEQ ID NO:20), vip2468 (SEQ ID NO:21), vip2469 (SEQ ID NO:22), vip2470 (SEQ ID NO:23) or vip2471 (SEQ ID NO:24) (final conc. 0.5 μM)

5 μL Template from each condition and duplicate

1 μL (2 u/μL) Vent (exo-) polymerase

31 μL water

The DNA was purified on PCR purification columns (Macherey-Nagel) according to manufactures instructions and the DNA concentrations were determined using a spectrophotometer (Eppendorf). The concentrations were adjusted upon comparative visual inspection of the products on 10% TBE gels that were run for 40 min at 200V. The DNA products were pooled so that all DNA products were represented by similar amounts of DNA. The pooled DNA was run on a 10% TBE PAGE gel and a DNA fragment of approx. 309 bp was purified by PAGE purification according to standard procedure (Molecular Cloning: A Laboratory Manual (3-Volume Set), 3rd Edition, 2001-01 by Joseph Sambrook, David W. Russell, Publisher: Cold Spring Harbor Laboratory Press), and ethanol precipitated.

454-Sequencing 454-sequencing was performed as described by (Hansen et al. J. Am. Chem. Soc., 2009, 131 (3), pp 1322-1327).

Results

The sequencing results showed, see FIG. 5, that although the yR_biotin was spiked into the yR library in a 1000 fold lower concentration than the yR library the percentages of yR_biotin counts were:

37.6% and 32% for the duplicates in condition (A) i.e. enrichment without pre-incubation of SA_TD001 with biotin.

0.30% and 0.72% for the duplicates in condition (B) i.e. enrichment with pre-incubation of SA_TD001 with biotin.

0.02% and 0.05% for the duplicates in condition (C) i.e. enrichment without yR_biotin included in the sample.

Consequently, more than 300 fold enrichment of yR_biotin was observed using SA_TD001 as the target. In contrast, the negative control target, SA_TD001 preincubated with biotin, provided a 3-7 fold enrichment.

Conclusion

ECC was demonstrated by enriching for yR_biotin that was spiked into a diverse yR library using SA_TD001 as the target.

Example 5

Enrichment by Co-Compartmentalization Using eLigation for Genotype-Genotype Fusion The fundamental principle of ECC, co-compartmentalization of binding partners and fusion of their attached DNA as a result hereof, was demonstrated, using desthiobiotin (desBio) and streptavidin (SA) as the binding partners. Desthiobiotin DNA conjugate (yR_desBio) was subjected to ECC using SA conjugated to DNA (SA_TD002) as the target. As a negative control ECC was run in parallel using SA_TD002 preincubated with biotin as the targets.

For overview see FIG. 1.

Methods

DNA oligonucleotides used are described in example 2. In addition, the following were applied:

Applied for yR labeled with desthiobiotin (desBio_yR):

vip2815:

(SEQ ID NO: 25)
x-TGGTCCCTGGCAGTCTCC (x = desthiobiotin)

vip2535:

(SEQ ID NO: 26)
CACCACGATGGCAATGCATTCTTCGCTGCCATTCTG

-continued

Applied for rescue PCR:
vip660:
(SEQ ID NO: 9)
TGGTCCCTGGCAGTCT vip2824:
(SEQ ID NO: 27)
CGATGTCCTGAGGTGGAAGT Applied for 'Scavenger DNA':
vip2554:
(SEQ ID NO: 28)
GGCAAGTGATTGTCCATGTGCATGAGAAGAGGCCCACATT vip2555:
(SEQ ID NO: 29)
CACATGGACAATCACTTGCC vip2556:
(SEQ ID NO: 30)
AATGTGGGCCTCTTCTCATG Applied for TD002
vip2528:
(SEQ ID NO: 31)
TCCACATCCTCCAGTTCA vip2529:
(SEQ ID NO: 32 and 43)
AGCTGGAGCTTGCTGTTAGC vip2530:
(SEQ ID NO: 33)
AGGTTCGCTCCCTCCTTAAGTCAGGAGGATGTGACACCAA vip2531:
(SEQ ID NO: 34)
CGATGTCCTGAGGTGGAAGTTGAACTGGAGGATGTGGACA vip2532:
(SEQ ID NO: 35 and 46)
CTTAAGGAGGGAGCGAACCTGCTAACAGCAAGCTCCAGCT vip2558:
(SEQ ID NO: 36)
x-TTGGTGTCACATCCTCCTGA (x = C6-amino modification)

Preparation of yR Labeled with Desthiobiotin (desBio_yR)

A 5'-desthiobiotin was introduced in the yR analogue by using primers vip2815 (SEQ ID NO:25) and vip2535 (SEQ ID NO:26) in PCR with a continuous stranded DNA analogue to the yoctoreactor library sequences as template DNA (Hansen et al. J. Am. Chem. Soc., 2009, 131 (3), pp 1322-1327). To create a 2 bp overhang suitable for ligation to target DNA conjugated with streptavidin, the PCR product was digested with BseMI.

Preparation of Target DNA (TD002)

Protocol

TD002 (98 bp double stranded DNA with a GA nucleotide overhang and 5' carboxyl group on the lower strand) was assembled by ligation of phosphorylated oligonucleotides vip2528 (SEQ ID NO:31), vip2529 (SEQ ID NO:32 and 43), vip2530 (SEQ ID NO:33), vip2531 (SEQ ID NO:34) and vip2532 and the non-phosphorylated oligonucleotide vip2558 (SEQ ID NO:36). Phosphorylation with T4 Polynucleotide Kinase and ligation with T4 DNA ligase was performed according to manufactures instructions (Fermentas). The double stranded DNA fragment was purified by PAGE purification according to standard procedure (Molecular Cloning: A Laboratory Manual (3-Volume Set), 3rd Edition, 2001-01 by Joseph Sambrook, David W. Russell, Publisher: Cold Spring Harbor Laboratory Press) and precipitated with ethanol. Prior to ligation vip2559 (SEQ ID NO:47) was modified to have a 5' carboxyl group. Thus, simple C6-amino modification was interchanged to a carboxylic acid by treatment with disuccinimidylsuberate (DSS, C8-di-NHS ester, Pierce #21580). The oligonucleotide was treated with 40 mM DSS in HEPBS buffer pH 9 in a water—NMP 1:1 mixture over night followed by treatment with LiOH to hydrolyse the remaining NHS ester. After neutralization and precipitation, the crude carboxy modified oligonucleotide was used without further modification.

Preparation of Target DNA Conjugated with Streptavidin (SA_TD002)

The SA_TD002 was prepared as described in example 3.

Association Reactions (Binding Reaction)

Materials

1 M Tris-HCl, pH 7.5
4 M NaCl
10% triton X-100
10 µM biotin
SA_TD002
desBio_yR

Protocol

In a total volume of 0.5 µl Binding Buffer (10 mM Tris-HCl (pH7.5), 50 mM NaCl, 0.1% triton), 3E8 desBio_yR molecules were mixed with 1.4E9 molecules SA_TD002 in the presence or absence of 1 µM biotin (inhibitor). Association of the molecules was allowed by incubating the binding mixtures for 1 hour on ice.

Dissociation Reactions (Dilution)

Materials

Standard Ligation Buffer:
50 mM Tris-HCl, pH 7.5
50 mM NaCl
0.1% Triton X-100
0.75 µM BSA
9 mM KCL
4.5% Glycerol
0.2 mM EDTA
1 mM DTT
2 mM ATP
1 µM T4 DNA ligase (Fermentas)
0.01 µM 'Scavenger DNA' (40-mer nicked dsDNA fragment):

40-mer dsDNA fragment containing a single nick was prepared by assembly of oligonucleotides vip2554 (SEQ ID NO:28), phosphorylated vip2555 (SEQ ID NO:29) and vip2556 (SEQ ID NO:30).

Continuous phase was prepared as described in example 3

2 mL micro tubes with screw cap

Protocol

A volume of 0.12 µL was transferred from the binding mixture to the lid of a 2 mL Eppendorf tube containing 600 µL aqueous phase containing 1 µM T4 DNA ligase (standard ligation buffer). The dissociation reaction was initiated by mixing the binding mixture with the aqueous phase by inverting the tubes twice followed by vortexing the tubes for 10 seconds. After a short spin in the microcentrifuge, 500 µL of the mixture was transferred to an ice-cold 2 mL micro tube containing 1 mL continuous phase and left on ice for the remaining time to finally obtain a dissociation time of 2 minutes.

Emulsification

Materials

Induction buffer:
50 mM Tris-HCl, pH 7.5
50 mM NaCl 0.1% Triton X-100
1.5 µM BSA
10 mM KCL
5% Glycerol
0.2 mM EDTA
1 mM DTT
2 mM ATP
135 mM MgCl2
Protocol The dissociation reactions were terminated exactly 2 min. after initiation by mixing the continuous phase (1 mL) and the aqueous phase (0.5 mL) by emulsification for 3×20 seconds at 5500 rpm (with 10 seconds pause in between the 20 seconds runs) on the Precellys24 (Bertin Technologies). In parallel, induction-emulsions containing magnesium but no ligase for the activation of T4 DNA ligase were prepared by emulsification for 3×20 seconds at 5500 rpm of 1 mL continuous phase and 0.5 mL aqueous phase containing 135 mM $MgCl_2$ (Induction Buffer).

Ligation in Emulsion
Protocol

A volume of 150 µL induction-emulsion containing $MgCl_2$ was added per emulsion and mixed by rotation for one hour at RT to activate T4 DNA ligase. Ligation of desBio_yR and SA_TD002 in emulsion was allowed by incubating the emulsions (1650 µL) for 16 hours in a thermo block at 16° C. and 300 rpm.

Emulsion Breaking and DNA Recovery
Materials
1-butanol
Isopropanol
100% ethanol
100 bp no-limits DNA
PCR clean-up kit (NucleoSpin ExtractII, Macherey-Nagel)
10% triton X-100
Protocol The ligation reaction was stopped by incubating the tubes for 30 minutes at 65° C. followed by a short spin in the microcentrifuge. For breaking of the emulsions, half of the volume of each emulsion was transferred to a clean 2 mL eppendorf tube. To each tube 850 µL 1-butanol plus 15 ng 100 bp no-limits DNA [10 ng/µL] was added and mixed by thoroughly vortexing for 10 seconds. The tubes were centrifuged for 1 min at 14,000×g and the supernatant was discarded. Residual silicone oil and surfactants were removed from the emulsion by repeating the 1-butanol extraction once more with the addition of 1 volume of 1-butanol. The recovered water-phases of the previously splitted emulsions were pooled into one tube and the DNA fragments (desBio_yR_TD002_SA fusion molecules) were rescued by purification using a PCR clean-up kit (NucleoSpin ExtractII, Macherey-Nagel) according to the supplier's recommendations. The DNA was eluted into EB buffer (5 mM Tris/HCl, pH 8.5) containing 0.1% triton X-100. Prior to qPCR analysis, the eluted DNA was diluted 10 fold in Dilution Buffer (10 mM Tris-HCl pH 7.5, 10 mM NaCl, 0.05% Triton-X100).

Figure 6:
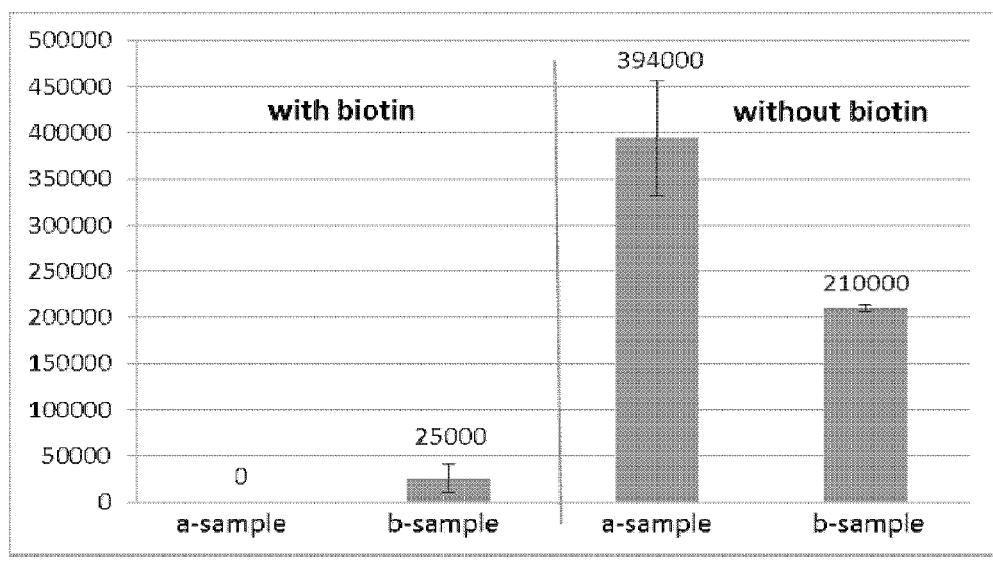
FIG. 6 shows results from rescue PCR as described in Example 5.

Amplification and Analysis of Ligated DNA (Rescue PCR)
Materials
2×PCR Mastermix (pH 8.8 at 25° C.):
40 mM Tris-HCl
20 mM $(NH_4)_2SO_4$
20 mM KCl
16 mM $MgSO_4$,
0.2% Triton X-100,
0.2 mg/mL BSA
0.4 mM of each nucleotide suitable for hot-start PCR dATP, dTTP, dGTP, and dCTP (CleanAmp, TriLink)
Protocol To analyze the number of desBio_yR_TD002_SA fusion molecules present in the different emulsions, qPCR with primers vip660 (SEQ ID NO:9) and vip2824 (SEQ ID NO:27) and using 5 µL of the 10 fold diluted purified recovered DNA samples as a template was run. For the standard curve 3E8, 3E7, 3E6, 3E5 or 3E4 copies of pre-ligated yR_TD002 (control template) were added per qPCR reaction.

qPCR mixture per reaction:
5 µL template
10 µL 2×PCR mastermix
2 µL 5M Betaine (final conc. 0.5 M)
0.4 µL SyBR Green (final conc. 2.5E-5%)
0.2 µL 100 µM vip660 (final conc. 1 µM)
0.2 µL 100 µM vip2824 (SEQ ID NO:27) (final conc 1 µM)
0.2 µL (2 u/µL) Vent (exo-) polymerase (Fermentas)
2 µL water The mixture was subjected to thermal cycling by applying the following program in the qPCR machine:
92° C. for 10 min
30 cycles of 95° C. 30 seconds and 72° C. for 2 min 30 seconds
72° C. for 5 min Results In order to calculate the number of fusion molecules present in the different qPCR reactions, the standard curve was defined. The calculated numbers of desBio_yR TD002 SA fusion molecules were translated into a column chart to visualize the difference between the signal obtained in association reactions incubated in presence or absence of 1 µM biotin (FIG. 6). The results show the presence of a significantly higher number of fusion molecules if the association reaction was performed in the absence of biotin compared to if the association reaction was performed in the presence of the inhibitor biotin.

Conclusion

This result demonstrated co-compartmentalization of desBio_yR and SA_TD002 molecules originating from the desthiobiotin-streptavidin binding and ligation of their attached DNA as a result hereof.

Example 6

Enrichment by Co-Compartmentalization Using eLigation for Genotype-Genotype Fusion—Spiking Experiment ECC was demonstrated by enriching for N-benzyl-4-sulfamoyl-benzamide conjugated to yR DNA (BSB_yR) that was spiked into a diverse yR library using human Carbonic anhydrase II as the target. As a negative control ECC was run in parallel using target preincubated with BSB as the target. Furthermore, dissociation time dependent enrichment was demonstrated in the same system.

For overview see FIG. 1.

Methods

DNA oligonucleotides used are described in example 2 and 5. In addition, the following were applied:

Used for yR labeled with BSB (BSB_yR):
vip2260:

(SEQ ID NO: 37)
ATGAAAGACGTGGCCATTGC

-continued vip2724_vip2607 (SEQ ID NO: 38):
CTGACATGGTCCCTGGCAGTCTCCTGTCAGGACCGACTCCXGCTCGAAGA
C (x = dT-C6-amino modification)

vip2970:
(SEQ ID NO: 39)
CTATCGGTTTTACCGATAGGTCTTCGAGCTGTACCTGCGC vip2973:
(SEQ ID NO: 40)
AGCTAGGTTTTACCTAGCTGCGCAGGTACTGTGCATCGAC vip2980:
(SEQ ID NO: 41)
CTATCGGTTTTACCGATAGGTCGATGCACTGGAGTCGGTC Used for TD003:
vip2536:
(SEQ ID NO: 42)
CTTATGCTGGCAGTTTCA vip2529:
(SEQ ID NO: 32 and 43)
ACTTCCACCTCAGGACATCGAGCTGGAGCTTGCTGTTAGC vip2538:
(SEQ ID NO: 44)
AGGTTCGCTCCCTCCTTAAGCCAGCAGTGGTAATTCGACA vip2996:
(SEQ ID NO: 45)
CGATGTCCTGAGGTGGAAGTTGAAACTGCCAGCATAAGGA vip2532:
(SEQ ID NO: 35 and 46)
CTTAAGGAGGGAGCGAACCTGCTAACAGCAAGCTCCAGCT vip2559:
(SEQ ID NO: 47)
x-TGTCGAATTACCACTGCTGG (x = C6-amino modification)

Used for 454-sequencing:
Vip3018:
(SEQ ID NO: 48)
CCTATCCCTGTGTGCCTTGGCAGTCTCAGCGATGTCCTGAGGTGGAAGT vip2459:
(SEQ ID NO: 49)
CCATCTCATCCCTGCGTGTCTCCGACTCAGAACCTGGTCCCTGGCAGTCT
CC vip2460:
(SEQ ID NO: 50)
CCATCTCATCCCTGCGTGTCTCCGACTCAGAAGGTGGTCCCTGGCAGTCT
CC vip2461:
(SEQ ID NO: 51)
CCATCTCATCCCTGCGTGTCTCCGACTCAGACACTGGTCCCTGGCAGTCT
CC vip2462:
(SEQ ID NO: 52)
CCATCTCATCCCTGCGTGTCTCCGACTCAGACTGTGGTCCCTGGCAGTCT
CC vip2463:
(SEQ ID NO: 53)
CCATCTCATCCCTGCGTGTCTCCGACTCAGAGAGTGGTCCCTGGCAGTCT
CC vip2464:
(SEQ ID NO: 54)
CCATCTCATCCCTGCGTGTCTCCGACTCAGAGCATGGTCCCTGGCAGTCT
CC vip2465:
(SEQ ID NO: 19)
CCATCTCATCCCTGCGTGTCTCCGACTCAGAGGTTGGTCCCTGGCAGTCT
CC vip2466:
(SEQ ID NO: 55)
CCATCTCATCCCTGCGTGTCTCCGACTCAGAGTCTGGTCCCTGGCAGTCT
CC vip2467:
(SEQ ID NO: 20)
CCATCTCATCCCTGCGTGTCTCCGACTCAGATCGTGGTCCCTGGCAGTCT
CC vip2468:
(SEQ ID NO: 21)
CCATCTCATCCCTGCGTGTCTCCGACTCAGATGCTGGTCCCTGGCA-
GTCTCC vip2469:
(SEQ ID NO: 22)
CCATCTCATCCCTGCGTGTCTCCGACTCAGCACTTGGTCCCTGGCAGTCT
CC vip2470:
(SEQ ID NO: 23)
CCATCTCATCCCTGCGTGTCTCCGACTCAGCAGATGGTCCCTGGCAGTCT
CC vip2471:
(SEQ ID NO: 24)
CCATCTCATCCCTGCGTGTCTCCGACTCAGCCATTGGTCCCTGGCAGTCT
CC vip2472:
(SEQ ID NO: 56)
CCATCTCATCCCTGCGTGTCTCCGACTCAGCCTATGGTCCCTGGCAGTCT
CC vip2473:
(SEQ ID NO: 57)
CCATCTCATCCCTGCGTGTCTCCGACTCAGCGAATGGTCCCTGGCAGTCT
CC vip2474:
(SEQ ID NO: 58)
CCATCTCATCCCTGCGTGTCTCCGACTCAGCTACTGGTCCCTGGCAGTCT
CC vip2475:
(SEQ ID NO: 59)
CCATCTCATCCCTGCGTGTCTCCGACTCAGCTCATGGTCCCTGGCAGTCT
CC vip2476:
(SEQ ID NO: 60)
CCATCTCATCCCTGCGTGTCTCCGACTCAGCTGTTGGTCCCTGGCAGTCT
CC vip2477:
(SEQ ID NO: 61)
CCATCTCATCCCTGCGTGTCTCCGACTCAGCTTGTGGTCCCTGGCAGTCT
CC vip2478:
(SEQ ID NO: 62)
CCATCTCATCCCTGCGTGTCTCCGACTCAGGAACTGGTCCCTGGCAGTCT
CC vip2479:
(SEQ ID NO: 63)
CCATCTCATCCCTGCGTGTCTCCGACTCAGGACATGGTCCCTGGCAGTCT
CC vip2480:
(SEQ ID NO: 64)
CCATCTCATCCCTGCGTGTCTCCGACTCAGGAGTTGGTCCCTGGCAGTCT
CC vip2481:
(SEQ ID NO: 65)
CCATCTCATCCCTGCGTGTCTCCGACTCAGGATGTGGTCCCTGGCAGTCT
CC -continued

```
vip2482:
                                              (SEQ ID NO: 66)
CCATCTCATCCCTGCGTGTCTCCGACTCAGGCAATGGTCCCTGGCAGTCT
CC vip2483:
                                              (SEQ ID NO: 67)
CCATCTCATCCCTGCGTGTCTCCGACTCAGGTCTTGGTCCCTGGCAGTCT
CC vip2484:
                                              (SEQ ID NO: 68)
CCATCTCATCCCTGCGTGTCTCCGACTCAGGTGATGGTCCCTGGCAGTCT
CC vip2485:
                                              (SEQ ID NO: 69)
CCATCTCATCCCTGCGTGTCTCCGACTCAGTACGTGGTCCCTGGCAGTCT
CC vip2486:
                                              (SEQ ID NO: 70)
CCATCTCATCCCTGCGTGTCTCCGACTCAGTAGCTGGTCCCTGGCAGTCT
CC vip2487:
                                              (SEQ ID NO: 71)
CCATCTCATCCCTGCGTGTCTCCGACTCAGTCAGTGGTCCCTGGCAGTCT
CC vip2488:
                                              (SEQ ID NO: 72)
CCATCTCATCCCTGCGTGTCTCCGACTCAGTCCATGGTCCCTGGCAGTCT
CC vip2489:
                                              (SEQ ID NO: 73)
CCATCTCATCCCTGCGTGTCTCCGACTCAGTCGTTGGTCCCTGGCAGTCT
CC vip2490:
                                              (SEQ ID NO: 74)
CCATCTCATCCCTGCGTGTCTCCGACTCAGTCTCTGGTCCCTGGCAGTCT
CC vip2491:
                                              (SEQ ID NO: 75)
CCATCTCATCCCTGCGTGTCTCCGACTCAGTGACTGGTCCCTGGCAGTCT
CC vip2492:
                                              (SEQ ID NO: 76)
CCATCTCATCCCTGCGTGTCTCCGACTCAGTGTGTGGTCCCTGGCAGTCT
CC vip2493:
                                              (SEQ ID NO: 77)
CCATCTCATCCCTGCGTGTCTCCGACTCAGTTCCTGGTCCCTGGCAGTCT
CC vip2494:
                                              (SEQ ID NO: 78)
CCATCTCATCCCTGCGTGTCTCCGACTCAGTTGGTGGTCCCTGGCAGTCT
CC
```

Preparation of Yoctoreactor Library

The library was constructed according to (Hansen et al. J. Am. Chem. Soc., 2009, 131 (3), pp 1322-1327) but in the tetramer format instead of the trimer format.

Preparation of yR Labeled with BSB (BSB_yR)

Materials 10 mM Fmoc-NH-PEG(12)-CO$_2$H 100 mM 4-(4,6-Dimethoxy-1,3,5-triazin-2-yl)-4-methylmorpholinium chloride (DMT-MM) 200 mM N-(2-Hydroxyethyl)piperazine-N'-(4-butanesulfonic acid) pH 9 (HEPBS)

N-Methyl-2-pyrrolidone (NMP)

0.5 M piperidine in NMP 10 mM Fmoc-L-Phenylglycine (Fmoc-L-Phg)

10 mM 4-carboxybenzenesulfonamide 0.1 M acetonitrile/triethylammonium acetate (pH 7)

BSB: BSB was synthesized according to (Drabovich et al., *Anal. Chem.* 2009, 81, 490-494)

Protocol

BSB_yR was prepared by ligation. Position 2 oligonucleotide vip2970 (SEQ ID NO:39), position 3 oligonucleotide vip2973 (SEQ ID NO:40) and position 4 oligonucleotide vip2980 (SEQ ID NO:41) were prepared for ligation by phosphorylation with T4 Polynucleotide Kinase performed according to manufactures instructions (Fermentas). BSB labeling of position 1 oligonucleotide vip2724_vip2607 (SEQ ID NO:38) was synthesized according to the following reaction scheme:

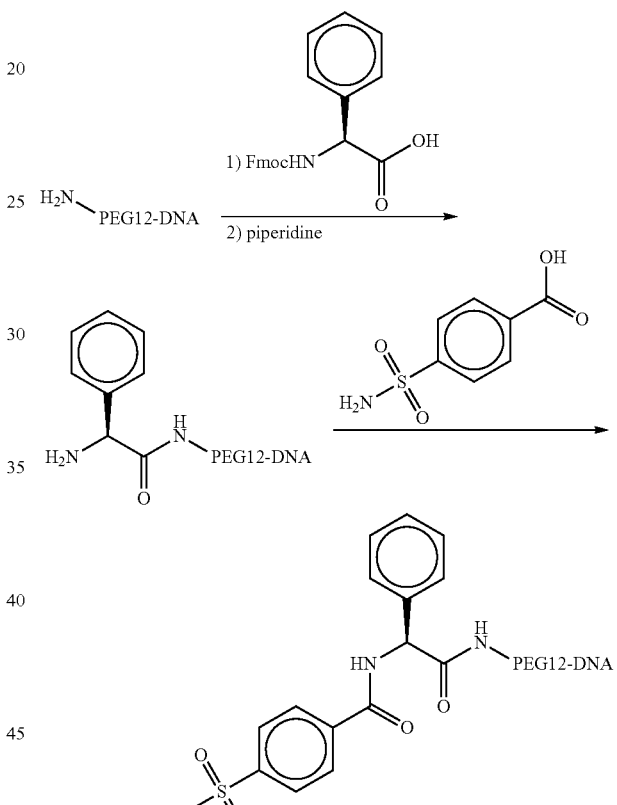

Amino-PEG12 derived oligonucleotide was synthesized from a 51mer oligonucleotide (vip2724_vip2607) (SEQ ID NO:38) [5 nmol] with internally modified dT (amino-C6-dT) that was coupled with Fmoc-NH-PEG(12)-CO$_2$H [10 mM] in a solution of 100 mM DMT-MM, 200 mM HEPBS pH 9, in 200 mL NMP:water 1:1. After 1 hour the mixture was ethanol precipitated and dissolved in 100 mL water. A volume of 100 mL 0.5 M piperidine in NMP was added and incubated at 25° C. for 2 hr. The amino-PEG12-oligonucleotide was isolated by ethanol precipitation and used without further purification in the next coupling. BSB-PEG12 labeled position 1 conjugate was synthesized by conjugating Fmoc-L-Phg to a 51mer amino modified oligonucleotide in which the primary amine was linked through a PEG12 linker on an internally modified dT. The amino-PEG12 derived oligonucleotide was coupled with Fmoc-L-Phg [10 mM] in a solution of 100 mM DMT-MM and 200 mM HEPBS pH 9 in 200 mL NMP:water 1:1. After 1 hour the mixture was ethanol precipitated and dissolved in 100 mL water. 100 mL 0.5 M piperidine in NMP was added and incubated at 25° C. for 2 hr. Final coupling of 4-carboxybenzenesulfonamide was made by treatment of a solution of the L-Phg-PEG12 derived oligonucleotide with 4-carboxybenzenesulfonamide [10 mM] in a solution of 100 mM DMT-MM and 200 mM HEPBS pH 9 in 200 mL NMP:water 1:1. After incubation at 25° C. for 1 hour the crude oligonucleotide conjugate was isolated by ethanol precipitation and purified by reverse phase HPLC on a C-18 Waters XBridge column with acetonitrile/triethylammonium acetate (pH 7, 0.1 M) gradient 6—50% acetonitrile over 20 min. Appropriate fractions were collected and evaporated in vacuo and resulted into 1680 pmol of vip2724_vip2607 (SEQ ID NO:38) labeled with BSB. Equivalent amounts of the stem complimentary position 1 oligonucleotide vip2724_vip2607 (SEQ ID NO: 89) conjugated with BSB, position 2, position 3 and position 4 oligonucleotides were mixed and ligated to form the yR (Hansen et al. *J. Am. Chem. Soc.*, 2009, 131 (3), pp 1322-1327). Ligation with T4 DNA ligase was performed according to manufactures instructions (Fermentas). The BSB_yR was un-folded and made double stranded via primer extension using phosphorylated vip2260 (SEQ ID NO:37) in a Klenow (exo-) driven reaction performed according to manufactures instructions (Fermentas).

Preparation of Target DNA (TD003)

TD003 was prepared similar to TD002 as described in example 5.

Conjugation of Carbonic Anhydrase II to TD003 (CAII003)

Recombinant human CAII (RnD systems; 2184CA)

Protocol

Conjugation of TD003 to CAII was done similarly as described in example 3.

Pre-activation mixture with target DNA for conjugation with CAII. Pre-activation was done by mixing 21 µL TD003 [4.7 µM] with 3 µL MOPS pH 6 [1 M], 3 µL EDC [50 mM], and 3 µL s-NHS [100 mM].

Carboxylic acid activation was allowed to incubate at 20° C. for 30 min.

The buffer was removed by using a G25 Illustra column according to manufactures instructions (GE Healthcare).

Prior to conjugation, the protein was dialyzed 2×30 min against a Dialysis Buffer at 4° C. using Slide-A-Lyzer mini dialysis device according to manufactures instructions (Pierce). For the conjugation reaction 1 µL MOPS [1M] pH 8.0, 1 µL NaCl [1 M] and 1 µL water was added to 9 µL of dialyzed CAII protein. Approx. 35 µL activated DNA was added to this mixture. The reaction was incubated at 4° C. for 20 h.

The conjugation reaction was quenched by adding Tris (pH 8) to a final concentration of 50 mM. The CAII_TD003 conjugate was isolated from reactants by PAGE from a 6% TBE gel as described in example 3. The concentration of the conjugate was estimated to be 0.21 µM by measuring the DNA concentration using Picogreen according to manufactures instructions (Molecular Probes).

Association Reactions (Binding Reaction)

Materials

1 M Tris-HCl, pH 7.5
4 M NaCl
10% triton
10 µM BSB

Protocol

In a total volume of 1.5 µl Binding Buffer (10 mM Tris-HCl (pH7.5), 50 mM NaCl, 0.1% triton X-100), 6.5E10 library molecules and 3.3E5 BSB_yR molecules (YoctoReactor library consisting of 1E12 molecules spiked 1 to 200 000 with 5E6 BSB_yR molecules) were mixed with 9E9 molecules CAII_TD003 in the presence or absence of 1 µM BSB (inhibitor). Association of the molecules was allowed by incubating the binding mixtures for 1 hour on ice.

Dissociation Reactions (Dilution)

Materials

Standard ligation buffer:
50 mM Tris-HCl, pH 7.5
50 mM NaCl
0.1% Triton X-100
0.75 µM BSA
9 mM KCL
4.5% Glycerol
0.2 mM EDTA
1 mM DTT
2 mM ATP
1 µM T4 DNA ligase (Fermentas)
0.01 µM 'Scavenger' DNA Continuous phase was prepared as described in example 3

2 mL micro tubes with screw cap

Protocol

A volume of 0.12 µl was transferred from the binding mixture to the lid of a 2 mL Eppendorf tube containing 600 µL aqueous phase containing 1 µM T4 DNA ligase (standard ligation buffer). The dissociation reaction was initiated by mixing the binding mixture with the aqueous phase by inverting the tubes twice followed by vortexing the tubes thoroughly for 10 seconds. After a short spin on the micro centrifuge, 500 µL of the mixture was transferred to an ice-cold 2 mL tube containing 1 mL continuous phase and left on ice for the remaining time to finally obtain dissociation times of 2 or 30 minutes.

Emulsification

Materials

Induction buffer:
50 mM Tris-HCl, pH 7.5
50 mM NaCl
0.1% Triton X-100
1.5 µM BSA
10 mM KCL
5% Glycerol
0.2 mM EDTA
1 mM DTT
2 mM ATP
135 mM $MgCl_2$ Protocol The dissociation reaction was terminated exactly 2 min or 30 min after initiation by mixing the continuous phase (1 mL) and the aqueous phase (0.5 mL) by emulsification for 3×20 seconds at 5500 rpm (with 10 seconds pause in between the 20 seconds runs) on the Precellys 24 (Bertin Technologies). In parallel, induction-emulsions containing magnesium but no ligase for the activation of T4 DNA ligase were prepared by emulsification for 3×20 seconds at 5500 rpm of 1 mL continuous phase and 0.5 mL aqueous phase containing 135 mM $MgCl_2$ (induction buffer).

Ligation in Emulsion

Protocol

A volume of 150 µL induction-emulsion containing $MgCl_2$ was added per emulsion and mixed by rotation for one hour at RT to activate T4 DNA ligase. Ligation was allowed by incubating the emulsions (1650 µL) for 16 hours in a thermo block at 16° C. and 300 rpm.

Emulsion Breaking and DNA Recovery
Materials
1-butanol
Isopropanol
100% ethanol
100 bp no-limits DNA
TissueLyser II (Qiagen)
PCR clean-up kit (NucleoSpin ExtractII, Macherey-Nagel)
10% triton X-100
Protocol The ligation reaction was stopped by incubating the tubes for 30 minutes at 65° C. followed by a short spin on the micro centrifuge. For breaking of the emulsions, 300 µL 1-butanol, 150 µL isopropanol, 50 µL ethanol and 20 ng 100 bp no-limits DNA [10 ng/µL] was added per emulsion and mixed on the TissueLyser II (Qiagen) for 1 min at 15 Hz. Subsequently the tubes were rotated for 1 hour at RT, centrifuged for 2 min at 14,000×g and the supernatant was discarded. Residual silicone oil and surfactants were removed from the emulsion by performing the following extraction twice: addition of 1 volume of 1-butanol, mixing for 1 min at 15 Hz on the TissueLyser, and discarding the upper phase. The DNA fragments were rescued by purification using a PCR clean-up kit (NucleoSpin ExtractII, Macherey-Nagel) according to the supplier's recommendations. The DNA was eluted into EB buffer (5 mM Tris/HCl, pH 8.5) containing 0.1% triton.

Amplification of Ligated DNA (Rescue PCR)
Materials
2×PCR Mastermix (pH 8.8 at 25° C.):
40 mM Tris-HCl
20 mM $(NH_4)_2SO_4$
20 mM KCl
16 mM $MgSO_4$,
0.2% Triton X-100,
0.2 mg/mL BSA
0.4 mM of each nucleotide suitable for hot-start PCR dATP, dTTP, dGTP, and dCTP (CleanAmp, TriLink)
Protocol The ligated fragments were amplified by PCR using 10 µL of the purified recovered DNA samples as a template in a total volume of 100 µL.

PCR mixture:
10 µL template DNA
50 µL 2×PCR Mastermix
10 µL 5 M Betaine (final conc. 0.5 M)
1 µL 100 µM vip660 (SEQ ID NO:9) (final conc. 1 µM)
1 µL 100 µM vip2824 (SEQ ID NO:27) (final conc. 1 µM)
1 µL (2 u/µL) Vent (exo-) polymerase (Fermentas)
27 µL water The mixture was subjected to thermal cycling by applying the following program in a PCR machine:
10 min at 95° C.
32 cycles of 30 sec at 95° C. and 2 min 30 sec at 72° C.
2 min at 72° C.

Preparation for 454-Sequencing
Protocol

Samples for 454-sequencing were prepared as described for the yR_TD001 fusion molecules in example 4. 454-Sequencing tags were included in the PCR for amplification of yR_TD003 fusion molecules using unique forward primers vip2459 (SEQ ID NO:49) to vip2494 (SEQ ID NO:78).

DNA Sequencing
Protocol

454-Sequencing was performed as described by (Hansen et al. J. Am. Chem. Soc., 2009, 131 (3), pp 1322-1327). The DNA sequences were analyzed and the frequency of the BSB genotype calculated.

Results

The sequencing results (FIG. 7) showed that the BSB_yR was successfully enriched for (about 1300 fold) by CA II using a dissociation time of two minutes. In contrast, no enrichment of BSB_DNA was observed when using a dissociation time of 30 minutes or when CA II was preincubated with BSB prior to the binding step.

Conclusion

ECC was demonstrated by enriching in dissociation time dependent fashion for BSB_yR that was spiked into a diverse yR library using CAII as the target.

REFERENCE LIST

1: EP1809743B1 (Vipergen)
2: EP1402024B1 (Nuevolution)
3: EP1423400B1 (David Liu)
4: Nature Chem. Biol. (2009), 5:647-654 (Clark)
5: WO 00/23458 (Harbury)
6: Nature Methods (2006), 3(7), 561-570 7: 2006 (Miller)
7: Nat. Biotechnol. 2004; 22, 568-574 (Melkko)
8: Nature. (1990); 346(6287), 818-822 (Ellington)
9: Proc Natl Acad Sci USA (1997). 94 (23): 12297-302 (Roberts)
10: WO06053571A2 (Rasmussen)
11: Bertschinger et al. (2007) Protein Engineering, Design & Selection vol. 20 no. 2 pp. 57-68
12: Miller O J, Bernath K, Agresti J J, Amitai G, Kelly B T, Mastrobattista E, Taly V, Magdassi S, Tawfik D S, Griffiths A D. Directed evolution by in vitro compartmentalization. Nat Methods. 2006 July; 3(7):561-70
13: Doi, N. and Yanagawa, H. (1999) FEBS Lett., 457, 227-230
14: Yonezawa, M., Doi, N., Kawahashi, Y., Higashinakagawa, T. and Yanagawa, H. (2003) Nucleic Acids Res., 31, e118.
15: Tawfik, D. S. and Griffiths, A. D. (1998) Man-made cell-like compartments for molecular evolution. Nat. Biotechnol., 16, 652-656
16: Ghadessy, F. J., Ong, J. L. and Holliger, P. (2001) Proc. Natl Acad. Sci. USA, 98, 4552-4557;
17: Tay Y, Ho C, Droge P, Ghadessy F J. Selection of bacteriophage lambda integrases with altered recombination specificity by in vitro compartmentalization. Nucleic Acids Res. 2010 March; 38(4):e25. Epub 2009 Dec. 4
18: Zheng Y, Roberts R J. Selection of restriction endonucleases using artificial cells. Nucleic Acids Res. 2007; 35(11):e83. Epub 2007
19: Mastrobattista E, Taly V, Chanudet E, Treacy P, Kelly B T, Griffiths A D. High-throughput screening of enzyme libraries: in vitro evolution of a beta-galactosidase by fluorescence-activated sorting of double emulsions. Chem Biol. 2005 December; 12(12):1291-300
20: Levy M, Griswold K E, Ellington A D. Direct selection of trans-acting ligase ribozymes by in vitro compartmentalization. RNA. 2005 October; 11(10):1555-62. Epub 2005 Aug. 30;
21: Sepp A, Choo Y. Cell-free selection of zinc finger DNA-binding proteins using in vitro compartmentalization. J Mol Biol. 2005 Nov. 25; 354(2):212-9. Epub 2005 Oct. 3;

22: Bernath K, Magdassi S, Tawfik D S. Directed evolution of protein inhibitors of DNA-nucleases by in vitro compartmentalization (IVC) and nano-droplet delivery. J Mol Biol. 2005 Feb. 4; 345(5):1015-26. Epub 2004 Dec. 7.

23: Bertschinger et al, (2004) Protein Engineering, Design & Selection vol. 17 no. 9 pp. 699-707

24: Chen Yu et al, (November 2008) Nucleic Acid Research, Vol. 36, Nr. 19, Pages: Article No. E128

25: Hansen et al. J. Am. Chem. Soc., 2009, 131 (3), pp 1322-1327

26: Drabovich et al., Anal. Chem. 2009, 81, 490-494

27: Turner and Hurles, Nat Protoc. 2009; 4(12): 1771-1783

---

What is claimed is:

1. A method for making an enriched library comprising specific nucleic acid sequence information allowing one to identify at least one binding entity that binds to at least one target wherein the specific binding entity has been present in an in vitro display library and wherein the method comprises the steps of:
  (i): making an in vitro display library of at least 100 different binding entities B, wherein each binding entity is attached to a nucleic acid molecule and the nucleic acid molecule comprises specific nucleic acid sequence information allowing to identify the binding entity wherein once one knows the specific nucleic acid sequence information of the nucleic acid molecule one directly knows the structure of the specific binding entity attached to the nucleic acid molecule, wherein the structure of the binding entity attached to the nucleic acid molecule is herein termed B-structure;
  (ii): making nucleic acid molecules with at least one target T, attached to a nucleic acid molecule and the nucleic acid molecule comprises specific nucleic acid sequence information allowing one to identify the specific target, wherein the target is capable of binding to at least one of the binding entities present in the library of step (i)—the structure of the target, attached to the nucleic acid molecule is herein termed T-structure;
  (iii): mixing a solution comprising X, wherein X is a number greater than $10^4$ total numbers of B-structures of the library of step (i) with a solution comprising Y, wherein Y is a number greater than $10^2$ total numbers of T-structures of step (ii) under binding conditions, which are conditions where a B-structure containing a binding entity capable of binding to a target molecule, binds more efficiently to the corresponding T-structure, than a B-structure containing a binding entity not capable of binding to the same target do and wherein one gets binding of at least one of the binding entities to at least one target thereby creating a complex comprising a B-structure bound to a T-structure, which is termed $B_{BoundTo}$T-structure;
  (iv): applying an in vitro compartmentalization system to the solution of step (iii)—under binding conditions, which are conditions where a B-structure containing a binding entity capable of binding to a target molecule, binds more efficiently to the corresponding T-structure, than a B-structure containing a binding entity not capable of binding to the same target do—wherein the compartmentalization system comprises at least 2 times more individual compartments than the Y number of T-structures present in step (iii) under conditions wherein the B-structures, T-structures and $B_{BoundTo}$T-structures enter randomly into the individual compartments so that binding of target with the binding entity of step (iii) is transformed into co-comparmentalization of B-strutures and T-structures; and
  (v): fusing the nucleic acid molecules of a B-structure and a T-structure which are both present within the same individual compartment which is fusing the nucleic acid molecule of the B-structure to the nucleic acid molecule of the T-structure—this structure is herein termed $BT_{Fused}$-structure and the $BT_{Fused}$-structure comprises the specific nucleic acid sequence information allowing one to identify the binding entity of step (i) and the specific nucleic acid sequence information allowing one to identify the specific target of step (ii), wherein said $BT_{Fused}$-structure remains suspended in solution in the individual compartments; and
  (vi): combining the content of the individual compartments of step (v) under conditions wherein there is no fusing of the nucleic acid molecules of a B-structure and a T-structure—wherein there is not created any new $BT_{Fused}$-structure not already created in step (v)—in order to get a library of $BT_{Fused}$-structures, wherein the library is an enriched library of species of $BT_{Fused}$-structures originating from binding pairs of target and binding entity when compared to $BT_{Fused}$-structures originating from nonbinding pairs of target and binding entity; and
  wherein the $B_{BoundTo}$T-structures remain suspended in solution in the individual compartments of step (iv);
  wherein the method does not rely on target immobilization on a solid support; and
  wherein the nucleic acid of $BT_{Fused}$-structures present in the enriched library of step (vi) are amplified.

2. The method of claim 1, wherein binding entity of step (i) is attached to the nucleic acid molecule by a covalent binding and wherein the target of step (ii) is attached to the nucleic acid molecule by a covalent binding and wherein the nucleic acid molecule of the B-structure is DNA and the nucleic acid molecule of the T-structure is DNA.

3. The method of claim 2, wherein the DNA nucleic acid molecule in the B-structure is a double stranded nucleic acid molecule and wherein the DNA nucleic acid molecule in the T-structure is a double stranded nucleic acid molecule.

4. The method of claim 1, wherein the nucleic acid molecule attached to the binding entity in the B-structure contains a PCR priming site and wherein the nucleic acid molecule attached to the target in the T-structure contains a PCR priming site.

5. The method of claim 1, wherein the in vitro library of step (i) comprises at least $10^5$ different binding entities B, and wherein the binding entities of step (i) are chemical compounds with an average molecular weight MW below 5000 dalton.

6. The method of claim 1, wherein there are at least two different targets T in step (ii).

7. The method of claim 1, wherein at least one target is a protein.

8. The method of claim 1, wherein there in step (iii) is at least $10^5$ copies of a T-structure of interest—wherein "Y" is at least $10^5$ and wherein the concentration of T-structures in the "mixing step (iii)" is at least $10^{-9}$ M.

9. The method claim 1, wherein step (iii) is performed under binding conditions, wherein a B-structure containing a binding entity capable of binding to a target molecule, binds 100 fold more efficiently to the corresponding T-structure, than a B-structure containing a binding entity not capable of binding to the same target do.

10. The method of claim 1, wherein said method comprises an additional step (iii-b) that is performed before step (iv), comprising:
- (iii-b): diluting the solution of step (iii) at least 100 fold under binding conditions, which are conditions where a B-structure containing a binding entity capable of binding to a target molecule, binds more efficiently to the corresponding T-structure, than a B-structure containing a binding entity not capable of binding to the same target do.

11. The method of claim 1, wherein there in step (iv) is (a) at least 100 times more individual compartments than the Y number of T-structures present in step (iii) and (b) at least square root 10 (3.16) times more individual compartments than the X number of B-structures in step (iii).

12. The method of claim 1, wherein the in vitro compartmentalization system of step (iv) is a water-in-oil emulsion system and wherein the average compartments volume is less than $10^{-12}$ liter.

13. The method of claim 1, wherein there is an extra step (vii) comprising use of the enriched library of step (vi) to identify at least one individual binding entity that binds to at least one target of interest.

\* \* \* \* \*